US012686697B2

(12) United States Patent
Moussa

(10) Patent No.: US 12,686,697 B2
(45) Date of Patent: Jul. 21, 2026

(54) ADVANTAGEOUS MORPHIC FORM OF AT-527 HEMI-SULFATE SALT

(71) Applicant: Atea Pharmaceuticals, Inc., Boston, MA (US)

(72) Inventor: Adel Moussa, Burlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 429 days.

(21) Appl. No.: 18/226,064

(22) Filed: Jul. 25, 2023

(65) Prior Publication Data

US 2023/0365611 A1 Nov. 16, 2023

Related U.S. Application Data

(63) Continuation of application No. PCT/US2022/013953, filed on Jan. 26, 2022.

(60) Provisional application No. 63/141,789, filed on Jan. 26, 2021.

(51) Int. Cl.
*C07H 19/20* (2006.01)
*A61K 9/20* (2006.01)

(52) U.S. Cl.
CPC ............... *C07H 19/20* (2013.01); *A61K 9/20* (2013.01); *C07B 2200/13* (2013.01)

(58) Field of Classification Search
CPC ............................ C07H 19/20; C07B 2200/13
See application file for complete search history.

(56) References Cited

U.S. PATENT DOCUMENTS

| | | | |
|---|---|---|---|
| 5,977,061 | A | 11/1999 | Holy et al. |
| 6,348,587 | B1 | 2/2002 | Schinazi et al. |
| 6,602,999 | B1 | 8/2003 | Kumar et al. |
| 6,660,721 | B2 | 12/2003 | Devos et al. |
| 6,777,395 | B2 | 8/2004 | Bhat et al. |
| 6,784,166 | B2 | 8/2004 | Devos et al. |
| 6,812,219 | B2 | 11/2004 | LaColla et al. |
| 6,908,924 | B2 | 6/2005 | Watanabe et al. |
| 6,911,424 | B2 | 6/2005 | Schinazi et al. |
| 6,914,054 | B2 | 7/2005 | Sommadossi et al. |
| 6,949,522 | B2 | 9/2005 | Otto et al. |
| 7,094,770 | B2 | 8/2006 | Watanabe et al. |
| 7,105,493 | B2 | 9/2006 | Sommadossi et al. |
| 7,105,499 | B2 | 9/2006 | Carroll et al. |
| 7,125,855 | B2 | 10/2006 | Bhat et al. |
| 7,138,376 | B2 | 11/2006 | Gosselin et al. |
| 7,148,206 | B2 | 12/2006 | Sommadossi et al. |
| 7,157,441 | B2 | 1/2007 | Sommadossi et al. |
| 7,163,929 | B2 | 1/2007 | Sommadossi et al. |
| 7,169,766 | B2 | 1/2007 | Sommadossi et al. |
| 7,192,936 | B2 | 3/2007 | LaColla et al. |
| 7,202,224 | B2 | 4/2007 | Eldrup et al. |
| 7,211,570 | B2 | 5/2007 | Schinazi et al. |
| 7,268,119 | B2 | 9/2007 | Cook et al. |
| 7,285,658 | B2 | 10/2007 | Cook et al. |
| 7,307,065 | B2 | 12/2007 | Schinazi et al. |
| 7,323,449 | B2 | 1/2008 | Olsen et al. |
| 7,339,054 | B2 | 3/2008 | Xu et al. |
| 7,365,057 | B2 | 4/2008 | LaColla et al. |
| 7,384,924 | B2 | 6/2008 | LaColla et al. |
| 7,388,002 | B2 | 6/2008 | Babu et al. |
| 7,429,571 | B2 | 9/2008 | Chand et al. |
| 7,429,572 | B2 | 9/2008 | Clark |
| 7,456,155 | B2 | 11/2008 | Sommadossi et al. |
| 7,495,006 | B2 | 2/2009 | Liotta et al. |
| 7,514,410 | B2 | 4/2009 | Babu et al. |
| 7,534,767 | B2 | 5/2009 | Butora et al. |
| 7,547,704 | B2 | 6/2009 | LaColla et al. |
| 7,560,434 | B2 | 7/2009 | Babu et al. |
| 7,560,550 | B2 | 7/2009 | Doring et al. |
| 7,582,618 | B2 | 9/2009 | Sommadossi et al. |
| 7,601,820 | B2 | 10/2009 | Wang et al. |
| 7,608,597 | B2 | 10/2009 | Sommadossi et al. |
| 7,608,599 | B2 | 10/2009 | Klumpp et al. |
| 7,608,600 | B2 | 10/2009 | Storer et al. |
| 7,608,601 | B2 | 10/2009 | Devos et al. |
| 7,625,875 | B2 | 12/2009 | Gosselin et al. |
| 7,632,821 | B2 | 12/2009 | Butora et al. |
| 7,635,689 | B2 | 12/2009 | LaColla et al. |
| 7,638,502 | B2 | 12/2009 | Schinazi et al. |
| 7,652,001 | B2 | 1/2010 | Hostetler et al. |
| 7,662,798 | B2 | 2/2010 | LaColla et al. |
| 7,662,938 | B2 | 2/2010 | Schinazi et al. |
| 7,691,603 | B2 | 4/2010 | DeFrees |

(Continued)

FOREIGN PATENT DOCUMENTS

| | | | |
|---|---|---|---|
| AU | 2012241173 | A1 | 11/2012 |
| CN | 103435672 | B1 | 12/2013 |

(Continued)

OTHER PUBLICATIONS

U.S. Pat. No. 12,226,429 B2, U.S. Appl. No. 18,225,452, Sommadossi et al., Feb. 18, 2025.
US 2020/0179415 A1, U.S. Appl. No. 16/703,599, Sommadossi et al., Jun. 11, 2020.
US 2025/0082656 A1, U.S. Appl. No. 18/957,362, Moussa et al., Mar. 13, 2025.
US 2025/0109163 A1, U.S. Appl. No. 18/739,149, Moussa et al., Apr. 3, 2025.
U.S. Appl. No. 19/215,054, filed May 21, 2025, Sommadossi et al.
Ahmad, T. et al. "Cardiac dysfunction associated with a nucleotide polymerase inhibitor for treatment of hepatitis C" Hepatology, 62, 409, 2015.

(Continued)

*Primary Examiner* — Bahar Craigo
(74) *Attorney, Agent, or Firm* — Knowles Intellectual Property Strategies, LLC

(57) ABSTRACT

Advantageous isolated morphic Form III of the hemi-sulfate salt of AT-527 that exhibits a faster rate of dissolution over the amorphous form leading to increased bioavailability and thus efficacy for therapeutic administration in a solid dosage form to treat viral indications, as well as processes for its manufacture.

23 Claims, 9 Drawing Sheets

(56) References Cited

U.S. PATENT DOCUMENTS

| | | | |
|---|---|---|---|
| 7,713,941 | B2 | 5/2010 | Cook et al. |
| 7,718,790 | B2 | 5/2010 | Stuyver et al. |
| 7,749,983 | B2 | 7/2010 | Hostetler et al. |
| 7,772,208 | B2 | 8/2010 | Schinazi et al. |
| 7,824,851 | B2 | 11/2010 | Sommadossi et al. |
| 7,842,672 | B2 | 11/2010 | Boojamra et al. |
| RE42,015 | E | 12/2010 | Watanabe et al. |
| 7,879,815 | B2 | 2/2011 | MacCoss et al. |
| 7,902,202 | B2 | 3/2011 | Sommadossi et al. |
| 7,919,247 | B2 | 4/2011 | Stuyver et al. |
| 7,932,240 | B2 | 4/2011 | Dousson et al. |
| 7,951,789 | B2 | 5/2011 | Sommadossi et al. |
| 7,964,580 | B2 | 6/2011 | Sofia et al. |
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,012,942 | B2 | 9/2011 | Butler et al. |
| 8,071,567 | B2 | 12/2011 | Devos et al. |
| 8,071,568 | B2 | 12/2011 | Narjes et al. |
| 8,093,380 | B2 | 1/2012 | Wang et al. |
| 8,114,994 | B2 | 2/2012 | Liotta et al. |
| 8,114,997 | B2 | 2/2012 | Otto et al. |
| 8,119,607 | B2 | 2/2012 | Francom et al. |
| 8,133,870 | B2 | 3/2012 | Babu et al. |
| 8,148,349 | B2 | 4/2012 | Meppen et al. |
| 8,163,703 | B2 | 4/2012 | Babu et al. |
| 8,168,583 | B2 | 5/2012 | Schinazi et al. |
| 8,173,621 | B2 | 5/2012 | Du et al. |
| 8,193,372 | B2 | 6/2012 | Dousson et al. |
| 8,242,085 | B2 | 8/2012 | Babu et al. |
| 8,299,038 | B2 | 10/2012 | Sommadossi et al. |
| 8,318,682 | B2 | 11/2012 | Butler et al. |
| 8,324,179 | B2 | 12/2012 | Chen et al. |
| 8,334,270 | B2 | 12/2012 | Sofia et al. |
| 8,343,937 | B2 | 1/2013 | Sommadossi et al. |
| 8,362,068 | B2 | 1/2013 | Dousson et al. |
| 8,399,428 | B2 | 3/2013 | Wagner |
| 8,399,429 | B2 | 3/2013 | Jonckers et al. |
| 8,415,308 | B2 | 4/2013 | Cho et al. |
| 8,415,309 | B2 | 4/2013 | Francom et al. |
| 8,415,321 | B2 | 4/2013 | Schinazi et al. |
| 8,415,322 | B2 | 4/2013 | Clark |
| 8,431,588 | B2 | 4/2013 | Jonckers et al. |
| 8,440,813 | B2 | 5/2013 | Babu et al. |
| 8,455,451 | B2 | 6/2013 | Cho et al. |
| 8,470,834 | B2 | 6/2013 | Kwong et al. |
| 8,481,510 | B2 | 7/2013 | Jonckers et al. |
| 8,481,712 | B2 | 7/2013 | Bhat et al. |
| 8,481,713 | B2 | 7/2013 | Wang et al. |
| 8,492,539 | B2 | 7/2013 | Chun et al. |
| 8,501,699 | B2 | 8/2013 | Francom et al. |
| 8,507,460 | B2 | 8/2013 | Surleraux et al. |
| 8,541,434 | B2 | 9/2013 | Kwong et al. |
| 8,551,973 | B2 | 10/2013 | Bao et al. |
| 8,552,021 | B2 | 10/2013 | Jonckers et al. |
| 8,563,530 | B2 | 10/2013 | Chang et al. |
| 8,575,119 | B2 | 11/2013 | Wang et al. |
| 8,580,765 | B2 | 11/2013 | Sofia et al. |
| 8,609,627 | B2 | 12/2013 | Cho et al. |
| 8,618,076 | B2 | 12/2013 | Ross et al. |
| 8,629,263 | B2 | 1/2014 | Ross et al. |
| 8,633,309 | B2 | 1/2014 | Ross et al. |
| 8,637,475 | B1 | 1/2014 | Storer et al. |
| 8,642,756 | B2 | 2/2014 | Ross et al. |
| 8,658,616 | B2 | 2/2014 | McGuigan et al. |
| 8,673,926 | B2 | 3/2014 | Chu |
| 8,674,085 | B2 | 3/2014 | Sommadossi et al. |
| 8,680,071 | B2 | 3/2014 | Surleraux et al. |
| 8,691,788 | B2 | 4/2014 | Sommadossi et al. |
| 8,697,694 | B2 | 4/2014 | Arasappan et al. |
| 8,715,638 | B2 | 5/2014 | Kwong et al. |
| 8,716,262 | B2 | 5/2014 | Sofia et al. |
| 8,716,263 | B2 | 5/2014 | Chun et al. |
| 8,735,345 | B2 | 5/2014 | Porter et al. |
| 8,735,372 | B2 | 5/2014 | Du et al. |
| 8,735,569 | B2 | 5/2014 | Ross et al. |
| 8,742,101 | B2 | 6/2014 | Storer et al. |
| 8,759,318 | B2 | 6/2014 | Chamberlain et al. |
| 8,759,372 | B2 | 6/2014 | Roberts et al. |
| 8,759,510 | B2 | 6/2014 | Du et al. |
| 8,765,710 | B2 | 7/2014 | Sofia et al. |
| 8,772,474 | B2 | 7/2014 | Beigelman et al. |
| 8,802,840 | B2 | 8/2014 | Francom et al. |
| 8,815,829 | B2 | 8/2014 | Schinazi et al. |
| 8,816,074 | B2 | 8/2014 | Chu et al. |
| 8,841,275 | B2 | 9/2014 | Du et al. |
| 8,846,638 | B2 | 9/2014 | Or et al. |
| 8,846,896 | B2 | 9/2014 | Serebryany et al. |
| 8,853,171 | B2 | 10/2014 | Butler et al. |
| 8,859,595 | B2 | 10/2014 | Coats et al. |
| 8,859,756 | B2 | 10/2014 | Ross et al. |
| 8,871,737 | B2 | 10/2014 | Smith et al. |
| 8,871,785 | B2 | 10/2014 | Boojamra et al. |
| 8,877,731 | B2 | 11/2014 | Beigelman et al. |
| 8,877,733 | B2 | 11/2014 | Cho et al. |
| 8,889,159 | B2 | 11/2014 | Cleary et al. |
| 8,889,701 | B1 | 11/2014 | Ivachtchenko et al. |
| 8,895,531 | B2 | 11/2014 | Shi |
| 8,895,723 | B2 | 11/2014 | Serebryany et al. |
| 8,906,880 | B2 | 12/2014 | Du et al. |
| 8,912,321 | B2 | 12/2014 | Axt et al. |
| 8,921,384 | B2 | 12/2014 | Chu |
| 8,927,513 | B2 | 1/2015 | Manoharan et al. |
| 8,933,052 | B2 | 1/2015 | Jonckers et al. |
| 8,946,244 | B2 | 2/2015 | Chu et al. |
| 8,951,985 | B2 | 2/2015 | Surleraux et al. |
| 8,957,045 | B2 | 2/2015 | Sofia et al. |
| 8,957,046 | B2 | 2/2015 | Du et al. |
| 8,980,865 | B2 | 3/2015 | Wang et al. |
| 9,012,427 | B2 | 4/2015 | Blatt et al. |
| 9,012,428 | B2 | 4/2015 | Jonckers et al. |
| 9,045,520 | B2 | 6/2015 | Chun et al. |
| 9,061,041 | B2 | 6/2015 | Girijavallabhan et al. |
| 9,085,573 | B2 | 7/2015 | Du et al. |
| 9,085,599 | B2 | 7/2015 | Or et al. |
| 9,090,642 | B2 | 7/2015 | Cho et al. |
| 9,109,001 | B2 | 8/2015 | Parsy et al. |
| 9,139,604 | B2 | 9/2015 | Boojamra et al. |
| 9,156,872 | B2 | 10/2015 | Girijavallabhan et al. |
| 9,173,893 | B2 | 11/2015 | Cho et al. |
| 9,187,515 | B2 | 11/2015 | Mayes et al. |
| 9,192,621 | B2 | 11/2015 | Mayes et al. |
| 9,206,217 | B2 | 12/2015 | Ross et al. |
| 9,211,300 | B2 | 12/2015 | Mayes et al. |
| 9,243,025 | B2 | 1/2016 | Surleraux et al. |
| 9,249,174 | B2 | 2/2016 | Beigelman et al. |
| 9,284,342 | B2 | 3/2016 | Ross et al. |
| 9,339,541 | B2 | 5/2016 | Dousson et al. |
| 9,351,989 | B2 | 5/2016 | McGuigan et al. |
| 9,403,863 | B2 | 8/2016 | Surleraux et al. |
| 9,408,863 | B2 | 8/2016 | Verma et al. |
| 9,447,132 | B2 | 9/2016 | Deshpande et al. |
| 9,487,544 | B2 | 11/2016 | Cho et al. |
| 9,598,457 | B2 | 3/2017 | Smith et al. |
| 9,603,863 | B2 | 3/2017 | Blatt et al. |
| 9,603,864 | B2 | 3/2017 | Blatt et al. |
| 9,637,512 | B2 | 5/2017 | Chun et al. |
| 9,758,544 | B2 | 9/2017 | Beigelman et al. |
| 9,815,864 | B2 | 11/2017 | Beigelman et al. |
| 9,822,137 | B2 | 11/2017 | Dehaen et al. |
| 9,890,188 | B2 | 2/2018 | Wang et al. |
| 10,005,810 | B2 | 6/2018 | McGuigan et al. |
| 10,287,311 | B2 | 5/2019 | Clark |
| 10,577,359 | B2 | 3/2020 | Chun et al. |
| 11,642,361 | B2 | 5/2023 | Sofia et al. |
| 2002/0045599 | A1 | 4/2002 | Arimilli et al. |
| 2002/0058635 | A1 | 5/2002 | Averett |
| 2003/0087873 | A1 | 5/2003 | Stuyver et al. |
| 2004/0063658 | A1 | 4/2004 | Roberts et al. |
| 2004/0229839 | A1 | 11/2004 | Babu et al. |
| 2004/0259934 | A1 | 12/2004 | Olsen et al. |
| 2005/0009737 | A1 | 1/2005 | Clark |
| 2005/0038240 | A1 | 2/2005 | Connolly et al. |

(56) References Cited

U.S. PATENT DOCUMENTS

| | | | | |
|---|---|---|---|---|
| 2005/0203044 | A1 | 9/2005 | Zinnen | |
| 2006/0122146 | A1 | 6/2006 | Chun et al. | |
| 2006/0199783 | A1 | 9/2006 | Wang et al. | |
| 2007/0265222 | A1 | 11/2007 | MacCoss et al. | |
| 2008/0207554 | A1 | 8/2008 | Beigelman et al. | |
| 2008/0286230 | A1 | 11/2008 | Sommadossi et al. | |
| 2009/0156545 | A1 | 6/2009 | Hostetler et al. | |
| 2009/0176732 | A1 | 7/2009 | Beigelman et al. | |
| 2009/0181921 | A1 | 7/2009 | Blatt et al. | |
| 2009/0318380 | A1 | 12/2009 | Sofia et al. | |
| 2010/0137576 | A1 | 6/2010 | Stec et al. | |
| 2010/0240604 | A1 | 9/2010 | Beigelman et al. | |
| 2010/0249068 | A1 | 9/2010 | Beigelman et al. | |
| 2010/0279969 | A1 | 11/2010 | Schinazi et al. | |
| 2010/0286083 | A1 | 11/2010 | Bao et al. | |
| 2010/0331397 | A1 | 12/2010 | Beigelman et al. | |
| 2011/0015146 | A1 | 1/2011 | Sofia et al. | |
| 2011/0091943 | A1 | 4/2011 | Gallou et al. | |
| 2011/0223659 | A1 | 9/2011 | Scholl et al. | |
| 2011/0257121 | A1 | 10/2011 | Chang et al. | |
| 2012/0070411 | A1 | 3/2012 | Beigelman et al. | |
| 2012/0135951 | A1 | 5/2012 | Schinazi et al. | |
| 2012/0245335 | A1 | 9/2012 | Clark | |
| 2013/0064794 | A1 | 3/2013 | Surleraux et al. | |
| 2013/0225636 | A1 | 8/2013 | Roberts et al. | |
| 2013/0244966 | A1 | 9/2013 | Milne et al. | |
| 2013/0273005 | A1 | 10/2013 | Delaney et al. | |
| 2013/0315868 | A1 | 11/2013 | Mayes et al. | |
| 2014/0038916 | A1 | 2/2014 | Wang et al. | |
| 2014/0066395 | A1 | 3/2014 | Cho et al. | |
| 2014/0112886 | A1 | 4/2014 | Moussa et al. | |
| 2014/0187511 | A1 | 7/2014 | Du et al. | |
| 2014/0212382 | A1 | 7/2014 | Schinazi et al. | |
| 2014/0235566 | A1 | 8/2014 | Amblard et al. | |
| 2015/0011481 | A1 | 1/2015 | Vilchez et al. | |
| 2015/0011497 | A1 | 1/2015 | Beigelman et al. | |
| 2015/0057243 | A1 | 2/2015 | Zhou et al. | |
| 2015/0105341 | A1 | 4/2015 | Beigelman et al. | |
| 2015/0150897 | A1 | 6/2015 | Denning et al. | |
| 2015/0183818 | A1 | 7/2015 | Tran et al. | |
| 2016/0002281 | A1 | 1/2016 | Mayes et al. | |
| 2016/0220595 | A1 | 8/2016 | Liotta et al. | |
| 2016/0257706 | A1 | 9/2016 | Sommadossi et al. | |
| 2016/0271162 | A1 | 9/2016 | Moussa et al. | |
| 2017/0022242 | A1 | 1/2017 | Herdewyn et al. | |
| 2017/0029456 | A1 | 2/2017 | Dousson et al. | |
| 2017/0275322 | A1 | 9/2017 | Oinho et al. | |
| 2018/0009836 | A1 | 1/2018 | Sommadossi et al. | |
| 2018/0215776 | A1* | 8/2018 | Moussa | A61K 45/06 |
| 2019/0153017 | A1 | 5/2019 | Sommadossi et al. | |
| 2019/0201433 | A1 | 7/2019 | Sommadossi et al. | |
| 2019/0255085 | A1 | 8/2019 | Clarke et al. | |
| 2020/0087339 | A1 | 3/2020 | Moussa et al. | |

FOREIGN PATENT DOCUMENTS

| | | | |
|---|---|---|---|
| CN | 103980332 | A | 8/2014 |
| CN | 105646629 | A | 6/2016 |
| CN | 106188192 | A | 12/2016 |
| EP | 547008 | A1 | 6/1993 |
| EP | 398231 | B1 | 7/1997 |
| WO | WO 1998/16184 | A2 | 4/1998 |
| WO | WO 2001/009143 | A1 | 2/2001 |
| WO | WO 2001/90121 | A2 | 11/2001 |
| WO | WO 2001/92282 | A2 | 12/2001 |
| WO | WO 2002/32920 | A2 | 4/2002 |
| WO | WO 2003/033508 | A1 | 4/2003 |
| WO | WO 2003/039523 | A2 | 5/2003 |
| WO | WO 2003/062256 | A1 | 7/2003 |
| WO | WO 2003/093290 | A2 | 11/2003 |
| WO | WO 2004/002999 | A2 | 1/2004 |
| WO | WO 2004/003000 | A2 | 1/2004 |
| WO | WO 2004/014312 | A2 | 2/2004 |
| WO | WO 2004/052906 | A2 | 6/2004 |
| WO | WO 2004/074350 | A2 | 9/2004 |
| WO | WO 2004/091499 | A2 | 10/2004 |
| WO | WO 2004/106356 | A1 | 12/2004 |
| WO | WO 2005/000864 | A1 | 1/2005 |
| WO | WO 2005/003147 | A2 | 1/2005 |
| WO | WO 2005/020884 | A2 | 3/2005 |
| WO | WO 2005/021568 | A2 | 3/2005 |
| WO | WO 2005/084192 | A2 | 9/2005 |
| WO | WO 2005/090370 | A1 | 9/2005 |
| WO | WO 2006/012078 | A2 | 2/2006 |
| WO | WO 2006/063149 | A1 | 6/2006 |
| WO | WO 2006/063717 | A2 | 7/2006 |
| WO | WO 2006/094347 | A1 | 9/2006 |
| WO | WO 2006/102533 | A2 | 9/2006 |
| WO | WO 2006/121820 | A1 | 11/2006 |
| WO | WO 2006/130217 | A2 | 12/2006 |
| WO | WO 2007/022073 | A2 | 2/2007 |
| WO | WO 2007/112028 | A2 | 10/2007 |
| WO | WO 2007/130783 | A1 | 11/2007 |
| WO | WO 2008/012555 | A2 | 1/2008 |
| WO | WO 2008/048128 | A1 | 4/2008 |
| WO | WO 2008/062206 | A2 | 5/2008 |
| WO | WO 2008/095040 | A2 | 10/2008 |
| WO | WO 2009/001097 | A2 | 12/2008 |
| WO | WO 2009/003042 | A1 | 12/2008 |
| WO | WO 2009/067409 | A1 | 5/2009 |
| WO | WO 2009/086192 | A1 | 7/2009 |
| WO | WO 2009/086201 | A1 | 7/2009 |
| WO | WO 2009/129120 | A2 | 10/2009 |
| WO | WO 2010/081082 | A2 | 7/2010 |
| WO | WO 2010/091386 | A2 | 8/2010 |
| WO | WO 2010/108135 | A1 | 9/2010 |
| WO | WO 2010/145778 | | 12/2010 |
| WO | WO 2011/005595 | A1 | 1/2011 |
| WO | WO 2011/005860 | A2 | 1/2011 |
| WO | WO 2012/041965 | A1 | 4/2012 |
| WO | WO 2012/048013 | A2 | 4/2012 |
| WO | WO 2012/092484 | A2 | 7/2012 |
| WO | WO 2012/125900 | A1 | 9/2012 |
| WO | WO 2012/154321 | A1 | 11/2012 |
| WO | WO 2012/158811 | A2 | 11/2012 |
| WO | WO 2013/009737 | A1 | 1/2013 |
| WO | WO 2013/019874 | A1 | 2/2013 |
| WO | WO 2013/039855 | A1 | 3/2013 |
| WO | WO 2013/039920 | A1 | 3/2013 |
| WO | WO 2013/044030 | A1 | 3/2013 |
| WO | WO 2013/059735 | A1 | 4/2013 |
| WO | WO 2013/090420 | A2 | 6/2013 |
| WO | WO 2013/096680 | A1 | 6/2013 |
| WO | WO 2013/142125 | A1 | 9/2013 |
| WO | WO 2013/142157 | A1 | 9/2013 |
| WO | WO 2013/142159 | A1 | 9/2013 |
| WO | WO 2013/151975 | A1 | 10/2013 |
| WO | WO 2013/177219 | A1 | 11/2013 |
| WO | WO 2013/187978 | A1 | 12/2013 |
| WO | WO 2014/008236 | A1 | 1/2014 |
| WO | WO 2014/047117 | A1 | 3/2014 |
| WO | WO 2014/052638 | A1 | 4/2014 |
| WO | WO 2014/063019 | A1 | 4/2014 |
| WO | WO 2014/076490 | A1 | 5/2014 |
| WO | WO 2014/082935 | A1 | 6/2014 |
| WO | WO 2014/100498 | A1 | 6/2014 |
| WO | WO 2014/100505 | A1 | 6/2014 |
| WO | WO 2014/120981 | A1 | 8/2014 |
| WO | WO 2014/124430 | A1 | 8/2014 |
| WO | WO 2014/137930 | A1 | 9/2014 |
| WO | WO 2014/169278 | A1 | 10/2014 |
| WO | WO 2014/169280 | A2 | 10/2014 |
| WO | WO 2014/209979 | A1 | 12/2014 |
| WO | WO 2015/038596 | A1 | 3/2015 |
| WO | WO 2015/053662 | A1 | 4/2015 |
| WO | WO 2015/081133 | A2 | 6/2015 |
| WO | WO 2015/095305 | A1 | 6/2015 |
| WO | WO 2015/158913 | A1 | 10/2015 |
| WO | WO 2016/041877 | A1 | 3/2016 |
| WO | WO 2016/100441 | A1 | 6/2016 |
| WO | WO 2016/100569 | A1 | 6/2016 |
| WO | WO 2016/144918 | A1 | 9/2016 |
| WO | WO 2016/145142 | A1 | 9/2016 |
| WO | WO-2017/012539 | A1 | 1/2017 |

(56) References Cited

FOREIGN PATENT DOCUMENTS

WO WO 2018/013937 A1 1/2018
WO WO 2018/048937 A1 3/2018
WO WO 2019/200005 A1 10/2019

OTHER PUBLICATIONS

Ahn et al. "Biochemical characterization of a recombinant SARS coronavirus nsp12 RNA-dependent RNA polymerase capable of copying viral RNA templates", Arch Virol., 157, 2095-2104, 2012.
Atea Pharmaceuticals Introduces New Strategic Clinical Development Program for AT-527 in COVID-19; Dec. 14, 2021.
Atea Pharmaceuticals Provides Update and Topline Results for Phase 2 MOONSONG Trial Evaluating AT-527 in the Outpatient Setting, Oct. 19, 2021.
Atea Pharmaceuticals Reports Nonclinical Bemnifosbuvir (AT-527) Toxicology Data at Society of Toxicology 61st Annual Meeting; Mar. 28, 2022.
Atea Pharmaceuticals to Present at the 2022 Jefferies Healthcare Conference; Jun. 1, 2022.
Belikov, V.G. Pharmaceutical Chemistry, Fourth Edition, revised textbook, 2007, Moscow, 30 "MEDpress-inform", pp. 27-29, 2007.
Berge, M.S. et al. "Pharmaceutical Salts" Journal of Pharmaceutical Sciences, 66, 1, 1977.
Berliba et al. "Safety, Pharmacokinetics, and Antiviral Activity of AT-527, a Novel Purine Nucleotide Prodrug, in Hepatitis C Virus-Infected Subjects with or without Cirrhosis," Antimicrobial Agents and Chemotherapy, vol. 63, Issue 12, Dec. 2019.
Bukrinskaya A.G. Virology—M.: Medicine, p. 152, lines 12-15 from the top, 1986.
Chang, W. et al. "Discovery of PSI-353661, a Novel Purine Nucleotide Prodrug for the Treatment of HCV Infection" ACS Med Chem Lett., 2, 130, 2011.
Cretton-Scott, E. et al. "In vitro antiviral activity and pharmacology of idx184, a novel and potent inhibitor of HCV replication" (Abstract 588) J. Hepatol., 48, Supplement 2, S220, 2008.
Declaration of Alexander M. Klibanov, Ph.D. (PGR2023-00046—Exhibit No. 15) Filed Aug. 6, 2023.
Ershov, F.I. et al. Ministry of Health and Social Development of The Russian Federation Federal State Budgetary Institution "Scientific Center on Expertise of Medical Application Products" Guidelines on Preclinical Trials of Medicinal Products, Moscow, 2012.
Freeman et al. 2-amino-9(3-azido-2,3-dideoxy-β-D-erythro-pentofuranosy1)-6-Substituted-9H-Purines: Synthesis and Anti-HIV Activity. Bioorganic and Medicinal Chemistry, 3(4): 447-448, 1995.
Gao et al. "Structure of the RNA-dependent RNA polymerase from COVID-19 virus", Science, 368(6492), 779-782, 2020.
Good et al. "AT-527, a Double Prodrug of a Guanosine Nucleotide Analog, Is a Potent Inhibitor of SARS-CoV-2 In Vitro and a Promising Oral Antiviral for Treatment of COVID19" Antimicrobial Agents and Chemotherapy, vol. 65, Issue 4, Apr. 2021.
Good et al. "Preclinical evaluation of AT-527, a novel guanosine nucleotide prodrug with potent, pan-genotypic activity against hepatitis C virus," PLOS One, https://doi.org/10.1371/journal.pone.0227104, Jan. 8, 2020.
Good, S. et al. "AT-337, AT-511, and its Salt Form, AT-527: Novel Potent and Selective Pan-genotypic Purine Nucleotide Prodrug Inhibitors of HCV Polymerase" presented at the AASLD 2017 Liver Meeting; Washington, D.C., Oct. 20-Oct. 24, 2017.
Herman, B. et al. "Substrate mimicry: HIV-1 reverse transcriptase recognizes 6-modified-30-azido-20,30-dideoxyguanosine-50-triphosphates as adenosine analogs" Nucleic Acids Research, 40, 381, 2012.
Hirayama, Noriaki Handbook for Producing Organic Compound Crystals, pp. 17-23, 37-40, 45-51, and 57-65 and English partial translation, 2008.
Hoffman, M. et al. "SARS-CoV-2 Cell Entry Depends on ACE2 and TMPRSS2 and Is Blocked by a Clinically Proven Protease Inhibitor", Cell, 181(2), 271-280, 2020.
Huang et al. "Impact of solid state properties on developability assessment of drug candidates" Advanced Drug Delivery Reviews, 56, 321, 2004.
Huang et al. "Clinical features of patients infected with 2019 novel coronavirus in Wuhan, China", Lancet, 395(10223), 497-506, 2020.
Krausslich et al. Antiviral Strategies, Springer-Verlag Berlin Heidelberg, pp. 1-24, Dec. 3, 2009.
Lau et al. "Severe acute respiratory syndrome coronavirus-like virus in Chinese horseshoe bats", PNAS, 102(39), 14040-14045, 2005.
Luan et al. "Spike protein recognition of mammalian ACE2 predicts the host range and an optimized ACE2 for SARS-CoV-2 infection", Biochem. Biophys. Res. Commun., 526(1), 165-169, 2020.
Luo, Shouqi et al. 4793: Lack of Reproductive and Developmental Toxicity for AT-527 (Bemnifosbuvir), an Oral Purine Nucleotide Prodrug for COVID-19 Infection; Mar. 27-31, 2022.
Luo, Shouqi et al. 4794: Characterization of the Toxicity Profile of AT-527 (Bemnifosbuvir), a Novel Guanosine Nucleotide Prodrug with Antiviral Activity for COVID-19 Infection; Mar. 27-31, 2022.
Mashkovsky, M.D. "Medicines, a guide for doctors", part. 1, Moscow, "Medicine", p. 8, 1993.
Mcguigan, C. et al. "Design, synthesis and evaluation of a novel double pro-drug: INX-08189. A new clinical candidate for hepatitis C virus" Bioorganic & Medicinal Chemistry Letters, 20, 4850, 2010.
Mcguigan, C. et al. "Dual pro-drugs of 2'-C-methyl guanosine monophosphate as potent and selective inhibitors of hepatitis C virus" Bioorganic & Medicinal Chemistry Letters, 21, 6007, 2011.
Murakami, E. et al. "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem, 54, 5902, 2011.
Musso, Didier et al. Zika Virus Clinical Microbiology Reviews, American Society for Microbiology, vol. 29, No. 3, 489-524, Jul. 2016.
Nguyen, Lien et al. International Journal of Biomedical Science: Chiral Drugs: An Overview, 20, 85-100, Jun. 2, 2006.
Petition for Post Grant Review of U.S. Pat. No. 11,642,361 (PGR2023-00046—Paper No. 1) Filed Aug. 7, 2023.
Poordad et al. "Daclatasvir with Sofosbuvir and Ribavirin for Hepatitis C Virus Infection with Advanced Cirrhosis or Post-Liver Transplantation Recurrence" Hepatology, 63, 1493, 2016.
Pradere, U. et al. "Synthesis of 5'-Methylene-Phosphonate Furanonucleoside Prodrugs: Application to D-2'-Deoxy-2'-α-fluoro-2'-B-C-methyl Nucleosides" Organic Letters, 14, 4426, 2012.
Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters, 20, 7376, 2010.
Rest et al. "SARS associated coronavirus has a recombinant polymerase and coronaviruses have a history of host-shifting", Infect Genet Evol., 3(3), 219-225, 2003.
Schoeman and Fielding, "Coronavirus envelope protein: current knowledge", Virology, 16(69), 1-22, 2019.
Serajuddin, A.T.M "Salt formation to improve drug solubility" Advanced Drug Delivery Reviews, 59, 603, 2007.
Shannon, Ashleigh et al. A dual mechanism of action of AT-527 against SARS-CoV-2 polymerase, Nature Communications, 13:621, Feb. 2, 2022.
Sofia, M.J. "Nucleotide Prodrugs for HCV Therapy," Antiviral Chemistry & Chemotherapy, 22, 23, 2011.
Stahl et al. "Handbook of Pharmaceutical Salts Properties, Selection, and Use," International Union of Pure and Applied Chemistry (IUPAC), Chapters 6 and 7, 2002.
Subissi et al. "One severe acute respiratory syndrome coronavirus protein complex integrates processive RNA polymerase and exonuclease activities", Proc. Natl. Acad. Sci., 111(37), E3900-E3909, 2014.
Tao, S., Zhou, L., Zhang, H., Zhou, S., Amiralaei, S., Shelton, J.R., Coats, S.J., Schinazi, R.F.: Comparison of Three 2'-C-Methyl Guanosine Prodrugs for Hepatitis C including a Novel $^{2}$-D-2'-C-Me-2,6-Diaminopurine Ribonucleoside Phosphoramidate (RS-1389): Interspe-

(56) References Cited

OTHER PUBLICATIONS cies Hepatocyte and Human Cardiomyocyte Metabolism Profiles. The Liver Meeting 2014. Boston, MA, USA. Nov. 6-11, 2014.
Wu, Jim Zhen et al. "Ribavirin, viramidine and adenosine-deaminase-catalysed drug activation: implication for nucleoside prodrugs design," Journal of Antimicrobial Chemotherapy, 52, 543-546, 2003.
Yang et al. "Targeting the Endocytic Pathway and Autophagy Process as a Novel Therapeutic Strategy in COVID-19", Int. J. Biol. Sci., 16(10), 1724-1731, 2020.
Yoon et al. "Design, Synthesis, and Anti-RNA Virus of 6'-Fluorinated- Aristeromycin Analogues," Journal of Medicine Chemistry, vol. 62, p. 6346-6362, Jun. 7, 2019.
Zhang et al. "Synthesis and evaluation of 30-azido-20,30-dideoxypurine nucleosides as inhibitors of human immunodeficiency virus" Bioorganic and Medicinal Chemistry Letters, 20, 60, 2010.
Zhou et al. "A pneumonia outbreak associated with a new coronavirus of probable bat origin", Nature, 579, 270, 2020.
Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem, 58, 3445, 2015.
Zhou, X. et al. "A Phase la Study of AT-527, a Novel Pan-Genotypic Purine Nucleotide Prodrug Inhibitor of Hepatitis C Virus (HCV)" presented at The Liver Meeting 2017; Washington, D.C., Oct. 23, 2017.
Zhou, X. et al. "AT-527, a pan-genotypic purine nucleotide prodrug, exhibits potent antiviral activity in subjects with chronic hepatitis C" presented at The International Liver Congress 2018; Paris, France, Apr. 13, 2018.
U.S. Pat. No. 9,828,410 B2, U.S. Appl. No. 15/063,461, Sommadossi et al., Nov. 28, 2017.
U.S. Pat. No. 10,000,523 B2, U.S. Appl. No. 15/782,628, Sommadossi et al., Jun. 19, 2018.
U.S. Pat. No. 10,005,811 B2, U.S. Appl. No. 15/782,638, Sommadossi et al., Jun. 26, 2018.
U.S. Pat. No. 10,202,412 B2, U.S. Appl. No. 15/645,701, Sommadossi et al., Feb. 12, 2019.
U.S. Pat. No. 10,239,911 B2, U.S. Appl. No. 16/001,549, Sommadossi et al., Mar. 26, 2019.
U.S. Pat. No. 10,519,186 B2, U.S. Appl. No. 15/885,630, Moussa et al., Dec. 31, 2019.
U.S. Pat. No. 10,815,266 B2, U.S. Appl. No. 16/278,621, Sommadossi et al., Oct. 27, 2020.
U.S. Pat. No. 10,870,672 B2, U.S. Appl. No. 16/900,397, Sommadossi et al., Dec. 22, 2020.
U.S. Pat. No. 10,870,673 B2, U.S. Appl. No. 16/918,898, Sommadossi et al., Dec. 22, 2020.
U.S. Pat. No. 10,874,687 B2, U.S. Appl. No. 17/017,443, Sommadossi et al., Dec. 29, 2020.
U.S. Pat. No. 10,875,885 B2, U.S. Appl. No. 16/918,914, Sommadossi et al., Dec. 29, 2020.
U.S. Pat. No. 10,894,804 B2, U.S. Appl. No. 16/918,918, Moussa et al., Jan. 19, 2021.
U.S. Pat. No. 10,906,928 B2, U.S. Appl. No. 16/687,136, Moussa et al., Feb. 2, 2021.
U.S. Pat. No. 10,946,033 B2, U.S. Appl. No. 16/293,423, Sommadossi et al., Mar. 16, 2021.
U.S. Pat. No. 11,690,860 B2, U.S. Appl. No. 17/065,149, Sommadossi et al., Jul. 4, 2023.
U.S. Pat. No. 11,707,480 B2, U.S. Appl. No. 17/094,541, Sommadossi et al., Jul. 25, 2023.
U.S. Pat. No. 11,738,038 B2, U.S. Appl. No. 17/306,674, Sommadossi et al., Aug. 29, 2023.
U.S. Pat. No. 11,813,278 B2, U.S. Appl. No. 17/184,445, Sommadossi et al., Nov. 14, 2023.
U.S. Pat. No. 11,975,016 B2, U.S. Appl. No. 17/482,224, Sommadossi et al., May 7, 2024.
U.S. Pat. No. 12,006,340 B2, U.S. Appl. No. 18/100,448, Moussa et al., Jun. 11, 2024.
U.S. Pat. No. 12,084,473 B2, U.S. Appl. No. 18/100,452, Sommadossi et al., Sep. 10, 2024.
US 2023/0049294 A1, U.S. Appl. No. 17/971,318, Moussa et al., Feb. 16, 2023.
US 2023/0331751 A1, U.S. Appl. No. 18/111,316, Moussa et al., Oct. 19, 2023.
US 2023/0364121 A1, U.S. Appl. No. 18/132,300, Sommadossi et al., Nov. 16, 2023.
US 2024/0148770 A1, U.S. Appl. No. 18/540,608, Sommadossi et al., May 9, 2024.
US 2024/0226131 A1, U.S. Appl. No. 18/592,037, Sommadossi et al., Jul. 11, 2024.
US 2024/0238324 A1, U.S. Appl. No. 18/225,452, Sommadossi et al., Jul. 18, 2024.
US 2024/0261316 A1, U.S. Appl. No. 18/368,959, Sommadossi et al., Aug. 8, 2024.
U.S. Appl. No. 18/739,149, Moussa et al., filed Jun. 10, 2024.
U.S. Appl. No. 18/828,972, Sommadossi et al., filed Sep. 9, 2024.
Healy, A.M. et al. "Pharmaceutical solvates, hydrates and amorphous forms: A special emphasis on cocrystals," Advanced Drug Delivery Reviews. 117, 25-46, 2017.
International Search Report and Written Opinion of PCT/US22/13953, 8 pages, mailed Apr. 6, 2022.
U.S. Pat. No. 12,458,656-B2, Nov. 4, 2025, Sommadossi et al., U.S. Appl. No. 19/215,054.
U.S. Pat. No. 12,551,499, Feb. 17, 2026, Sommadossi et al., U.S. Appl. No. 18/368,959.
US-2025/0243235-A1, Jul. 31, 2025, Sommadossi et al., U.S. Appl. No. 18/828,972.
US-2026/0035404-A1, Feb. 5, 2026, Moussa, U.S. Appl. No. 19/350,713.
U.S. Appl. No. 19/350,774, Sommadossi et al., filed Oct. 6, 2025.

* cited by examiner

ADVANTAGEOUS MORPHIC FORM OF AT-527 HEMI-SULFATE SALT

CROSS-REFERENCE TO RELATED APPLICATION

This application is a continuation of International Application No. PCT/US2022/013953, filed in the U.S. Receiving Office on Jan. 26, 2022, which claims the benefit of U.S. Provisional Application 63/141,789 which was filed on Jan. 26, 2021. The entirety of each of these applications is hereby incorporated by reference for all purposes.

FIELD OF THE INVENTION

The present invention provides an advantageous isolated morphic form of a hemi-sulfate salt of isopropyl ((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate (AT-527) that can be used in a solid dosage form in a pharmaceutical composition or as a manufacturing intermediate for a pharmaceutical composition, including a spray-dried dosage form.

BACKGROUND OF THE INVENTION

U.S. Pat. Nos. 9,828,410; 10,000,523; 10,005,811; 10,239,911; 10,519,186; 10,815,266; 10,870,672; 10,870,673; 10,875,885 and PCT Applications PCT/US16/21276 (WO2016/144918); PCT/US2017/50323 (WO 2018/048937); PCT/US18/16301 (WO2018/144640); and PCT/US2019/26837 (WO 2019/200005) assigned to Atea Pharmaceuticals disclose Compound A (also known as AT-527) and Compound B. Compound A is the hemisulfate salt of Compound B and has been shown to have improved therapeutic effects over Compound B. Compound A has been found to disproportionately concentrate in the lung and the liver which are therapeutic targets for certain viral diseases. Additionally, Compound A has an advantageous safety profile, with no drug related serious adverse events observed in clinical trials.

Compound A

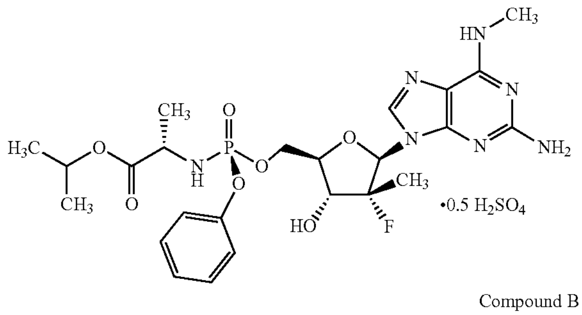

Compound B

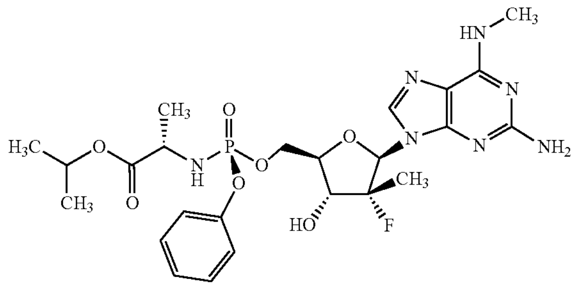

U.S. Pat. No. 10,874,687 to Atea Pharmaceuticals describes the use of Compound A and Compound B to treat SARS-CoV-2, the virus that causes COVID-19. It was surprisingly discovered that Compound A is potent against SARS-CoV-2. Compound A, which is an orally administered drug, has been studied in a global Phase 2 trial for moderate COVID-19. The oral administration is especially advantageous for facilitating broad patient access and compliance. Compound A may represent an advance in the global fight against COVID-19, either alone or in combination with another active agent.

Compound A and Compound B also have activity against HCV (see for instance U.S. Pat. No. 10,906,928). Compound A completed a Phase 2 clinical trial for patients infected with HCV. The multiple part study evaluated the effect of single and multiple doses of Compound A in healthy subjects, non-cirrhotic HCV-infected patients, and cirrhotic HCV-infected patients. Compound A induced significant antiviral reduction when administered in all HCV-infected cohorts tested (Good et al. *PLoS ONE* 15(1): e0227104).

Compound A and Compound B have also been shown to be active against positive strand RNA viruses (see for instance U.S. Pat. No. 10,946,033).

Given the importance of Compound A for the therapeutic treatment of humans infected with or at risk of infection with a virus susceptible to Compound A, such as a positive strand RNA viral disease, including SARS-CoV-2 and HCV, it would be useful to identify an improved pharmaceutical formulations and methods of their manufacture.

SUMMARY OF THE INVENTION

It has been discovered that Compound A (the hemi-sulfate salt of isopropyl ((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy)phosphoryl)-L-alaninate, also known at AT-527) can be prepared in a highly purified, advantageous morphic form.

Compound A

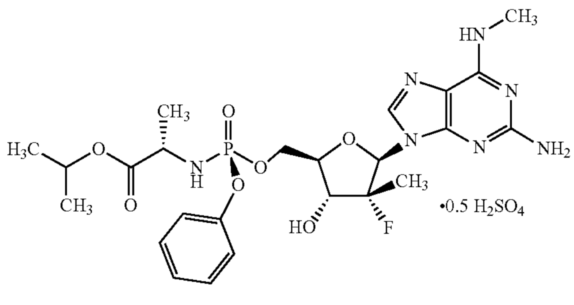

This highly purified, advantageous morphic form is referred to as "Form III". Form III is a form of Compound A that exhibits superior crystallinity compared to other forms. Importantly, Compound A Form III possesses a high dissolution rate relative to amorphous Compound A. The dissolution rates described herein were evaluated according to the method described in Example 5, which used dilute (0.1 N) HCl in vitro.

As non-limiting illustrations, Example 5 shows that while tablets produced from spray-dried amorphous Compound A required 60 minutes to reach about 99% dissolution of Compound A, the tablets produced using the superior Form III reached about 99% dissolution of Compound A within 20 minutes. Clinical results suggest that a faster dissolution rate leads to higher exposure and clinical efficacy. It is unusual that the highly crystalline Compound A Form III shows a higher dissolution rate than the amorphous form. This unusual characteristic leads to an improved pharmaceutical composition for medicinal therapy such as anti-viral therapy for a host, such as a human in need thereof.

Thus, the present invention includes a solid dosage form and pharmaceutical composition with superior properties that incorporates an effective amount of morphic Form III of Compound A, optionally in combination with one or more excipients and or one or more other components which may or may not be pharmaceutically active. In certain non-limiting embodiments, an effective amount of Compound A Form III is used in a solid dosage form for administration to a host in need thereof, such as a human. The solid dosage form that includes Compound A Form III exhibits an unexpectedly high dissolution rate relative to amorphous or spray-dried Compound A.

In another embodiment, Compound A Form III can be used as a high purity manufacturing intermediate of a pharmaceutical solid dosage form, including a spray-dried dispersion. The purity, crystallinity, and stability of Form III is advantageous for manufacturing. When measured by XRPD and HPLC-UV, Compound A Form III showed little or no decrease in chemical purity after one year under ambient conditions. Storage under conditions which accelerate degradation (40° C. and 75% RH) caused no measurable decrease in purity or generation of impurities after three months.

In certain non-limiting embodiments, Compound A Form III can be manufactured in large scale using for example, the procedures of Examples 3 or 4. As a non-limiting illustration, a large scale manufacture may in embodiments include the steps of slurrying the hemisulfate salt AT-527 in acetone, removing the acetone, slurrying in heptane and then drying. It has been found that these are superior conditions for producing Compound A Form III. When Compound A is slurried in acetone, it is broken up and partially solubilized in preparation for crystal formation. While acetone is a good solvent to prepare Compound A for crystallization, it is removed too quickly for good crystallization to occur. Therefore, the acetone is removed to form a cake to which heptane is added. It has been found that heptane is a superior solvent for crystallization of Compound A because it comes off slowly, facilitates the removal of solvent and allows optimal crystallization to Form III over time.

More specifically, the hemisulfate salt can be slurried in hot acetone, cooled and filtered to afford a wet cake, which is then slurried in cooled heptane, filtered and dried. In alternative embodiments, the heptane is replaced with another nonpolar solvent with similar properties. Non-limiting examples of nonpolar solvent include but are not limited to heptane (may be n-heptane or mixed heptanes), cyclohexane, hexane (which may be n-hexane or a mixture of hexanes), petroleum ether, octane, diethyl ether, methyl tert-butyl ether, dibutyl ether or other dialkyl ethers.

In another non-limiting embodiment, Compound A Form III is produced by the crystallization of Compound A in methanol and acetone, also as described in more detail herein. In certain non-limiting embodiments, Compound A Form III is produced by crystallizing Compound A in a mixture of methanol and acetone. A non-limiting embodiment of this process is in Example 2. In certain non-limiting embodiments, Compound A is dissolved in methanol and then acetone is slowly added and the mixture is heated. This is followed by cooling and filtering to isolate Form III.

Compound A Forms I-II and IV-V have also been prepared in addition to Form III and are also provided herein. Forms I-II and IV-V have more amorphous character compared to Form III (Example 2).

In one aspect, Compound A Form III is characterized by an XRPD pattern substantially similar to that set forth in FIG. 2. In certain non-limiting embodiments, Compound A Form III is characterized by an XRPD pattern comprising at least five, six, seven, eight, nine, or ten 2theta values selected from Table 2. In some aspects, Compound A Form III is characterized by an XRPD pattern comprising 2theta values of at least three, four, five, six or all seven peaks selected from 5.2±0.2°, 7.3±0.2°, 8.9±0.2°, 13.6±0.2°, 17.0±0.2°, 19.9±0.2°, and 21.8±0.2°. For example, Compound A Form III can be characterized by an XRPD pattern comprising 2theta values of at least or selected from 5.2±0.2°, 8.9±0.2°, 13.6±0.2°, 19.9±0.2°, and 21.8±0.2°. In another aspect, Form III is characterized by an XRPD pattern comprising the 2theta values of at least or selected from 5.2±0.2°, 8.9±0.2°, 19.9±0.2°, and 21.8±0.2°. In another non-limiting embodiment, Compound A Form III is characterized by an XRPD pattern comprising at least the 2theta values 5.2±0.2° and 21.8±0.2°. In another aspect, Compound A Form III is characterized by an XRPD pattern comprising at least the 2theta value 5.2±0.2°. In an alternative embodiment, the standard deviation is ±0.3° 2theta or ±0.4° 2theta.

Thus, the present invention provides an isolated morphic Form III of Compound A, pharmaceutical compositions comprising such morphic form, including solid dosage forms, and methods for treating viruses susceptible to Compound A Form III, such as positive strand RNA viral infections, including, SARS-CoV-2 and viruses from the Flaviviridae family such as HCV, Dengue Fever, West Nile Fever, Yellow Fever, and Zika virus that include administering an effective amount of the morphic Form III to treat a host such as a human in need thereof.

Compound A Form III is advantageously provided in a solid dosage pharmaceutical formulation. In certain embodiments, the formulation comprises at least about 400 mg, 450 mg, 500 mg, 550 mg, 600 mg, 650 mg, or 700 mg of Compound A Form III (when including both the nucleotide and the hemi-sulfate salt in the weight calculation). In certain embodiments the formulation comprises from about 500 mg to about 1,200 mg of Compound A. In certain embodiments the formulation comprises from about 300 mg to about 1,200 mg of Compound A. In certain embodiments the formulation comprises from about 400 mg to about 800 mg of Compound A. In certain embodiments the formulation comprises from about 500 mg to about 700 mg of Compound A. In certain embodiments, the formulation comprises at least about 600 mg of Compound A. When a dosage form herein refers to a milligram weight dose, it refers to the amount of Compound A (i.e., the weight of the hemi-sulfate salt and the nucleotide) unless otherwise specified to the contrary. For example, approximately 600 mg of Compound A is the equivalent of approximately 550 mg of Compound B.

In specific embodiments, the formulation is suitable for oral delivery, for example, a solid dosage form. In certain embodiments the solid dosage form that includes Compound A Form III is at least approximately 70, 75, 80, 85 or 90% dissolved in aqueous media (where, as used herein, refers to for example dilute HCl such as 0.1 N HCl) within 30 minutes. In certain embodiments the solid dosage form that includes Compound A Form III is greater than 90% dissolved in aqueous media within 20 minutes. In certain embodiments the solid dosage form includes Compound A Form III that is approximately 99% or more dissolved in aqueous media within 30 minutes. The high dissolution rate and high solubility of the solid dosage form is considered to lead to enhanced efficacy through increased bioavailability.

In other embodiments, Compound A Form III material is used in the preparation of a pharmaceutical composition, for example in a spray-dried solid dispersion or a granulo layered solid dispersion—due to its high purity and stability.

In another aspect of the present invention, an effective amount of Compound A Form III is administered to a host in need thereof to treat severe acute respiratory syndrome coronavirus 2 (SARS-CoV-2) or severe acute respiratory syndrome coronavirus (SARS-CoV). In another embodiment, an effective amount of Compound A Form III is administered to a host in need thereof infected with a virus of Flaviviridae family, including the hepatitis C virus, Dengue Fever, West Nile virus, Zika virus, Yellow Fever, or Japanese encephalitis.

The present invention thus includes at least the following features:

(a) Isolated crystalline morphic Form III of Compound A:

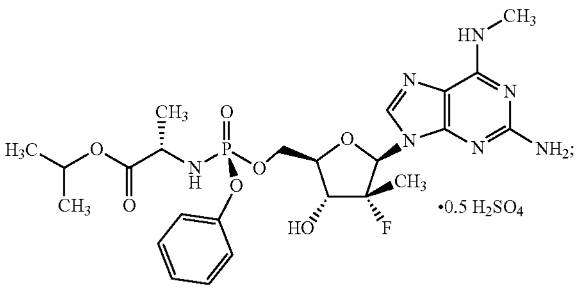 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

(b) Compound A Form III of (a) characterized by an XRPD pattern comprising the 2theta values selected from 5.2±0.4°, 7.3±0.4°, 8.9±0.4°, 13.6±0.4°, 17.0±10.4°, 19.9±0.4°, and 21.8±0.4°;

(c) Compound A Form III of (a) characterized by an XRPD pattern comprising at least six 2theta values selected from 5.2±0.4°, 7.3±0.4°, 8.9±0.4°, 13.6±0.4°, 17.0±0.4°, 19.9±0.4°, and 21.8±0.4°;

(d) Compound A Form III of (a) characterized by an XRPD pattern comprising at least five 2theta values selected from 5.2±0.4°, 7.3±0.4°, 8.9±0.4°, 13.6±0.4°, 17.0±0.4°, 19.9±0.4°, and 21.8±0.4°;

(e) Compound A Form III of (a) characterized by an XRPD pattern comprising at least four 2theta values selected from 5.2±0.4°, 7.3±0.4°, 8.9±0.4°, 13.6±0.4°, 17.0±0.4°, 19.9±0.4°, and 21.8±0.4°;

(f) Compound A Form III of (a) characterized by an XRPD pattern comprising at least three 2theta values selected from 5.2±0.4°, 7.3±0.4°, 8.9±0.4°, 13.6±0.4°, 17.0±0.4°, 19.9±0.4°, and 21.8±0.4°;

(g) Compound A Form III of (a) characterized by an XRPD pattern comprising at least two 2theta values selected from 5.2±0.4°, 7.3±0.4°, 8.9±0.4°, 13.6±0.4°, 17.0±0.4°, 19.9±0.4°, and 21.8±0.4°;

(h) Compound A Form III of (a) characterized by an XRPD pattern comprising at least one 2theta values selected from 5.2±0.4°, 7.3±0.4°, 8.9±0.4°, 13.6±0.4°, 17.0±0.4°, 19.9±0.4°, and 21.8±0.4°;

(i) Compound A Form III of (a) characterized by an XRPD pattern comprising at least two 2theta values selected from 5.2±0.4°, 8.9±0.4°, 19.9±0.4°, and 21.8±0.4°;

(j) Compound A Form III of (a) characterized by an XRPD pattern comprising at least one 2theta value selected from 5.2±0.4°, 8.9±0.4°, 19.9±0.4°, and 21.8±0.4°;

(k) Compound A Form III of (a) characterized by an XRPD pattern comprising at least the 2theta values 5.2±0.4° and 21.8±0.4°;

(l) Compound A Form III of (a) characterized by an XRPD pattern comprising at least the 2theta value 5.2±0.4°;

(m) Embodiment (b)-(l) wherein the standard deviation is ±0.3° 2theta;

(n) Embodiment (b)-(l) wherein the standard deviation is ±0.2° 2theta;

(o) A pharmaceutical composition comprising Compound A Form III of any one of embodiments (a)-(l) and a pharmaceutically acceptable carrier;

(p) The pharmaceutical composition of (o), in a solid dosage form suitable for oral administration;

(q) The pharmaceutical composition of (o) or (p) wherein the solid dosage form is a tablet;

(r) The pharmaceutical composition of (o) or (p) wherein the solid dosage form is a capsule;

(s) The pharmaceutical composition of (o)-(r) that delivers between about 600 and about 1,200 mg of Compound A Form III;

(t) The pharmaceutical composition of (o)-(r) that delivers between about 400 and about 1,000 mg of Compound A Form III;

(u) The pharmaceutical composition of (o)-(r) that delivers between about 500 and about 800 mg of Compound A Form III;

(v) The pharmaceutical compositions of (o)-(r) that delivers at least about 900 mg to about 1,200 of Compound A Form IIII;

(w) The pharmaceutical compositions of (o)-(r) that delivers at least about 500 mg of Compound A Form IIII;

(x) The pharmaceutical compositions of (o)-(r) that delivers at least about 600 mg of Compound A Form IIII;

(y) The pharmaceutical compositions of (o)-(r) that delivers at least about 700 mg or about 800 mg of Compound A Form IIII;

(z) The pharmaceutical compositions of (o)-(y) that is administered once a day;

(aa) The pharmaceutical compositions of (o)-(y) that is administered twice a day;

(bb) The pharmaceutical composition of (o)-(y) that is administered three times a day;

(cc) The pharmaceutical composition of (o)-(aa) that is prepared using Compound A Form III;

(dd) The pharmaceutical composition of (o)-(aa) wherein at least approximately 90% of the Compound A Form III dissolves within 30 minutes in aqueous solvent.

(ee) The pharmaceutical composition of embodiment (o)-(aa), wherein the dosage form with Compound A Form III is at least approximately 98% dissolved within 20 minutes.

(ff) The pharmaceutical composition of embodiment (o)-(aa), wherein the dosage form with Compound A Form III is at least approximately 99% dissolved within 20 minutes.

(gg) The pharmaceutical composition with Compound A Form III of embodiments (o)-(ff) that remains at least approximately 90% pure over 1 year at ambient temperature.

(hh) The pharmaceutical composition with Compound A Form III of embodiments (o)-(ff) that remains at least approximately 98% pure over 1 year at ambient temperature.

(ii) The pharmaceutical composition with Compound A Form III of embodiments (o)-(ff) that remains at least approximately 99% pure over 1 year at ambient temperature.

(jj) The pharmaceutical composition with Compound A Form III of embodiments (o)-(ii) that does not require refrigerated storage.

(kk) A spray-dried solid dispersion prepared using Compound A Form III;

(ll) A granular layered solid dispersion prepared using Compound A Form III;

(mm) A method to treat a Coronavirus such as SARS-CoV-2 comprising administering an effective amount of Compound A Form III of any one of embodiments (a)-(n), the pharmaceutical composition of embodiments (o)-(jj), or the solid dispersion of embodiments (kk) or (ll), optionally in a pharmaceutically acceptable carrier, to a host in need thereof;

(nn) A method to treat HCV comprising administering an effective amount of Compound A Form III of any one of embodiments (a)-(n), the pharmaceutical composition of embodiments (o)-(jj), or the solid dispersion of embodiments (kk) or (ll), optionally in a pharmaceutically acceptable carrier, to a host in need thereof;

(oo) A method to treat a virus of Flaviviridae family comprising administering an effective amount of the Compound A Form III of any one of embodiments (a)-(n), the pharmaceutical composition of embodiments (o)-(jj), or the solid dispersion of embodiments (kk) or (ll), optionally in a pharmaceutically acceptable carrier, to a host in need thereof;

(pp) The method of any one of embodiments (mm)-(oo) wherein the Compound A Form III is administered in a dosage form suitable for oral administration;

(qq) The method of any one of embodiments (mm)-(pp) wherein the host is a human;

(rr) The Compound A Form III of any one of embodiments (a)-(n), the pharmaceutical composition of embodiments (o)-(jj), or the solid dispersion of embodiments (kk) or (ll), optionally in a pharmaceutically acceptable carrier, for use to treat SARS-CoV-2 or SARS-CoV in a host in need thereof, (ss) The Compound A Form III of any one of embodiments (a)-(n), the pharmaceutical composition of embodiments (o)-(jj), or the solid dispersion of embodiments (kk) or (ll), optionally in a pharmaceutically acceptable carrier, for use to treat HCV in a host in need thereof, (tt) The Compound A Form III of any one of embodiments (a)-(n), the pharmaceutical composition of embodiments (o)-(jj), or the solid dispersion of embodiments (kk) or (ll), optionally in a pharmaceutically acceptable carrier, for use to treat a virus of Flaviviridae family in a host in need thereof;

(uu) Compound A Form III or the solid dispersion of any one of embodiments (rr)-(tt), wherein the host is a human.

(vv) The use of Compound A Form III of any one of embodiments (a)-(n), the pharmaceutical composition of embodiments (o)-(jj), or the solid dispersion of embodiments (kk) or (ll), optionally in a pharmaceutically acceptable carrier, in the manufacture of a medicament for the treatment of SARS-CoV-2 or SARS-CoV in a host in need thereof, (ww) The use of Compound A Form III of any one of embodiments (a)-(n), the pharmaceutical composition of embodiments (o)-(jj), or the solid dispersion of embodiments (kk) or (ll), optionally in a pharmaceutically acceptable carrier, in the manufacture of a medicament for the treatment of HCV in a host in need thereof;

(xx) The use of Compound A Form III of any one of embodiments (a)-(n), the pharmaceutical composition of embodiments (o)-(jj), or the solid dispersion of embodiments (kk) or (ll), optionally in a pharmaceutically acceptable carrier, in the manufacture of a medicament for the treatment of a virus of Flaviviridae family in a host in need thereof;

(yy) The use of (vv)-(xx) wherein the host is a human.

(zz) The manufacture of Compound A Form III that includes the steps of slurrying the hemisulfate AT-527 in acetone, removing the acetone, slurrying in heptane and then drying.

(aaa) The manufacture of Compound A Form III that includes slurrying in hot acetone, cooling and filtering to afford a wet cake, which is then slurried in cooled heptane, filtered and dried.

(bbb) The manufacture of Compound A Form III that includes crystallization in methanol and acetone.

(ccc) The manufacture of Compound A Form III by dissolving in methanol and then adding acetone slowly, followed by heating, cooling, and then filtering.

(ddd) A pharmaceutical composition comprising Compound A Form III and one or more excipients.

(eee) The pharmaceutical composition of (ddd) comprising mannitol.

(fff) The pharmaceutical composition of (ddd)-(eee) comprising microcrystalline cellulose.

(ggg) The pharmaceutical composition of (ddd)-(fff) comprising silicified microcrystalline cellulose.

(hhh) The pharmaceutical composition of (ddd)-(ggg) comprising colloidal silicon dioxide.

(iii) The pharmaceutical composition of (ddd)-(hhh) comprising croscarmellose sodium.

(jjj) The pharmaceutical composition of (ddd)-(iii) comprising magnesium stearate.

(kkk) The pharmaceutical composition of (ddd)-(jjj) comprising microcrystalline cellulose as an intragranular excipient.

(lll) The pharmaceutical composition of (ddd)-(kkk) comprising microcrystalline cellulose as an extragranular excipient.

(mmm) The pharmaceutical composition of (ddd)-(lll) comprising silicified microcrystalline cellulose as an intragranular excipient.

(nnn) The pharmaceutical composition of (ddd)-(mmm) comprising silicified microcrystalline cellulose as an extragranular excipient.

(ooo) The pharmaceutical composition of (ddd)-(nnn) comprising croscarmellose sodium as an intragranular excipient.

(ppp) The pharmaceutical composition of (ddd)-(ooo) comprising croscarmellose sodium as an extragranular excipient.

(qqq) The pharmaceutical composition of (ddd)-(ppp) comprising magnesium stearate as an intragranular excipient.
(rrr) The pharmaceutical composition of (ddd)-(qqq) comprising magnesium stearate as an extragranular excipient.
(sss) The pharmaceutical composition of (ddd)-(rrr) comprising anhydrous dibasic calcium hydrogen phosphate.
(ttt) A solid dosage form comprising Compound A Form III and one or more excipients.
(uuu) The solid dosage form of (ttt) comprising mannitol.
(vvv) The solid dosage form of (ttt)-(uuu) comprising microcrystalline cellulose.
(www) The solid dosage form of (ttt)-(vvv) comprising silicified microcrystalline cellulose.
(xxx) The solid dosage form of (ttt)-(www) comprising colloidal silicon dioxide.
(yyy) The solid dosage form of (ttt)-(xxx) comprising croscarmellose sodium.
(zzz) The solid dosage form of (ttt)-(yyy) comprising magnesium stearate.
(aaaa) The solid dosage form of (ttt)-(zzz) comprising microcrystalline cellulose as an intragranular excipient.
(bbbb) The solid dosage form of (ttt)-(aaaa) comprising microcrystalline cellulose as an extragranular excipient.
(cccc) The solid dosage form of (ttt)-(bbbb) comprising silicified microcrystalline cellulose as an intragranular excipient.
(dddd) The solid dosage form of (ttt)-(cccc) comprising silicified microcrystalline cellulose as an extragranular excipient.
(eeee) The solid dosage form of (ttt)-(dddd) comprising croscarmellose sodium as an intragranular excipient.
(ffff) The solid dosage form of (ttt)-(eeee) comprising croscarmellose sodium as an extragranular excipient.
(gggg) The solid dosage form of (ttt)-(ffff) comprising magnesium stearate as an intragranular excipient.
(hhhh) The solid dosage form of (ttt)-(gggg) comprising magnesium stearate as an extragranular excipient.
(iiii) The solid dosage form of (ttt)-(hhhh) comprising anhydrous dibasic calcium hydrogen phosphate.
(jjjj) A pharmaceutical composition prepared from Compound A Form III and one or more excipients.
(kkkk) The pharmaceutical composition of (jjj) comprising mannitol.
(llll) The pharmaceutical composition of (jjjj)-(kkkk) comprising microcrystalline cellulose.
(mmmm) The pharmaceutical composition of (jjjj)-(llll) comprising silicified microcrystalline cellulose.
(nnnn) The pharmaceutical composition of (jjjj)-(mmmm) comprising colloidal silicon dioxide.
(oooo) The pharmaceutical composition of (jjjj)-(nnnn) comprising croscarmellose sodium.
(pppp) The pharmaceutical composition of (jjjj)-(oooo) comprising magnesium stearate.
(qqqq) The pharmaceutical composition of (jjjj)-(pppp) comprising microcrystalline cellulose as an intragranular excipient.
(rrrr) The pharmaceutical composition of (jjjj)-(qqqq) comprising microcrystalline cellulose as an extragranular excipient.
(ssss) The pharmaceutical composition of (jjjj)-(rrrr) comprising silicified microcrystalline cellulose as an intragranular excipient.
(tttt) The pharmaceutical composition of (jjjj)-(ssss) comprising silicified microcrystalline cellulose as an extragranular excipient.
(uuuu) The pharmaceutical composition of (jjjj)-(tttt) comprising croscarmellose sodium as an intragranular excipient.
(vvvv) The pharmaceutical composition of (jjjj)-(uuuu) comprising croscarmellose sodium as an extragranular excipient.
(wwww) The pharmaceutical composition of (jjjj)-(vvvv) comprising magnesium stearate as an intragranular excipient.
(xxxx) The pharmaceutical composition of (jjjj)-(wwww) comprising magnesium stearate as an extragranular excipient.
(yyyy) The pharmaceutical composition of (jjjj)-(xxxx) comprising anhydrous dibasic calcium hydrogen phosphate.

DETAILED DESCRIPTION OF THE INVENTION

Figure 1:
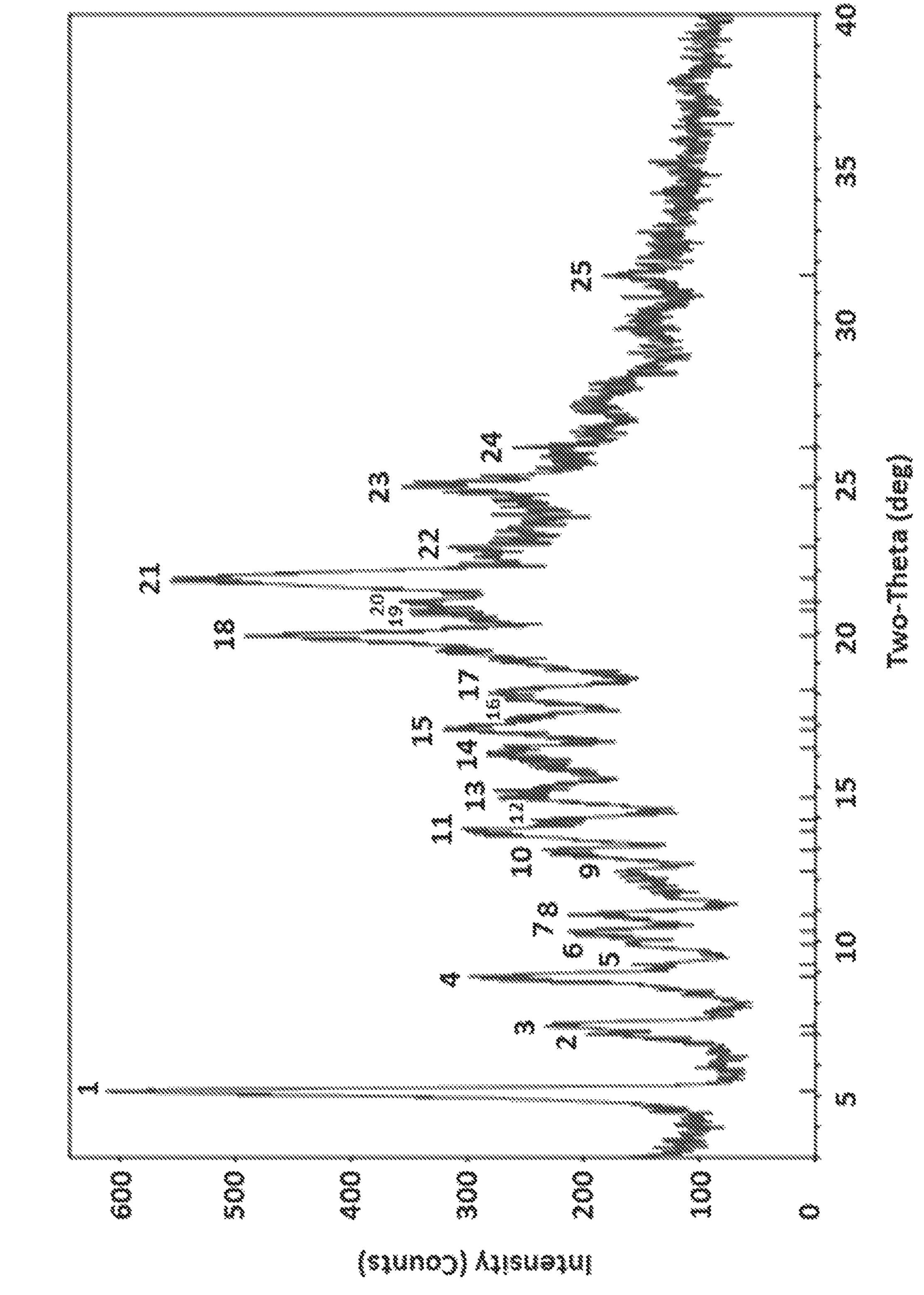
FIG. 1 is the XRPD pattern of wet Compound A Form III as described in Example 1. The labelled peaks correspond to the peaks in Table 1. The x-axis is 2Theta measured in degrees and the y-axis is intensity measured in counts.

It cannot be predicted in advance whether a compound exists in a crystalline morphic form or more than one solid form or with which solvate it exists or what the various properties of any solid form might be if one or more does exist. It also cannot be predicted whether the properties of a particular morphic form are advantageous for a therapeutic dosage form. As one example, the drug ritonavir is active in one morphic form and inactive in another form, and the inactive form is the more stable.

I. Definitions

A "patient" or "host" or "subject" is a human or non-human animal in need of medical treatment. Typically, the host is a human. A "patient" or "host" or "subject" also refers to, for example, a mammal, primate (e.g., human), cow, sheep, goat, horse, dog, cat, rabbit, rat, mice, bird and the like.

The term "prophylactic" or "preventative" when used refers to the administration of an active compound to prevent, reduce the likelihood of an occurrence or a reoccurrence of a viral infection as described herein, or to minimize a new infection relative to infection that would occur without such treatment. The present invention includes both treatment and prophylactic or preventative therapies. In certain non-limiting embodiments, the active compound is administered to a host who has been exposed to and is thus at risk of contracting a viral infection. In another alternative embodiment, a method to prevent transmission is provided that includes administering an effective amount of one of the compounds described herein to humans for a sufficient length of time prior to exposure to crowds that can be infected, including during travel or public events or meetings, including for example, up to 3, 5, 7, 10, 12, 14 or more days prior to a communicable situation.

The terms "coadminister," "coadministration," or "in combination" are used to describe the administration of Compound A Form III in combination with at least one other antiviral active agent. The timing of the coadministration is best determined by the medical specialist treating the patient. It is sometimes desired that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

A "dosage form" means a unit of administration of an active agent. Non-limiting examples of dosage forms include tablets, capsules, and gel caps.

"Carrier" means a diluent, excipient, or vehicle that is provided in a pharmaceutical composition.

A "pharmaceutically acceptable excipient" means an excipient that is useful in preparing a pharmaceutical composition/combination that is generally safe, is sufficiently non-toxic, and neither biologically nor otherwise undesirable.

The term "isolated" as used herein refers to the material in substantially pure form. An isolated compound does not have another component that materially affects the properties of the compound. In particular embodiments, an isolated form is at least 60, 70, 80, 90, 95, 98, or 99% pure.

A "positive strand RNA virus" as used herein means a virus which contains a single stranded genome made of ribonucleic acids. This genome is the "positive strand", that is the RNA can be directly translated into proteins without the need for synthesis of a complementary strand. Non limiting examples of a positive strand RNA virus include the order Nidovirales (including the following families: Arteviridae, Coronaviridae, Mesoniviridae, and Roniviridae), the order Picornavirales (including the following families: Dicistroviridae, Ifaviridae, Marnaviridae, Picornaviridae and Secoviridae), the order Tymovirales (including the following families: Alphaflexiviridae, Betaflexiviridae, Gammaflexiviridae and Tymoviridae), as well as families Alphatetraviridae, Alvernaviridae, Astroviridae, Barnaviridae, Benyviridae, Bromoviridae, Caliciviridae, Carmotetraviridae, Closteroviridae, Flaviviridae, Fusariviridae, Hepeviridae, Leviviridae, Luteoviridae, Narnaviridae, Nodaviridae, Permutotetraviridae, Potyviridae, Togaviridae, Tombusviridae and Virgaviridae.

II. Compound A and Compound B

Compound A was previously disclosed in U.S. Pat. Nos. 10,519,186; 10,894,804; and 10,906,928; and PCT Applications WO 2018/144640; WO 2019/200005; and, WO 2020/117966 assigned to Atea Pharmaceuticals. Compound A is the hemisulfate salt of Compound B.

Compound B is (isopropyl((S)-(((2R,3R,4R,5R)-5-(2-amino-6-(methylamino)-9H-purin-9-yl)-4-fluoro-3-hydroxy-4-methyltetrahydrofuran-2-yl)methoxy)(phenoxy) phosphoryl)-L-alaninate). The preparation of Compound B was previously described in U.S. Pat. Nos. 9,828,410; 10,000,523; 10,005,811; 10,239,911; 10,815,266; 10,870,672; 10,870,673; and 10,875,885 and PCT Applications WO 2016/144918; WO 2018/048937; WO 2019/200005; and, WO 2020/117966 assigned to Atea Pharmaceuticals.

An advantageous crystalline and stable form of Compound A, morphic Form III, is now provided. Four other Forms, Form I-II and IV-V are also provided and can be used alternatively to Form III for any of the methods of treatment described herein. Compound A Form III exhibits superior dissolution over the amorphous Compound A. In certain embodiments, tablets produced from Compound A Form III dissolve at least about 99% within 20 minutes, while the spray-dried amorphous material takes greater than or about 60 minutes to dissolve 99% (see Example 5). This enhanced solubility provides higher exposure and clinical efficacy.

In another embodiment, Compound A Form III is used as a high purity manufacturing intermediate. Compound A Form III is advantageous as a manufacturing intermediate because it has been shown to be surprisingly stable. Stability studies under ambient conditions show no measurable decrease in purity over 12 months.

In certain embodiments the Compound A Form III is stable over the course of at least one month at 40° C.±2° C., 75% RH±5% RH.

In certain embodiments the Compound A Form III is stable over the course of at least two months at 40° C. 12° C., 75% RH±5% RH.

In certain embodiments the Compound A Form III is stable over the course of at least three months at 40° C.±2° C., 75% RH±5% RH.

In certain embodiments the Compound A Form III is at least about, or greater than 90% pure by HPLC-UV after storage at 40° C.±2° C., 75% RH±5% RH for at least three months.

In certain embodiments the Compound A Form III has at least less than or no more than 0.05% impurities after storage at 40° C.±2° C., 75% RH±5% RH for three months.

In certain embodiments the Compound A Form III contains less than or no more than 1.1% water after storage at 40° C.±2° C., 75% RH±5% RH for at least three months.

In certain embodiments the Compound A Form III is stable over the course of at least one year at under ambient conditions.

In certain embodiments the Compound A Form III is stable over the course of at least one month at 25° C.±2° C., 60% RH±5% RH.

In certain embodiments the Compound A Form III is stable over the course of at least two months at 25° C.±2° C., 60% RH±5% RH.

In certain embodiments the Compound A Form III is stable over the course of at least three months at 25° C.±2° C., 60% RH±5% RH.

In certain embodiments the Compound A Form III is at least about, or greater than 90% pure by HPLC-UV after storage at 25° C.±2° C., 60% RH±5% RH for at least three months.

In certain embodiments the Compound A Form III has less than or no more than 0.05% impurities after storage at 25° C.±2° C., 60% RH±5% RH for at least three months.

In certain embodiments the Compound A Form III contains less than or no more than 1.0% water after storage at 25° C.±2° C., 60% RH±5% RH for at least three months.

One aspect of the present invention is isolated morphic Form III of Compound A:

Compound A

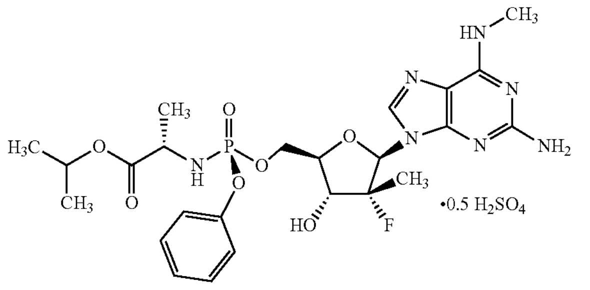

Figure 2:
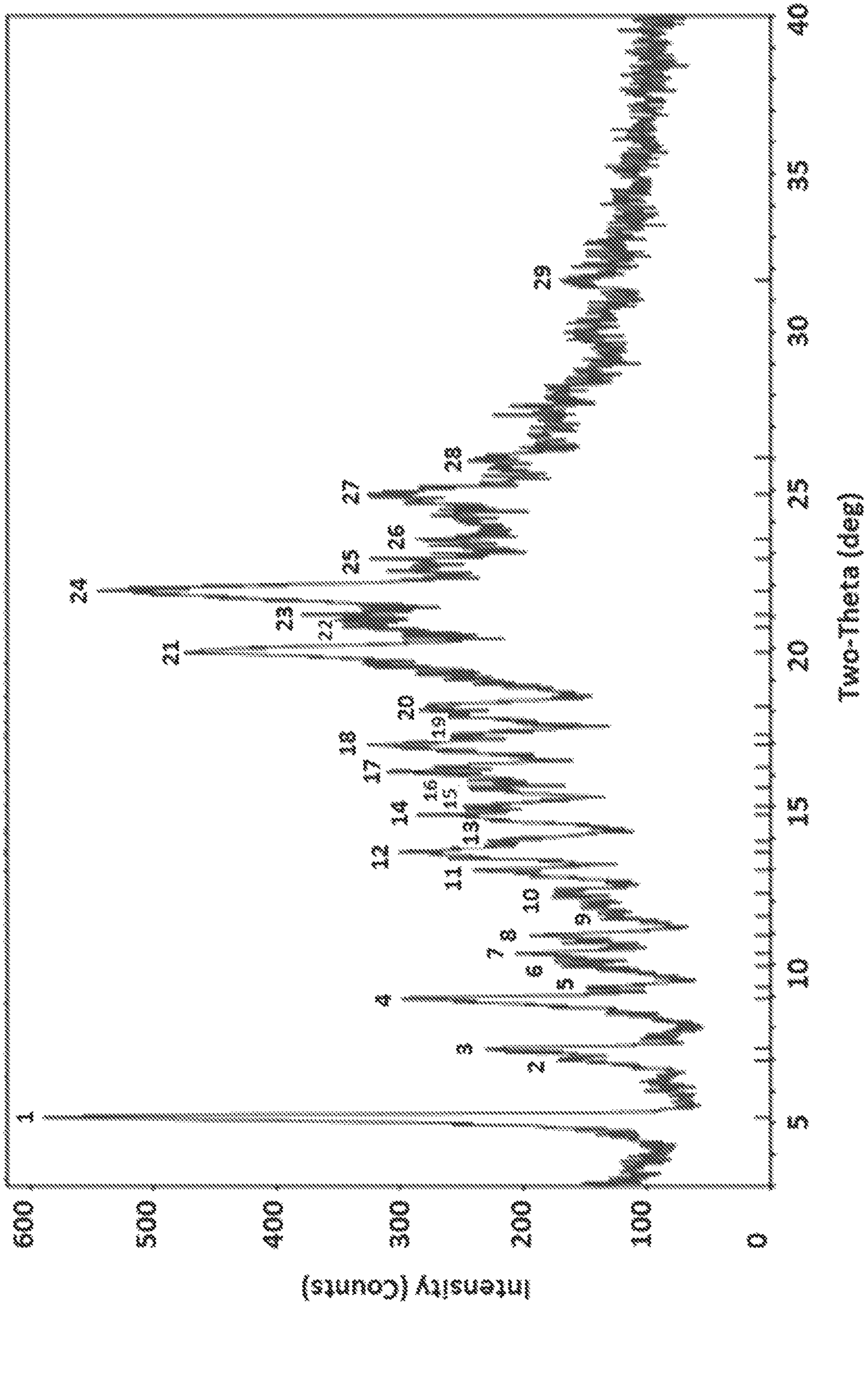
FIG. 2 is the XRPD pattern of dry Compound A Form III as described in Example 1. The labelled peaks correspond to the peaks in Table 2. The x-axis is 2Theta measured in degrees and the y-axis is intensity measured in counts.

In certain non-limiting embodiments, Compound A Form III is characterized by an XRPD pattern substantially similar to that set forth in FIG. 2. In certain non-limiting embodiments, Compound A Form III is characterized by an XRPD pattern comprising at least five, six, seven, eight, nine, or ten 2theta values selected from Table 2. In certain non-limiting embodiments, Compound A Form III is characterized by an XRPD pattern comprising:

(a) 2theta values at least or selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(b) at least nine 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(c) at least eight 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(d) at least seven 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(e) at least six 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(f) at least five 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(g) at least three 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(h) at least two 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(i) at least one 2theta value selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°;
(j) 2theta values including at least or selected from 5.2±0.2°, 8.9±0.2°, 13.6±0.2°, 19.9±0.2°, and 21.8±0.2°;
(k) at least four 2theta values including at least or selected from 5.2±0.2°, 8.9±0.2°, 13.6±0.2°, 19.9±0.2°, and 21.8±0.2°;
(l) at least three 2theta values including at least or selected from 5.2±0.2°, 8.9±0.2°, 13.6±0.2°, 19.9±0.2°, and 21.8±0.2°;
(m) at least one 2theta value selected from 5.2±0.2°, 8.9±0.2°, 13.6±0.2°, 19.9±0.2°, and 21.8±0.2°;
(n) at least one 2theta value selected from 5.2±0.2°, 8.9±0.2°, 19.9±0.2°, and 21.8±0.2°;
(o) at least one 2theta value selected from 5.2±0.2°, 8.9±0.2°, and 21.8±0.2°;
(p) at least one 2theta value selected from 5.2±0.2° and 21.8±0.2°;
(q) at least the 2theta value of 5.2±0.2°;
(r) Any one of embodiment (a)-(q) wherein the standard deviation is ±0.3° 2theta; and
(s) Any one of embodiment (a)-(q) wherein the standard deviation is ±0.4° 2theta.

In an alternative embodiment, Compound A Form III is wet and characterized by an XRPD pattern substantially similar to that set forth in FIG. 1. In certain non-limiting embodiments, wet Compound A Form III is characterized by an XRPD pattern comprising at least five, six, seven, eight, nine, or ten 2theta values selected from Table 1. In certain non-limiting embodiments, Compound A Form III is characterized by an XRPD pattern comprising:

(a) 2theta values at least or selected from 5.2±0.2°, 7.0 0.2°, 7.3±0.2°, 8.7±0.2°, 10.3±0.2°, 13.6±0.2°, 16.8±0.2°, 19.9±0.2°, 21.8±0.2°, and 24.7±0.2°;
(b) at least two, three, or four 2theta values selected from 5.2±0.2°, 7.0±0.2°, 7.3±0.2°, 8.7±0.2°, 10.3±0.2°, 13.6±0.2°, 16.8±0.2°, 19.9±0.2°, 21.8±0.2°, and 24.7±0.2°;
(c) at least five, six, or seven 2theta values selected from 5.2±0.2°, 7.0 0.2°, 7.3±0.2°, 8.7±0.2°, 10.3±0.2°, 13.6±0.2°, 16.8±0.2°, 19.9±0.2°, 21.8±0.2°, and 24.7±0.2°;
(d) at least eight, nine, or ten 2theta values selected from 5.2±0.2°, 7.0±0.2°, 7.3±0.2°, 8.7±0.2°, 10.3±0.2°, 13.6±0.2°, 16.8±0.2°, 19.9±0.2°, 21.8±0.2°, and 24.7±0.2°;
(e) 2theta values including at least or selected from 5.2 0.2°, 8.7±0.2°, 13.6±0.2°, 19.9±0.2°, and 21.8±0.2°;
(f) at least one 2theta value selected from 5.2±0.2°, 19.9±0.2°, and 21.8±0.2°;
(g) the 2theta value of 5.2±0.2°;
(h) Any one of embodiment (a)-(g) wherein the standard deviation is ±0.3° 2theta; and
(i) Any one of embodiment (a)-(g) wherein the standard deviation is ±0.4° 2theta.

In certain non-limiting embodiments, the crystalline form of Compound A is Form I.

In certain non-limiting embodiments, the crystalline form of Compound A is Form II.

In certain non-limiting embodiments, the crystalline form of Compound A is Form III.

In certain non-limiting embodiments, the crystalline form of Compound A is Form IV.

In certain non-limiting embodiments, the crystalline form of Compound A is Form V.

The synthesis of Compound A is described in U.S. Pat. Nos. 10,519,186, 10,894,804, and 10,906,928. One non-limiting illustrative process for the preparation of Compound A includes (i) a first step of dissolving Compound B in an organic solvent, for example, acetone, ethyl acetate, methanol, acetonitrile, or ether, or the like, in a flask or container;

(iii) adding dropwise $H_2SO_4$ to the solution of Compound B of step (i) at ambient or slightly increased or decreased temperature (for example 23-35 degrees C.);

(iv) stirring the reaction of step (iii) until precipitate of Compound A is formed, for example at ambient or slightly increased or decreased temperature;

(v) optionally filtering the resulting precipitate from step (iv) and washing with an organic solvent; and (vi) optionally drying the resulting Compound A in a vacuum, optionally at elevated a temperature, for example, 55, 56, 57, 58, 59, or 60° C.

In certain non-limiting embodiments, the solvent of step (i) is acetone.

U.S. Pat. No. 10,874,687 also assigned to Atea Pharmaceuticals describes the use of Compound B and Compound A for the treatment of SARS-CoV-2. Compound A, which is an orally administered drug, is currently being studied in a Phase 2 trial for hospitalized patients with moderate COVID-19.

The metabolic pathway of Compound B is described in Good et al. (2020) Preclinical evaluation of AT-527, a novel guanosine nucleotide prodrug with potent, pan-genotypic activity against hepatitis C virus. PLoS ONE 15(1): e0227104 (Scheme 1, below) and involves the initial de-esterification of the phosphoramidate (Compound B) to form metabolite 1-1, which spontaneously decomposes to metabolite 1-2. Metabolite 1-2 is next converted to the $N^6$-methyl-2,6-diaminopurine-5'-monophosphate derivative (metabolite 1-3), which is in turn metabolized to the free 5'-hydroxyl-$N^6$-methyl-2,6-diaminopurine nucleoside (metabolite 1-8) and ((2R,3R,4R,5R)-5-(2-amino-6-oxo-1,6-dihydro-9H-purin-9-yl)-4-fluoro-3-hydroxy-4-methyltetrahydrofuran-2-yl)methyl dihydrogen phosphate as the 5'-monophosphate (metabolite 1-4). Metabolite 1-4 is anabolized to the corresponding diphosphate (metabolite 1-5) and then the active triphosphate derivative (metabolite 1-6). The 5'-triphosphate can be further metabolized to generate 2-amino-9-((2R,3R,4R,5R)-3-fluoro-4-hydroxy-5-(hydroxymethyl)-3-methyltetrahydrofuran-2-yl)-1,9-dihydro-6H-purin-6-one (1-7). Metabolite 1-7 is measurable in plasma and is therefore a surrogate for the active triphosphate (1-6), which is not measurable in plasma.

Scheme 1

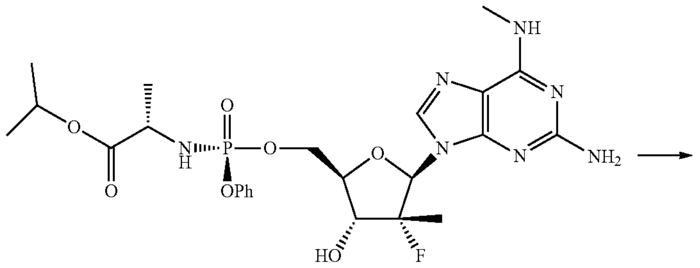

Compound 1

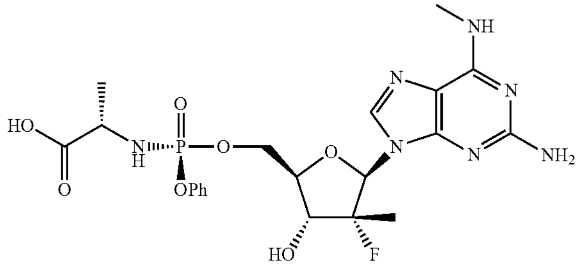

1-1

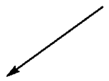

-continued
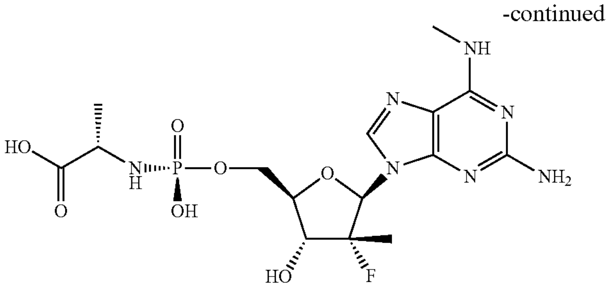
1-2
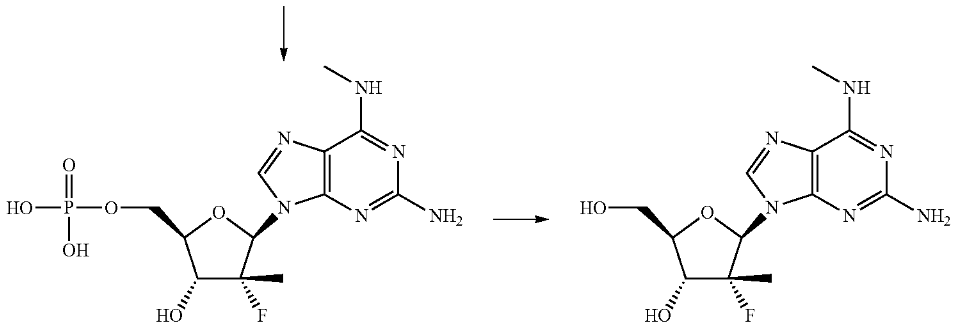
1-3 1-8
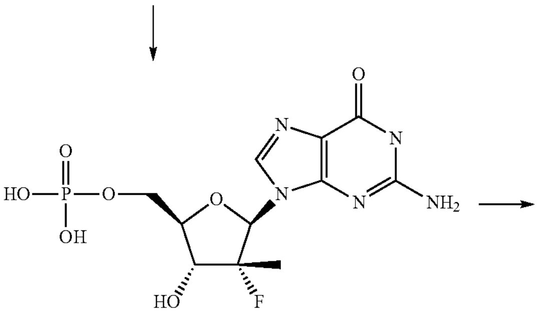
1-4
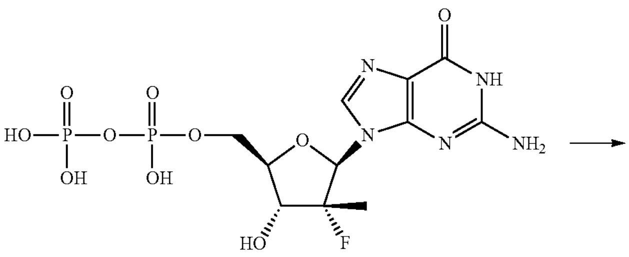
1-5
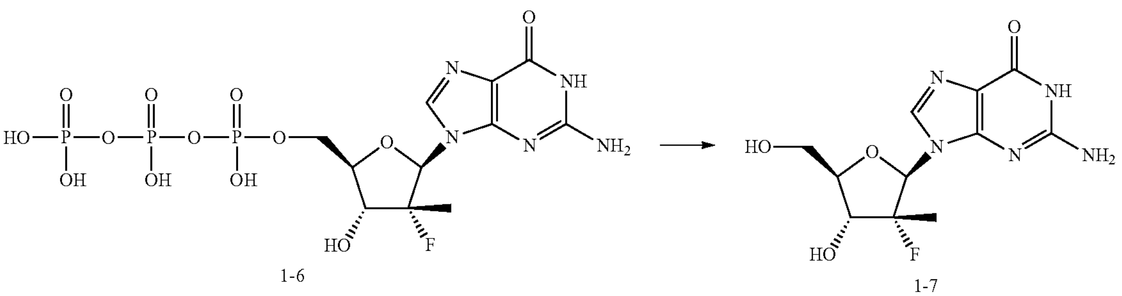
1-6 1-7

III. Compound A Form III Process of Manufacture

In certain non-limiting embodiments, Compound A Form III can be synthesized on large scale, for example by the following steps.

1. slurrying Compound A in a polar aprotic solvent, optionally at an elevated temperature below the boiling point of the solvent;
2. optionally cooling;
3. collecting the solids, optionally by filtration;
4. slurrying the resulting solids in a nonpolar solvent, at room temperature or optionally at reduced temperature;
5. filtering the solids; and
6. drying to allow crystallization.

Examples of polar aprotic solvents (e.g., that act as a solvent or partial solvent of Compound A) include, but are not limited to, acetone, methyl ethyl ketone, methyl isobutyl ketone, butanone, acetonitrile, tetrahydrofuran, propionitrile, dimethyl formamide, dimethyl acetamide, N-methyl pyrrolidione, 1,4-dioxane, ethyl acetate, dichloromethane, tetrachloroethane, dichloroethane, dimethylsulfoxide, methyl carbonate, propylene carbonate, methyl n-propyl ketone, chloroform, methyl isoamyl ketone, nitromethane, pyridine, or methyl acetate.

Examples of nonpolar solvents include, but are not limited to, pentane (n-pentane or a mixture of isomers), hexane (n-hexane or a mixture of isomers), cyclohexane, heptane (n-heptane or a mixture of isomers), petroleum ether, octane, diethyl ether, methyl tert-butyl ether, dibutyl ether, n-butyl chloride, toluene, benzene, xylene, chlorobenzene, tetrachloroethane, cyclopentane, and carbon disulfide.

In certain non-limiting embodiments of step 1, Compound A is slurried in a solvent selected from acetone, methyl ethyl ketone, and methyl acetate.

In certain non-limiting embodiments of step 1, Compound A is slurried in acetone.

In certain non-limiting embodiments of step 1, Compound A is slurried at a temperature from about room temperature to just below the boiling point of the solvent.

In certain non-limiting embodiments of step 1, Compound A is slurried at a temperature from about room temperature to not greater than about 10° C. below the boiling point of the solvent.

In certain non-limiting embodiments of step 1, Compound A is slurried at a temperature from about room temperature to not greater than about 15° C. below the boiling point of the solvent.

In certain non-limiting embodiments of step 1, Compound A is slurried at a temperature from about 55° C. to about 58° C. and the solvent is acetone.

In certain non-limiting embodiments of step 1, Compound A is slurried until the solution has saturated, or sufficiently long to break up the compound as much as possible to prepare for crystallization.

In certain non-limiting embodiments of step 1, Compound A is slurried for one to several hours.

In certain non-limiting embodiments of step 1, Compound A is slurried for up to 1, 2, 3, 4, 5, 6, 7, 8, 9, 10, 11, 12, 13, 14, 15, 16, 17, 18, 19, or 20 hours or more.

In certain non-limiting embodiments of step 2 the suspension is allowed to cool before collecting the solids.

In certain non-limiting embodiments of step 2 the suspension is allowed to cool.

In certain non-limiting embodiments of step 2 the suspension is allowed to cool to room temperature.

In certain non-limiting embodiments of step 3 the solids are collected by filtration.

In certain non-limiting embodiments of step 3 the solids are collected by vacuum filtration.

In certain non-limiting embodiments of step 3 the filtration is conducted under ambient conditions.

In certain non-limiting embodiments of step 3 the filtration is conducted while controlling the humidity.

In certain non-limiting embodiments of step 3 the filtration is conducted while controlling the humidity to less than or no more than 75% relative humidity.

In certain non-limiting embodiments of step 3 the filtration is conducted while controlling the humidity to less than or no more than 50% relative humidity.

In certain non-limiting embodiments of step 3 the filtration is conducted while controlling the humidity to less than or no more than 40% relative humidity.

In certain non-limiting embodiments of step 3, the collected solids are washed with a polar aprotic solvent, including but not limited to, acetone, methyl ethyl ketone, methyl isobutyl ketone, butanone, acetonitrile, tetrahydrofuran, propionitrile, dimethyl formamide, dimethyl acetamide, N-methyl pyrrolidione, 1,4-dioxane, ethyl acetate, dichloromethane, tetrachloroethane, dichloroethane, dimethylsulfoxide, methyl carbonate, propylene carbonate, methyl n-propyl ketone, chloroform, methyl isoamyl ketone, nitromethane, pyridine, or methyl acetate.

In certain non-limiting embodiments of step 3, the collected solids are washed with the same solvent used for slurrying.

In certain non-limiting embodiments of step 3, the collected solids are washed with dichloromethane, acetone, methyl acetate, methyl ethyl ketone, or methyl isobutyl ketone.

In certain non-limiting embodiments of step 3, the collected solids are washed with acetone.

In certain non-limiting embodiments of step 4, the solids collected in step 3 are slurried in a nonpolar solvent (e.g., an anti-solvent), including but not limited to, heptane, pentane, hexane, cyclohexane, petroleum ether, octane, diethyl ether, methyl tert-butyl ether, dibutyl ether, n-butyl chloride, toluene, benzene, xylene, chlorobenzene, tetrachloroethane, cyclopentane, and carbon disulfide.

In certain non-limiting embodiments of step 4, the solids collected in step 3 are slurried in a nonpolar solvent selected from heptane, pentane, hexane, cyclohexane, petroleum ether, octane, diethyl ether, methyl tert-butyl ether, dibutyl ether, toluene, xylene or benzene.

In certain non-limiting embodiments of step 4, the solids collected in step 3 are slurried in a nonpolar solvent selected from heptane pentane, hexane, cyclohexane, or petroleum ether.

In certain non-limiting embodiments of step 4, the solids collected in step 3 are slurried in heptane.

In certain non-limiting embodiments of step 4, the solids collected in step 3 are slurried at ambient temperature.

In certain non-limiting embodiments of step 4, the solids collected in step 3 are slurried at reduced temperature.

In certain non-limiting embodiments of step 4, the solids collected in step 3 are slurried at a temperature from about −20° C. to about 25° C.

In certain non-limiting embodiments of step 4, the solids collected in step 3 are slurried at a temperature from about −10° C. to about 15° C.

In certain non-limiting embodiments of step 4, the solids collected in step 3 are slurried at a temperature from about 0° C. to about 10° C.

In certain non-limiting embodiments of step 4, the solids collected in step 3 are slurried at a temperature from about 0° C. to about 5° C.

In certain non-limiting embodiments of step 4, the solids collected in step 3 are slurried for a sufficient time to induce crystallization.

In certain non-limiting embodiments of step 5, the suspension of step 4 is filtered to collect the solids.

In certain non-limiting embodiments of step 5, the suspension of step 4 is filtered by vacuum filtration to collect the solids.

In certain non-limiting embodiments of step 6, the solids collected in step 5 are dried.

In certain non-limiting embodiments of step 6, the solids collected in step 5 are dried sufficiently slowly to achieve good crystallization.

In certain non-limiting embodiments of step 6, the solids collected in step 5 are dried under vacuum.

In certain non-limiting embodiments of step 6, the solids collected in step 5 are dried under one atmosphere of pressure.

In certain non-limiting embodiments of step 6, the solids collected in step 5 are dried at sequential temperatures.

In certain non-limiting embodiments of step 6, the solids collected in step 5 are dried at elevated temperature and reduced pressure.

In certain non-limiting embodiments of step 6, the solids collected in step 5 are dried at a temperature from about 15° C. to about 60° C. under reduced pressure.

In certain non-limiting embodiments of step 6, the solids collected in step 5 are dried at a temperature from about 25° C. to about 40° C. under reduced pressure.

In certain non-limiting embodiments of step 6, the solids collected in step 5 are dried until the residual solvent has evaporated.

Selective Crystallization

Compound A Form III can be prepared using selective crystallization. The process can be carried out by treating a solution comprising a suitable solvent(s) and Compound A optionally in the presence of one or more seeds comprising Compound A Form III with conditions that provide for the crystallization of Compound A Form III. The selective crystallization can be carried out in any suitable organic solvent. For example, it can be carried out in an aprotic solvent, a protic solvent or a mixture thereof.

Non-limiting examples of protic solvents include but are not limited to water, methanol, ethanol, n-propanol, isopropanol, butanol, dichloromethane, dioxane, tetrahydrofuran, and acetonitrile.

Non-limiting examples of aprotic solvents include acetone, dichloromethane, and dioxane.

In certain non-limiting embodiments, Compound A Form III is crystallized from methanol and acetone.

In certain non-limiting embodiments, Compound A Form III is crystallized from ethanol and acetone.

In certain non-limiting embodiments, Compound A Form III is crystallized from n-propanol and acetone.

In certain non-limiting embodiments, Compound A Form III is crystallized from i-propanol and acetone.

In certain non-limiting embodiments, Compound A Form III is crystallized from methanol and dichloromethane.

In certain non-limiting embodiments, Compound A Form III is crystallized from methanol and dioxane.

In certain non-limiting embodiments, Compound A Form III is crystallized at between about room temperature and the boiling point of the solvent.

In certain non-limiting embodiments, the solution is seeded with crystals of Compound A Form III.

In certain non-limiting embodiments, the solution is cooled to room temperature before filtering.

In certain non-limiting embodiments, the solids collected by filtration are dried under vacuum.

In certain non-limiting embodiments, the solids collected by filtration are dried under ambient pressure.

In certain non-limiting embodiments, Compound B is dissolved in a solvent and sulfuric acid is added to afford Compound A; which is then crystallized to afford Compound A Form III.

In certain non-limiting embodiments, Compound A Form III is formed from the free base Compound B using sulfuric acid, followed by crystallization in methanol and acetone.

In certain non-limiting embodiments, Compound A Form III is formed from the free base Compound B using sulfuric acid, followed by crystallization in acetone and heptane.

In certain non-limiting embodiments, Compound A Form III can be synthesized from Compound B. Compound B is dissolved in acetone, sulfuric acid is added triggering gradual precipitation of a solid, which is filtered; the solids are then dissolved in hot methanol, and acetone slowly added, stirred and then cooled, filtered, and dried.

In certain non-limiting embodiments, the selective crystallization can be carried out at, for example, a temperature in the range of about 20 to about 50° C., about 20 to about 40° C., or about 20 to about 30° C.

IV. Pharmaceutical Compositions and Dosage Forms

The isolated Compound A Form III solid morphic form described herein can be administered in an effective amount to a host to treat any of the disorders described herein using any suitable approach that achieves the desired therapeutic result. The amount and timing of Compound A Form III administration will be dependent on the host being treated, the instructions of the supervising medical specialist, on the time course of the exposure, on the manner of administration, on the pharmacokinetic properties of the particular active compound, and on the judgment of the prescribing physician. Thus, because of host-to-host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, e.g., a pill, a capsule, a tablet, a transdermal patch, a subcutaneous patch, a dry powder, an inhalation formulation, in a medical device, suppository, buccal, or sublingual formulation. Some dosage forms, such as tablets and capsules, are subdivided into suitably sized unit doses containing appropriate quantities of the active components, e.g., an effective amount to achieve the desired purpose.

The therapeutically effective dosage of Compound A Form III described herein will be determined by the health care practitioner depending on the condition, size and age of the patient as well as the route of delivery. In general, a therapeutically effective amount of Compound A Form III in a pharmaceutical dosage form may range from about 0.1 mg/kg to more than about 25 mg/kg of the patient or considerably more, once or multiple times per day, depending on the condition or infection treated, the size of the patient, and the route of administration. Compound A Form III for example may be administered in amounts ranging from about 0.1 mg/kg to about 15 mg/kg per day of the patient, depending upon the pharmacokinetic of the agent in the patient. When a dosage form herein refers to a milligram weight dose, it refers to the amount of Compound A (i.e., the weight of the hemi-sulfate salt and the nucleotide) unless otherwise specified to the contrary. For example, approximately 600 mg of Compound A is the equivalent of approximately 550 mg of Compound B.

In certain non-limiting embodiments, Compound A Form III can be administered in a solid dosage form in an amount ranging from about 250 micrograms up to about 1200 milligrams or more at least once, twice, or three times a day. For example, at least about 5, 10, 20, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,300, 1,400, 1,500 milligrams or more, once, twice, three, or up to four times a day according to the direction of the healthcare provider. Compound A Form III is often administered orally, but may be administered parenterally, topically, or in suppository form, as well as intranasally, as a nasal spray or as otherwise described herein. More generally, Compound A Form III can be administered in a tablet, capsule, emulsion, implant, particle, sphere, cream, ointment, suppository, inhalable form, transdermal form, buccal, sublingual, topical, gel, mucosal, and the like.

In certain non-limiting embodiments, Compound A Form III is administered in a dosage form that delivers at least about 600 mg. In certain non-limiting embodiments, Compound A Form III is administered in a dosage form that delivers at least about 900 mg or 1200 mg. In certain non-limiting embodiments, Compound A Form III is administered in a dosage form that delivers at least about 500 or 550 mg. In certain non-limiting embodiments, Compound A Form III is administered in a dosage form that delivers at least about 700 mg. In certain non-limiting embodiments, Compound A Form III is administered in a dosage form that delivers at least about 1200 mg.

In certain non-limiting embodiments, Compound A Form III is administered once a day. In certain non-limiting embodiments, Compound A Form III is administered twice a day. In certain non-limiting embodiments, Compound A Form III is administered three, four, or more times a day. In certain non-limiting embodiments, Compound A Form III is administered in a dosage form that delivers at least about 600 mg once, twice, or three times a day.

In certain embodiments, Compound A Form III is administered in a dosage form that delivers an initial dose (or loading dose) followed by a maintenance dose of at least about 500 mg, at least about 550 mg, at least about 600, or at least about 750, 800, 900, 1000, 1100 or 1200 and the dose is taken once, twice, or three times a day. In certain non-limiting embodiments, the loading dose is about 1.5 times greater, about 2 times greater, about 2.5 times greater, or 3-fold times greater than the maintenance dose. In certain non-limiting embodiments, the loading dose is administered once, twice, three, four, or more times before the first maintenance dose. In certain non-limiting embodiments, Compound A Form III is administered is at loading dose of 1200 mg followed by a maintenance dose of 600 mg twice a day.

For treatment of a COVID-19 infection, for example, the following dosing regimens are illustrative. In a primary embodiment, the Compound A is provided once, twice, or three times a day for 5, 6, 7, 8, 9, 10, 11, 12, 13, 14, 15, 16, 17, 18, 19 or 20 or more days. In certain embodiments, Compound A Form III is administered at least twice a day for up to 12 days. In certain embodiments, Compound A Form III is administered at least twice a day for up to 10 day. In certain embodiments, Compound A Form III is administered at least twice a day for up to 8 days. In certain embodiments, Compound A Form III is administered at least twice a day for up to 6 days. In certain embodiments, Compound A Form III is administered at least twice a day for up to 5 days. In certain embodiments, Compound A Form III is administered at least twice a day for up to 1, 2 or 3 weeks.

For HCV infection or perhaps other RNA viral infections, a longer dosing regimen may be useful in the opinion of the healthcare specialist. In certain embodiments, Compound A Form III is administered at least once a day for at least 3 or 4 weeks. In certain embodiments, Compound A Form III is administered at least once a day for at least 6 weeks. In certain embodiments, Compound A Form III is administered at least once a day for at least 8 weeks. In certain embodiments, Compound A Form III is administered at least once a day for at least 10 weeks. In certain embodiments, Compound A Form III is administered at least once a day for at least 12 weeks. In certain non-limiting embodiments, at least about 700 mg of Compound A Form III is administered at least once or twice a day for up to 6 weeks. In certain non-limiting embodiments, at least about 600 mg of Compound A Form III is administered at least once a day for up to 6 weeks. In certain non-limiting embodiments, at least about 500 mg of Compound A Form III is administered at least once a day for up to 6 weeks. In certain non-limiting embodiments, at least about 400 mg of Compound A Form III is administered at least once a day for up to 6 weeks. In certain non-limiting embodiments, at least 300 mg of Compound A Form III is administered at least once a day for up to 6 weeks. In certain non-limiting embodiments, at least 200 mg of Compound A Form III is administered at least once a day for up to 6 weeks. In certain non-limiting embodiments, at least 100 mg of Compound A Form III is administered at least once a day for up to 6 weeks.

Compound A Form III may be administered orally, topically, parenterally, by inhalation or spray, sublingually, via implant, transdermally, via buccal administration, rectally, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers. Non-limiting examples of formulations of Compound A Form III can be found as Examples 9-14.

In accordance with the presently disclosed methods, a solid oral dosage form for administration can be in any desired form in which Compound A Form III is stable as a solid. In certain embodiments, Compound A Form III is delivered in a solid microparticle or nanoparticle. When administered through inhalation the isolated Compound A Form III may be in the form of a plurality of solid particles or droplets having any desired particle size.

Particles can be formed from Compound A Form III as described herein using a phase inversion method. In this method, Compound A Form III is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In an alternative embodiment, Compound A Form III is subjected to a milling process, included but not limited to, hand-milling, rotor-milling, ball-milling, and jet-milling to obtain microparticles and nanoparticles.

In certain non-limiting embodiments, the particle is between about 0.1 nm to about 10,000 nm, between about 1 nm to about 1,000 nm, between about 10 nm and 1,000 nm, between about 1 and 100 nm, between about 1 and 10 nm, between about 1 and 50 nm, between about 100 nm and 800 nm, between about 400 nm and 600 nm, or about 500 nm. In certain non-limiting embodiments, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm.

The pharmaceutical formulations can comprise an active dosage form made from Compound A Form III in any pharmaceutically acceptable carrier.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Where Compound A Form III crystalline compound is used in the pharmaceutical formulation, depending on the intended mode of administration, the pharmaceutical compositions can be in the form of solid form or a semi-solid dosage form that Compound A Form III is stable in, such as, for example, tablets, suppositories, pills, capsules, powders, or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal administration or in a form suitable for administration by inhalation or insufflation. The preferred manner of administration is oral using a convenient daily dosage regimen which can be adjusted according to the degree of affliction. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet or capsule. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In addition to Compound A Form III, or an active material made from Compound A Form III, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules.

Pharmaceutical formulations also are provided which provide a controlled release of a compound described herein, including through the use of a degradable polymer, as known in the art.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil, which maintain the stability of the isolated morphic form. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. In certain non-limiting embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

V. Solid Dosage Forms

An aspect of the invention is a solid dosage form that includes an effective amount of Compound A Form III, optionally in a pharmaceutically acceptable carrier.

In certain non-limiting embodiments this solid dosage form prepared directly from Compound A Form III may possess faster dissolution and/or greater solubility than a dosage form produced by spray-drying. The process for evaluating dissolution rates is provided in Example 5, and generally uses a dilute acidic solution such as 0.1 N HCl in vitro.

In certain non-limiting embodiments, the tablets formed from Compound A Form III dissolve at least approximately 90% within 30 minutes.

In certain non-limiting embodiments, the tablets formed from Compound A Form III dissolve at least approximately 90% within 20 minutes.

In certain non-limiting embodiments, the tablets formed from Compound A Form III dissolve at least approximately 95% within 30 minutes.

In certain non-limiting embodiments, the tablets formed from Compound A Form III dissolve at least approximately 98% within 30 minutes.

In certain non-limiting embodiments, the tablets formed from Compound A Form III dissolve at least approximately 99% within 30 minutes.

In certain non-limiting embodiments Compound A Form III as described herein is used to create a spray-dried dispersion (SDD) that is administered to a patient in need thereof. In this method, Compound A Form III is dissolved in an organic solvent such as acetone, methylene chloride, or other organic solvent. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In another embodiment, the spray-dried dispersion (SDD) prepared using Compound A Form III also comprises one or more pharmaceutically acceptable excipients as defined herein. In another embodiment, the spray-dried dispersion (SDD) prepared using Compound A Form III also comprises an additional therapeutic agent. In a further embodiment, the spray-dried dispersion (SDD) prepared using Compound A Form III also comprises an additional therapeutic agent and one or more pharmaceutically acceptable excipients. In another embodiment any of the described spray-dried dispersions can be coated to form a coated tablet. In an alternative embodiment the spray-dried dispersion is formulated into a tablet, but is uncoated. In certain non-limiting embodiments Compound A Form III as described herein is used to create a a granulo layered solid dispersion.

In other embodiments, the solid dispersion also contains at least one excipient selected from copovidone, poloxamer and HPMC-AS. In certain non-limiting embodiments the poloxamer is Poloxamer 407 or a mixture of poloxamers that may include Poloxamer 407. In certain non-limiting embodiments HPMC-AS is HPMC-AS-L.

In other embodiments, a solid dosage form prepared from Compound A Form III also comprises one or more of the following excipients: a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl stearate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, silicified microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g., poly(1,3-dioxan-2one)), polyanhydride (e.g., poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g., poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-

PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), or hydroxypropylmethyl cellulose acetate succinate (HPMCAS).

In other embodiments, a solid dosage form prepared from Compound A Form III also comprises one or more of the following surfactants: polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

In yet other embodiments, a solid dosage form prepared from Compound A Form III also comprises one or more of the following surfactants: polyvinyl acetate, cholic acid sodium salt, dioctyl sulfosuccinate sodium, hexadecyltrimethyl ammonium bromide, saponin, sugar esters, Triton X series, sorbitan trioleate, sorbitan mono-oleate, polyoxyethylene (20) sorbitan monolaurate, polyoxyethylene (20) sorbitan monooleate, oleyl polyoxyethylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, and sunflower seed oil.

In alternative embodiments, a solid dosage form prepared from Compound A Form III is prepared by a process that includes solvent or dry granulation optionally followed by compression or compaction, spray drying, nano-suspension processing, hot melt extrusion, extrusion/spheronization, molding, spheronization, layering (e.g., spray layering suspension or solution), or the like. Examples of such techniques include direct compression, using appropriate punches and dies, for example wherein the punches and dies are fitted to a suitable tableting press; wet granulation using suitable granulating equipment such as a high shear granulator to form wetted particles to be dried into granules; granulation followed by compression using appropriate punches and dies, wherein the punches and dies are fitted to a suitable tableting press; extrusion of a wet mass to form a cylindrical extrudate to be cut into desire lengths or break into lengths under gravity and attrition; extrusion/spheronization where the extrudate is rounded into spherical particles and densified by spheronization; spray layering of a suspension or solution onto an inert core using a technique such as a convention pan or Wurster column; injection or compression molding using suitable molds fitted to a compression unit; and the like.

Exemplary disintegrants include alginic acid, carboxymethylcellulose calcium, carboxymethylcellulose sodium, cross-linked sodium carboxymethylcellulose (sodium croscarmellose), powdered cellulose, chitosan, croscarmellose sodium, crospovidone, guar gum, low substituted hydroxypropyl cellulose, methyl cellulose, microcrystalline cellulose, sodium alginate, sodium starch glycolate, partially pregelatinized starch, pregelatinized starch, starch, sodium carboxymethyl starch, and the like, or a combination thereof.

Exemplary lubricants include calcium stearate, magnesium stearate, glyceryl behenate, glyceryl palmitostearate, hydrogenated castor oil, light mineral oil, sodium lauryl sulfate, magnesium lauryl sulfate, sodium stearyl fumarate, stearic acid, zinc stearate, silicon dioxide, colloidal silicon dioxide, dimethyldichlorosilane treated with silica, talc, or a combination thereof.

The dosage form cores described herein may be coated to result in coated tablets. The dosage from cores can be coated with a functional or non-functional coating, or a combination of functional and non-functional coatings. "Functional coating" includes tablet coatings that modify the release properties of the total composition, for example, a sustained-release or delayed-release coating. "Non-functional coating" includes a coating that is not a functional coating, for example, a cosmetic coating. A non-functional coating can have some impact on the release of the active agent due to the initial dissolution, hydration, perforation of the coating, etc., but would not be considered to be a significant deviation from the non-coated composition. A non-functional coating can also mask the taste of the uncoated composition including the active pharmaceutical ingredient. A coating may comprise a light blocking material, a light absorbing material, or a light blocking material and a light absorbing material.

Exemplary polymethacrylates include copolymers of acrylic and methacrylic acid esters, such as a. an aminomethacrylate copolymer USP/NF such as a poly(butyl methacrylate, (2-dimethyl aminoethyl)methacrylate, methyl methacrylate) 1:2:1 (e.g., EUDRAGIT E 100, EUDRAGIT EPO, and EUDRAGIT E 12.5; CAS No. 24938-16-7); b. a poly(methacrylic acid, ethyl acrylate) 1:1 (e.g., EUDRAGIT L30 D-55, EUDRAGIT L100-55, EASTACRYL 30D, KOLLICOAT MAE 30D AND 30DP; CAS No. 25212-88-8); c. a poly(methacrylic acid, methyl methacrylate) 1:1 (e.g., EUDRAGIT L 100, EUDRAGIT L 12.5 and 12.5 P; also known as methacrylic acid copolymer, type ANF; CAS No. 25806-15-1); d. a poly(methacrylic acid, methyl methacrylate) 1:2 (e.g., EUDRAGIT S 100, EUDRAGIT S 12.5 and 12.5P; CAS No. 25086-15-1); e. a poly(methyl acrylate, methyl methacrylate, methacrylic acid) 7:3:1 (e.g., Eudragit FS 30 D; CAS No. 26936-24-3); f. a poly(ethyl acrylate, methylmethacrylate, trimethylammonioethyl methacrylate chloride) 1:2:0.2 or 1:2:0.1 (e.g., EUDRAGITS RL 100, RL PO, RL 30 D, RL 12.5, RS 100, RS PO, RS 30 D, or RS 12.5; CAS No. 33434-24-1); g. a poly(ethyl acrylate, methyl methacrylate) 2:1 (e.g., EUDRAGIT NE 30 D, Eudragit NE 40D, Eudragit NM 30D; CAS No. 9010-88-2); and the like, or a combination thereof.

Suitable alkylcelluloses include, for example, methylcellulose, ethylcellulose, and the like, or a combination thereof. Exemplary water based ethylcellulose coatings include AQUACOAT, a 30% dispersion further containing sodium lauryl sulfate and cetyl alcohol, available from FMC, Philadelphia, PA; SURELEASE a 25% dispersion further containing a stabilizer or other coating component (e.g., ammonium oleate, dibutyl sebacate, colloidal anhydrous silica, medium chain triglycerides, etc.) available from Colorcon, West Point, PA; ethyl cellulose available from Aqualon or Dow Chemical Co (Ethocel), Midland, MI. Those skilled in the art will appreciate that other cellulosic polymers, including other alkyl cellulosic polymers, can be substituted for part or all of the ethylcellulose.

Other suitable materials that can be used to prepare a functional coating include hydroxypropyl methylcellulose acetate succinate (HPMCAS); cellulose acetate phthalate (CAP); a polyvinylacetate phthalate; neutral or synthetic waxes, fatty alcohols (such as lauryl, myristyl, stearyl, cetyl or specifically cetostearyl alcohol), fatty acids, including fatty acid esters, fatty acid glycerides (mono-, di-, and tri-glycerides), hydrogenated fats, hydrocarbons, normal waxes, stearic acid, stearyl alcohol, hydrophobic and hydrophilic materials having hydrocarbon backbones, or a combination thereof. Suitable waxes include beeswax, glycowax, castor wax, carnauba wax, microcrystalline wax, candelilla, and wax-like substances, e.g., material normally solid at room temperature and having a melting point of from about 30° C. to about 100° C., or a combination thereof.

In other embodiments, a functional coating may include digestible, long chain (e.g., C8-C50, specifically C12-C40), substituted or unsubstituted hydrocarbons, such as fatty acids, fatty alcohols, glyceryl esters of fatty acids, mineral and vegetable oils, waxes, or a combination thereof. Hydrocarbons having a melting point of between about 25° C. and about 90° C. may be used. Specifically, long chain hydrocarbon materials, fatty (aliphatic) alcohols can be used.

The coatings can optionally contain additional pharmaceutically acceptable excipients such as a plasticizer, a stabilizer, a water-soluble component (e.g., pore formers), an anti-tacking agent (e.g., talc), a surfactant, and the like, or a combination thereof.

A functional coating may include a release-modifying agent, which affects the release properties of the functional coating. The release-modifying agent can, for example, function as a pore-former or a matrix disrupter. The release-modifying agent can be organic or inorganic, and include materials that can be dissolved, extracted or leached from the coating in the environment of use. The release-modifying agent can comprise one or more hydrophilic polymers including cellulose ethers and other cellulosics, such as hydroxypropyl methylcellulose, hydroxypropylcellulose, hydroxyethylcellulose, methyl cellulose, cellulose acetate phthalate, or hydroxypropyl methylcellulose acetate phthalate; povidone; polyvinyl alcohol; an acrylic polymer, such as gastric soluble Eudragit FS 30D, pH sensitive Eudragit L30D 55, L 100, S 100, or L 100-55; or a combination thereof. Other exemplary release-modifying agents include a povidone; a saccharide (e.g., lactose, and the like); a metal stearate; an inorganic salt (e.g., dibasic calcium phosphate, sodium chloride, and the like); a polyethylene glycol (e.g., polyethylene glycol (PEG) 1450, and the like); a sugar alcohol (e.g., sorbitol, mannitol, and the like); an alkali alkyl sulfate (e.g., sodium lauryl sulfate); a polyoxyethylene sorbitan fatty acid ester (e.g., polysorbate); or a combination thereof. Exemplary matrix disrupters include water insoluble organic or inorganic material. Organic polymers including but not limited to cellulose, cellulose ethers such as ethylcellulose, cellulose esters such as cellulose acetate, cellulose acetate butyrate and cellulose acetate propionate; and starch can function as matrix disrupters. Examples or inorganic disrupters include many calcium salts such as mono-, di- and tri calcium phosphate; silica and, talc.

The coating may optionally contain a plasticizer to improve the physical properties of the coating. For example, because ethylcellulose has a relatively high glass transition temperature and does not form flexible films under normal coating conditions, it may be advantageous to add plasticizer to the ethylcellulose before using the same as a coating material. Generally, the amount of plasticizer included in a coating solution is based on the concentration of the polymer, e.g., can be from about 1% to about 200% depending on the polymer but is most often from about 1 wt % to about 100 wt % of the polymer. Concentrations of the plasticizer, however, can be determined by routine experimentation.

Examples of plasticizers for ethylcellulose and other celluloses include plasticizers such as dibutyl sebacate, diethyl phthalate, triethyl citrate, tributyl citrate, triacetin, or a combination thereof, although it is possible that other water-insoluble plasticizers (such as acetylated monoglycerides, phthalate esters, castor oil, etc.) can be used.

Examples of plasticizers for acrylic polymers include citric acid esters such as triethyl citrate NF, tributyl citrate, dibutyl phthalate, 1,2-propylene glycol, polyethylene glycols, propylene glycol, diethyl phthalate, castor oil, triacetin, or a combination thereof, although it is possible that other plasticizers (such as acetylated monoglycerides, phthalate esters, castor oil, etc.) can be used.

Suitable methods can be used to apply the coating material to the surface of the dosage form cores. Processes such as simple or complex coacervation, interfacial polymerization, liquid drying, thermal and ionic gelation, spray drying, spray chilling, fluidized bed coating, pan coating, or electrostatic deposition may be used.

In certain embodiments, an optional intermediate coating is used between the dosage form core and an exterior coating. Such an intermediate coating can be used to protect the active agent or other component of the core subunit from the material used in the exterior coating or to provide other properties. Exemplary intermediate coatings typically include water-soluble film forming polymers. Such intermediate coatings may include film forming polymers such as hydroxyethyl cellulose, hydroxypropyl cellulose, gelatin, hydroxypropyl methylcellulose, polyethylene glycol, polyethylene oxide, and the like, or a combination thereof; and a plasticizer. Plasticizers can be used to reduce brittleness and increase tensile strength and elasticity. Exemplary plasticizers include polyethylene glycol propylene glycol and glycerin.

VI. Methods to Treat SARS-CoV-2 Viral Infection

In certain non-limiting embodiments, a method is presented that includes the administration of an effective amount of Compound A Form III for the treatment or prevention of an infection of severe acute respiratory syndrome coronavirus-2 (SARS-CoV-2), which causes COVID-2019.

The treatment of a host infected with SARS-CoV-2 includes drug resistant and multidrug resistant forms of the virus and related disease states, conditions, or complications of the viral infection, including pneumonia, such as 2019 novel coronavirus-infected pneumonia (NCIP), acute lung injury (ALI), and acute respiratory distress syndrome (ARDS). Additional non-limiting complications include hypoxemic respiratory failure, acute respiratory failure (ARF), acute liver injury, acute cardiac injury, acute kidney injury, septic shock, disseminated intravascular coagulation, blood clots, multisystem inflammatory syndrome, chronic fatigue, rhabdomyolysis, and cytokine storm.

In certain non-limiting embodiments, the administration of Compound A Form III to a patient in need thereof results in a reduction in the incidence of progressive respiratory insufficiency (PRI) as measured by greater than or equal to a 1-tier or even 2-tier or more increase in respiratory support methods required to maintain satisfactory oxygenation ($SpO_2 \geq 93\%$) using the 6-tier hierarchical levels of respiratory support methods described below.

The scale of increasing respiratory support levels includes:

Level 1: Normal oxygenation on room air ($SpO_2 \geq 93\%$), no need for supplemental $O_2$ Level 2: Persistent hypoxemia on room air ($SpO_2 \geq 93$) with requirement for low-level supplemental $O_2$ by nasal cannular or mask (up to 2 L/min) to maintain $SpO_2 \geq 93$ Level 3: Requirement for higher levels of passive supplemental $O_2$ by nasal cannular or mask (up to 2 L/min) to maintain $SpO_2 \geq 93$ Level 4: Requirement for oxygenation by positive-pressure devices, e.g., Continuous Positive Airway Pressure (CPAP) or Bi-level Positive Airway Pressure (BiPAP) or other non-invasive positive-pressure respiratory support methods to main satisfactory oxygenation and/or ventilation Level 5: Requires invasive respiratory support (intubated mechanical ventilation or ECMO)

Level 6: Death

In certain non-limiting embodiments, the reduction in PRI is an increase from level 5 to level 3, level 5 to level 2, or level 5 to level 1. In certain non-limiting embodiments, the reduction in PRI is an increase from level 4 to level 2 or level 4 to level 1. In certain non-limiting embodiments, the reduction in PRI is an increase from level 3 to level 1.

In certain non-limiting embodiments, the administration of Compound A Form III reduces the median time to Clinical Recovery (status 6, 7, or 8 in the NIAID Clinical Status scale using an adapted National Institute of Allergy and Infectious Diseases (NIAID) ordinal scale of Clinical Status) by at least 3, 4, 5 or more days. In certain non-limiting embodiments, the administration of Compound A Form III results in an improvement as measured by the adapted ordinal scale of Clinical Status.

From most severe disease to progressively less severe disease, the stages of the adapted ordinal scale of overall Clinical Status are defined as follows:

1. Death
2. Hospitalized, on invasive mechanical ventilation or ECMO
3. Hospitalized, on non-invasive ventilation or high flow oxygen devices
4. Hospitalized, requiring supplemental oxygen
5. Hospitalized, not requiring supplemental oxygen—requiring ongoing medical care (COVID-19 related or otherwise)
6. Hospitalized, not requiring supplemental oxygen; no longer requires close medical care for COVID-19
7. Not hospitalized, but with limitation on activities and needing close outpatient care for COVID-19 manifestations
8. Not hospitalized, no limitations on activities, no need for continued close medical care.

In certain non-limiting embodiments, the administration of Compound A Form III reduces the median time to Clinical Recovery (status 6, 7, or 8 in the NIAID Clinical Status scale using an adapted National Institute of Allergy and Infectious Diseases (NIAID) ordinal scale of Clinical Status) by at least 5 days, at least 6 days, at least 7 days, at least 8 days, at least 9 days, or at least 10 days.

In certain non-limiting embodiments, the administration of Compound A Form III reduces the duration of hospitalization for a patient infected with COVID-19.

In certain non-limiting embodiments, the administration of Compound A Form III reduces the time to sustained non-detectable SARS-CoV-2 virus in the nose and/or throat in a patient infected with COVID-19.

In certain non-limiting embodiments, the administration of Compound A Form III reduces the proportion of patients in a hospital population who are SARS-CoV-2 positive after at least about 5, 6, 7, 8, 9, 10, 11, 12, 13, or 14 days of treatment.

VII. Methods to Treat Hepatitis C (HCV)

In another aspect, the present invention includes a method for prevention or prophylaxis of an HCV infection or a disease state or related or follow-on disease state, condition or complication of an HCV infection, including cirrhosis and related hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount of Compound A Form II as described above in combination with a pharmaceutically acceptable carrier, additive, or excipient, optionally in combination with another anti-HCV agent. In another embodiment, the active compounds of the invention can be administered to a patient after a hepatitis-related liver transplantation to protect the new organ.

Compound A Form III can also be used to treat the range of HCV genotypes. At least six distinct genotypes of HCV, each of which have multiple subtypes, have been identified globally. Genotypes 1-3 are prevalent worldwide, and Genotypes 4, 5, and 6 are more limited geographically. Genotype 4 is common in the Middle East and Africa. Genotype 5 is mostly found in South Africa. Genotype 6 predominately exists in Southeast Asia. Although the most common genotype in the United States is Genotype 1, defining the genotype and subtype can assist in treatment type and duration. For example, different genotypes respond differently to different medications and optimal treatment times vary depending on the genotype infection. Within genotypes, subtypes, such as Genotype 1a and Genotype 1b, respond differently to treatment as well. Infection with one type of genotype does not preclude a later infection with a different genotype.

In certain non-limiting embodiments, Compound A Form III is used to treat HCV Genotype 1, HCV Genotype 2, HCV Genotype 3, HCV Genotype 4, HCV Genotype 5, or HCV Genotype 6. In certain non-limiting embodiments, Compound A Form III is used to treat HCV Genotype 1a. In certain non-limiting embodiments, Compound A Form III is used to treat HCV Genotype 1b. In certain non-limiting embodiments, Compound A Form III is used to treat HCV Genotype 2a. In certain non-limiting embodiments, Compound A Form III is used to treat HCV Genotype 2b. In certain non-limiting embodiments, Compound A Form III is used to treat HCV Genotype 3a. In certain non-limiting embodiments, Compound A Form III is used to treat HCV Genotype 4a. In certain non-limiting embodiments, Compound A Form III is used to treat HCV Genotype 4d.

In certain non-limiting embodiments, Compound A Form III is used to treat HCV Genotype 5a. In certain non-limiting embodiments, Compound A Form III is used to treat HCV Genotype 6a. In certain non-limiting embodiments, Compound A Form III is used to treat HCV Genotype 6b, 6c, 6d, 6e, 6f, 6 g, 6h, 6i, 6j, 6k, 6l, 6m, 6n, 6o, 6p, 6q, 6r, 6s, 6t, or 6u.

VIII. Methods to Treat Other RNA Viral Infections

In one aspect of the present invention, Compound A Form III is administered in an effective amount to a host in need thereof for the treatment of an RNA virus. The present invention includes both treatment and prophylactic or preventative therapies for RNA viruses. In certain non-limiting embodiments, Compound A Form III, is administered to a host who has been exposed to and thus is at risk of infection or at risk of reinfection of an RNA virus. Prophylactic treatment may be administered, for example, to a subject not yet exposed to or infected with an RNA virus, but who is susceptible to, or otherwise at risk of exposure or infection with an RNA virus. In certain non-limiting embodiments, a host at risk for infection or reinfection is administered Compound A Form III indefinitely until the risk of exposure no longer exists.

In certain non-limiting embodiments, a method to prevent transmission is provided that includes administering an effective amount of Compound A Form III to humans for a sufficient length of time prior to exposure to crowds that can be infected, including during travel or public events or meetings, including for example, up to 3, 5, 7, 10, 12, 14 or more days prior to a communicable situation, either because the human is infected or to prevent infection from an infected person in the communicable situation.

In certain non-limiting embodiments, Compound A Form III is administered in an effective amount for at least two weeks, three weeks, one month, two months, three months, four months, five months, or six months or more after infection.

The invention is directed to a method of treatment or prophylaxis of an RNA virus, including drug resistant and multidrug resistant forms of RNA virus and related disease states, conditions, or complications of an RNA virus infection, as well as other conditions that are secondary to an RNA virus infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, and jaundice, among others. The method comprises administering to a host in need thereof an effective amount of Compound A Form III, optionally in combination with at least one additional bioactive agent, for example, an additional anti-RNA virus agent, further in combination with a pharmaceutically acceptable carrier additive and/or excipient.

In yet another aspect, the present invention is a method for prevention or prophylaxis of an RNA virus infection or a disease state or related or follow-on disease state, condition or complication of an RNA virus infection, including hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount of at least one compound according to the present invention as described above in combination with a pharmaceutically acceptable carrier, additive, or excipient, optionally in combination with another anti-RNA virus agent.

The Baltimore classification system sorts viruses into Groups, labeled I-VII, according to their genome. DNA viruses belong to Groups I, II, and VII, while RNA viruses belong to Groups III-VI. RNA viruses use ribonucleic acid as their genetic material. An RNA virus can have a double-stranded (ds) RNA genome or a single-stranded RNA genome. Viruses with single-stranded RNA genomes can have a positive-strand genome or negative-strand genome. Group III viruses are double-stranded RNA viruses. Groups IV and V are both single-stranded RNA viruses, but Groups IV viruses are positive-sense and Groups V are negative-sense. Group VI are positive-sense single-stranded RNA viruses that replicate through a DNA intermediate.

In certain non-limiting embodiments, Compound A Form III is administered to a host that is infected with a double-stranded RNA virus.

In certain non-limiting embodiments, Compound A Form III is administered to a host that is infected with a single-stranded RNA virus.

In certain non-limiting embodiments, Compound A Form III is administered to a host that is infected with a positive-stranded RNA virus.

In an alternative embodiment, Compound A Form III is administered to a host that is infected with a negative-stranded RNA virus.

In certain non-limiting embodiments, Compound A Form III is administered to a host in need thereof, including a human, to treat a Group III dsRNA virus selected from the Amalgaviridae family, Birnaviridae family, Chrysoviridae family, Cystoviridae family, Endornaviridae family, Hypoviridae family, Megabirnaviridae family, Partitiviridae family, Picobirnaviridae family, Quadriviridae family, Reoviridae family and Totiviridae family.

In certain non-limiting embodiments Compound A Form III is administered to a host in need thereof, including a human, to treat a Group IV positive-sense ssRNA virus. The order Nidovirales includes the following families: Arteviridae, Coronaviridae, Mesoniviridae, and Roniviridae. The order Picornavirales includes the following families: Dicistroviridae, Ifaviridae, Marnaviridae, Picornaviridae and Secoviridae. The order Tymovirales includes the following families: Alphaflexiviridae, Betaflexiviridae, Gammaflexiviridae and Tymoviridae. The following positive-sense ssRNA viruses include viruses from the following unassigned families: Alphatetraviridae, Alvernaviridae, Astroviridae, Barnaviridae, Benyviridae, Bromoviridae, Caliciviridae, Carmotetraviridae, Closteroviridae, Flaviviridae, Fusariviridae, Hepeviridae, Leviviridae, Luteoviridae, Narnaviridae, Nodaviridae, Permutotetraviridae, Potyviridae, Togaviridae, Tombusviridae and Virgaviridae.

In certain non-limiting embodiments Compound A Form III is administered to a host in need thereof, including a human, to treat severe acute respiratory syndrome coronavirus 2 (SARS-CoV-2). In other embodiments, Compound A Form III is administered to a host in need thereof, including a human, to treat other Coronaviridae viral infections. Coronaviridae viral infections include infections with virus of the genuses Alphacoronavirus, Betacoronavirus (which includes severe acute respiratory syndrome coronavirus), Gammacoronavirus, and Deltacoronavirus. In certain non-limiting embodiments Compound A Form III is administered to a host in need thereof, including a human, to treat severe acute respiratory syndrome coronavirus (SARS-CoV2).

In certain non-limiting embodiments Compound A Form III is administered to a host in need thereof, including a human, to treat a Flaviviridae viral infections including, but not limited to, infections with viruses of the genera Flavivirus, Hepacivirus and Pestivirus. Flavivirus infections include Dengue fever, Kyasanur Forest disease, Powassan disease, Wesselsbron disease, West Nile fever, yellow fever, Zika virus, *Rio bravo, Rocio*, Negishi, and the encephalitises including: Japanese B encephalitis, *Montana myotis* leukoencephalitis virus, central European encephalitis (tick-borne encephalitis), *Ilheus* virus, Murray Valley encephalitis, St. Louis encephalitis, Louping ill, and Russian spring-rodents summer encephalitis.

Species of the Hepacivirus genera include Hepacivirus A-Hepacivirus N. The hepatitis C virus (HCV) is caused by Hepatovirus C and in certain non-limiting embodiments, Compound A Form III is administered to treat HCV.

Pestivirus infections include primarily livestock diseases, including swine fever in pigs, BVDV (bovine viral diarrhea virus) in cattle, and Border Disease virus infections.

In certain non-limiting embodiments Compound A Form III is administered to a host in need thereof, including a human, to treat a Picornavirus infections including, but not limited to infections with viruses of the genuses Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Salivirus, Sapelovirus, Senecavirus, Teschovirus, and Tremovirus.

In certain non-limiting embodiments Compound A Form III is administered to a host in need thereof, including a human, to treat a Togaviridae family virus. The Togaviridae family comprises four genera: Alphavirus, Arterivirus, Rubivirus and Pestivirus. The alphavirus genus contains four viruses that produce encephalitis: Eastern equine encephalitis (EEE) virus, Venezuelan equine encephalitis (VEE) virus, Western equine encephalitis (WEE) virus and the Everglades virus. In addition, the Alphavirus genus includes the Chikungunya virus, Mayaro virus, Ockelbo virus, O'nyong-nyong virus, Ross River virus, Semliki Forest virus and Sindbis virus (SINV). The Arterivirus genus contains a single member: the equine arteritis virus. The pestivirus genus contains three viruses of veterinary importance, namely the bovine viral diarrhea virus (BVDV), hog cholera virus and border disease virus. The only member of the Rubivirus genus is the rubella virus.

In certain non-limiting embodiments Compound A Form III is administered to a host in need thereof, including a human, to treat a Group V negative-sense ssRNA viruses including, but not limited to, the order Mononegavirales. The Mononegavirales order includes, but is not limited to, the following families and viruses: Bornaviridae, Borna disease virus; Filoviridae, Ebola virus and Marburg virus; Paramyxoviridae, Measles virus, Mumps virus, Nipah virus, Hendra virus, respiratory syncytial virus (RSV) and Newcastle disease virus (NDV); Rhabdoviridae, Rabies virus and Nyamiviridae, Nyavirus. Unassigned families and viruses include, but are not limited to: Arenaviridae, Lassa virus; Bunyaviridae, Hantavirus, Crimean-Congo hemorrhagic fever; Ophioviridae and Orthomyxoviridae, influenza virus.

In certain non-limiting embodiments Compound A Form III is administered to a host in need thereof, including a human, to treat a Bunyaviridae family virus. The Bunyaviridae family comprises more than two hundred named viruses and the family is divided into five genera: Hantavirus, Nairovirus, Orthobunyavirus, Phlebovirus and Tospovirus. The Hantavirus genus includes the Hantaan virus. The Nairovirus genus includes the Crimean-Congo Hemorrhagic Fever virus and Dugbe viruses. The Orthobunyavirus genus is comprised of approximately one hundred seventy viruses that have been divided into multiple serogroups. The Serogroups include *Anopheles* A serogroup, *Anopheles* B serogroup, Bakau serogroup, Bunyamwera serogroup, *Bwamba* serogroup, California serogroup, *Capim* serogroup, *Gamboa* serogroup, Group C serogroup, *Guama* serogroup, Koongol serogroup, Mapputta serogroup, Minatitlan serogroup, Nyando serogroup, Olifanstlei serogroup, Patois serogroup, Simbu serogroup, *Tete* serogroup, Turlock serogroup, *Wyeomyia* serogroup and the Unclassified group. The *Anopheles* A serogroup includes the *Anopheles* A virus, Tacaiuma virus, Virgin River virus, *Trombetas* complex, Arumateua virus, Caraipe virus, *Trombetas* virus and the *Tucurui* virus. The *Anopheles* B serogroup includes the *Anopheles* B virus and the *Boraceia* virus. The Bakau serogroup includes the Bakau virus and the Nola virus. The Bunyamwera serogroup includes the Birao virus, Bozo virus, Bunyamwera virus, Cache Valley virus, Fort Sherman virus, Germiston virus, Guaroa virus, Ilesha virus, *Kairi* virus, Main Drain virus, Northway virus, Playas virus, Potosi virus, Shokwe virus, Stanfield virus, Tensaw virus, Xingu virus, *Batai* virus, Calovo virus, Chittoor virus, *Garissa* virus, KV-141 virus, and Ngari virus. The *Bwamba* serogroup includes the *Bwamba* and Pongola viruses. The California serogroup includes the California encephalitis virus, Chatanga virus, Inkoo virus, Jamestown Canyon virus, Jerry Slough virus, Keystone virus, Khatanga virus, La Crosse virus, *Lumbo* virus, Melao virus, Morro Bay virus, San Angelo virus, Serra do *Navio* virus, Snowshoe hare virus, South River virus, Tahyna virus, and the *Trivittatus* virus. The *Capim* serogroup includes the Acara virus, Benevides virus and the *Capim* virus. The *Gamboa* serogroup includes the Alajuela virus, *Gamboa* virus, Pueblo Viejo virus and San Juan virus. The Group C serogroup includes, but is not limited to, Bruconha virus, Ossa virus, Apeu virus, Brunconha virus, Caraparu virus, Vinces virus, Madrid virus, Gumbo limbo virus, *Marituba* virus, Murutucu virus, Nepuyo virus, Restan virus, Itaqui virus and Oriboca virus. The *Guama* serogroup includes, but is not limited to, the Bertioga virus, Bimiti virus, *Cananeia* virus, *Guama* virus, Guaratuba virus, Itimirim virus and *Mirim* virus. The Koongol serogroup includes, but is not limited to, the Koongol virus and Wongal virus. The Mapputta serogroup includes, but is not limited to, the Buffalo Creek virus, Mapputta virus, *Maprik* virus, Murrumbidgee virus and Salt Ash virus. The Minatitlan serogroup includes, but is not limited to, Minatitlan virus and *Palestina* virus. The Nyando serogroup includes, but is not limited to, *Eretmapodites* virus and Nyamdo virus. The Olifanstlei serogroup includes, but is not limited to, Botambi virus and Olifanstlei virus. The Patois serogroup includes, but is not limited to, Abras virus, Babahoyo virus, *Pahayokee* virus, Patois virus and Shark River virus. The Simbu serogroup includes, but is not limited to, Iquitos virus, Jatobal virus, Leanyer virus, Madre de Dios virus, Oropouche virus, *Oya* virus, Thimiri virus, Akabane virus, Tinaroo virus, Douglas virus, Sathuperi virus, Aino virus, Shuni virus, Peaton virus, Shamonda virus, Schmallenberg virus and Simbu virus. The *Tete* serogroup includes, but is not limited to, *Batama* virus and *Tete* virus. The Turlock serogroup includes, but is not limited to, M'Poko virus, Turlock virus and Umbre virus. The *Wyeomyia* serogroup includes, but is not limited to, *Anhembi* virus, Cachoeira Porteira virus, Iaco virus, Macaua virus, Sororoca virus, Taiassui virus, Tucunduba virus and *Wyeomyia* virus. The Unclassified serogroup includes, but is not limited to, *Batama* virus, Belmont virus, Enseada virus, Estero Real virus, Jurona virus, Kaeng Khei virus and Kowanyama virus. The Phlebovirus genus includes, but is not limited to, the Naples and Sicilian Sandfly Fever viruses and Rift Valley Fever virus. The Tospovirus genus includes, but is not limited to, the type species Tomato spotted wilt virus and the following species: Bean necrotic mosaic virus, *Capsicum* chlorosis virus, Groundnut bud necrosis virus, Groundnut ringspot virus, Groundnut yellow spot virus, *Impatiens* necrotic spot virus, Iris yellow spot virus, Melon yellow spot virus, Peanut bud necrosis virus, Peanut yellow spot virus, Soybean vein necrosis-associated virus, Tomato chlorotic spot virus, Tomato necrotic ringspot virus, Tomato yellow ring virus, Tomato zonate spot virus, Watermelon bud necrosis virus, Watermelon silver mottle virus and Zucchini lethal chlorosis virus.

Flaviviridae Family Viral Infections

In one aspect of the present invention, a method is presented that includes the administration of Compound A Form III for the treatment or prevention of an infection of a virus of the Flaviviridae family to a host, including a human, in need thereof. In certain non-limiting embodiments, the virus of the Flaviviridae family is of the Flavivirus genus, including, but not limited to Dengue Fever, Yellow Fever, Zika virus, and West Nile virus. In certain non-limiting embodiments, the virus of the Flavivirus genus is Dengue Fever. In certain non-limiting embodiments, the Dengue Fever is Dengue Fever 1 (DENV-1). In certain non-limiting embodiments, the Dengue Fever is Dengue Fever 2 (DENV-2). In certain non-limiting embodiments, the Dengue Fever is Dengue Fever 3 (DENV-3). In certain non-limiting embodiments, the Dengue Fever is Dengue Fever 4 (DENV-4). In certain non-limiting embodiments, the virus of the Flavivirus genus is an encephalitis including central European encephalitis, *Ilheus* virus, Murray Valley encephalitis, St. Louis encephalitis, Japanese B encephalitis, Louping ill, and Russian spring-rodents summer encephalitis. In certain non-limiting embodiments, the virus of the Flavivirus genus is Japanese B encephalitis.

In an alternative embodiment, the virus of the Flavivirus genus is selected from Apoi virus, *Aroa* virus, *Bamaga* virus, Bagaza virus, Banzi virus, Bouboui virus, Bukalasa bat virus, Cacipacore virus, Carey Island virus, Cowbone Ridge virus, Dakar bat virus, Edge Hill virus, Entebbe bat virus, Gadgets Gully virus, Israel turkey meningoencephalomyelitis virus, Jugra virus, Jutiapa virus, Kadam virus, Kedougou virus, Kokobera virus, Koutango virus, Kyasanur Forest disease virus, Langat virus, Meaban virus, Modoc virus, *Montana myotis* leukoencephalitis virus, Ntaya virus, Omsk hemorrhagic fever virus, Phnom Penh bat virus, Powassan virus, *Rio* Bravo virus, Royal Farm virus, Saboya virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, Yaounde virus, and Yokose virus.

In certain non-limiting embodiments, the virus of the Flaviviridae family is of the Pegivirus genus. In certain non-limiting embodiments, the virus of the Pegivirus genus is selected from Pegivirus A, Pegivirus B, Pegivirus C, Pegivirus D, Pegivirus E, Pegivirus F, Pegivirus G, Pegivirus H, Pegivirus I, Pegivirus J, Pegivirus K, and Sifaka pegivirus.

Pestivirus infections of the Flaviviridae family include primarily livestock diseases, including swine fever in pigs, BVDV (bovine viral diarrhea virus) in cattle, and Border Disease virus infections.

IX. Combination and Alternation Therapy

Compound A Form III as described herein can be administered on top of the current standard of care for, or in combination or alternation with any other compound or therapy that the healthcare provider deems beneficial for the patient. The combination and/or alternation therapy can be therapeutic, adjunctive, or palliative.

It is well recognized that drug-resistant variants of viruses can emerge after prolonged treatment with an antiviral agent. Drug resistance most typically occurs by mutation of a gene that encodes for an enzyme used in viral replication. The efficacy of a drug against an RNA virus infection can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed purine nucleotides are polymerase inhibitors, it may be useful to administer the compound to a host in combination with, for example a:

(1) Protease inhibitor;
(2) Another polymerase inhibitor;
(3) Allosteric polymerase inhibitor;
(4) Interferon alfa-2a, which may be pegylated or otherwise modified, and/or ribavirin;
(5) Non-substrate-based inhibitor;
(6) Helicase inhibitor;
(7) Antisense oligodeoxynucleotide (S-ODN);
(8) Aptamer;
(9) Nuclease-resistant ribozyme;
(10) iRNA, including microRNA and SiRNA;
(11) Antibody, partial antibody or domain antibody to the virus; or
(12) Viral antigen or partial antigen that induces a host antibody response.

SARS-CoV-2

There is currently only one approved vaccine (Comirnaty, Pfizer-BioNTech) and one approved drug (Veklury, remdesivir) for COVID-19, the disease caused by the SARS-CoV-2 virus. The FDA has issued Emergency Use Authorizations for two other vaccines (produced by Janssen Pharmaceuticals and Moderna Therapeutics) as well as seven antiviral drugs, including molnupiravir, Paxlovid (nirmatrelvir co-packaged with ritonavir), Evusheld (tixagevimab co-packaged with cilgavimab), Actemra (Tocilizumab), Sotrovimab, Bamlanivimab and Etesevimab, REGEN-COV (Casirivimab and Imdevimab). However, due to the spread of the omicron variant of the SARS-CoV-2 virus, the FDA has limited the authorized use of Bamlanivimab and Etesevimab as well as REGEN-COV. As new variants continue to evolve, more of the vaccines and drugs currently authorized for emergency use may become ineffective.

It has been observed that COVID-19 patients can pass through various stages of disease, and that the standard of care can differ based on what stage of illness the patient presents with or advances to. COVID-19 is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID-19 patients, requiring anticoagulant therapy. It is considered that these clots may cause long term, or even permanent damage if not treated and disease alleviated.

More specifically, COVID-19 has been described as progressing through three general stages of illness: stage 1 (early infection), stage 2 (pulmonary phase), and stage 3 (hyperinflammation phase/cytokine storm).

Stage 1 is characterized by non-specific, and often mild, symptoms. Viral replication is occurring, and it is appropriate to begin immediate treatment with the compounds described herein and perhaps in combination or alternation with another anti-viral therapy. Interferon-β may also be administered to augment the innate immune response to the virus. In certain non-limiting embodiments, therefore, Compound A Form III is used in an effective amount in combination or alternation with interferon-β and or an additional anti-viral drug.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In certain non-limiting embodiments, Compound A Form III is used in an effective amount in combination with a corticosteroid which may be a glucocorticoid. Non-limiting examples are budesonide (Entocort EC), bethamethasone, (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), hydrocortisone, or dexamethasone (Dexamethasone Intensol, DexPak 10 Day, DexPak 13 Day, DexPak 6 Day).

Stage 3, the final stage of the disease, is characterized by progressive disseminated intravascular coagulation (DIC), a condition in which small blood clots develop throughout the bloodstream. This stage also can include multi-organ failure (e.g. vasodilatory shock, myocarditis). It has also been observed that many patients respond to this severe stage of COVID-19 infection with a "cytokine storm." There does appear to be a bi-directional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, bivalirudin (Angiomax), rivaroxaban (Xarelto), dabigatran (Pradaxa), apixaban (Eliquis), or edoxaban (Lixiana). In certain non-limiting embodiments, Compound A Form III is administered in combination or in alternation with anti-coagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In certain non-limiting embodiments, Compound A Form III is administered in combination or in alternation with tocilizumab or sarilumab. Additional non-limiting examples of immunosuppressant drugs used to treat the overreacting immune system include Janus kinase inhibitors (tofacitinib (Xeljanz)); calcineurin inhibitors (cyclosporine (Neoral, Sandimmune, SangCya)), tacrolimus (Astagraf XL, Envarsus XR, Prograf)); mTOR inhibitors (sirolimus (Rapamune), everolimus (Afinitor, Zortress)); and, IMDH inhibitors (azathioprine (Azasan, Imuran), leflunomide (Arava), mycophenolate (CellCept, Myfortic)). Additional antibodies and biologics include abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), and daclizumab (Zinbryta)).

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate, or levofloxacin. In certain non-limiting embodiments, thus Compound A Form III is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially, and for ongoing anxiety, sedatives can be added sequentially. Non-limiting examples of analgesics include acetaminophen, ketamine, and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol, and phenobarbital. In certain non-limiting embodiments, Compound A Form III is administered in combination or in alternation with a pain reliever, such as acetaminophen, ketamine, hydromorphone, fentanyl, or morphine. In certain non-limiting embodiments, Compound A Form III is administered in combination or in alternation with a sedative, such as melatonin, olanzapine, quetiapine, propofol, dexmedetomidine, haloperidol, or phenobarbital.

Additional drugs that may be used in the treatment of a COVID patient include, but are not limited to favipiravir, fingolimod (Gilenya), methylprednisolone, bevacizumab (Avastin), Actemra (tocilizumab), umifenovir, losartan and the monoclonal antibody combination of REGN3048 and REGN3051 or ribavirin. Any of these drugs or vaccines can be used in combination or alternation with Compound A Form III provided herein to treat a viral infection susceptible to such.

In certain non-limiting embodiments, Compound A Form III is used in an effective amount in combination with anti-coronavirus vaccine therapy, including but not limited to mRNA-1273 (Moderna, Inc.), AZD-1222 (AstraZeneca and University of Oxford), BNT162 (Pfizer and BioNTech), CoronaVac (Sinovac), NVX-CoV 2372 (NovoVax), SCB-2019 (Sanofi and GSK), ZyCoV-D (Zydus Cadila), CoVaxin (Bharat Biotech), and JNJ-78436735 (also known as Ad26.COV2.S, Janssen). In another embodiment, a compound of the present invention is used in an effective amount in combination with passive antibody therapy or convalescent plasma therapy.

Following entry into a host cell, the SARS-CoV-2 genome is translated by host ribosomes into a long polypeptide which is then cleaved into viral proteins. Two proteases perform this function: the main protease ($M^{Pro}$) and the papain-like protease ($PL^{Pro}$). In certain non-limiting embodiments, Compound A Form III is used in an effective amount in combination with a protease inhibitor In certain non-limiting embodiments, Compound A Form III is used in an effective amount in combination with a SARS-CoV-2 $M^{Pro}$ protease inhibitor. Non-limiting examples of SARS-CoV-2 $M^{Pro}$ protease inhibitors include nirmatrelvir (Paxlovid), GC376, MAC-5576, PF-07304814, and PF-00835231.

To prevent presystemic metabolism of the protease inhibitor, it may be advantageous to administer a CYP3A4 inhibitor in combination with a protease inhibitor. In certain non-limiting embodiments, Compound A Form III is used in an effective amount in combination with a protease inhibitor in addition to a CYP3A4 inhibitor, including but not limited to ritonavir, cobicistat, and ketoconazole.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented, or restored by administering the compound in combination or alternation with another, and perhaps even two or three other, antiviral compounds that induce a different mutation or act through a different pathway, from that of the principal drug.

HCV

For the treatment of HCV, it may be useful to administer Compound A Form III to a host in combination with, for example a:

(1) Protease inhibitor, such as an NS3/4A protease inhibitor;
(2) Another NS5A inhibitor;
(3) Another NS5B polymerase inhibitor;
(4) NS5B non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of additional anti-HCV agents that can be administered in further combination or alternation with Compound A Form III include (i) protease inhibitors such as telaprevir (Incivek®), boceprevir (Victrelis™), simeprevir (Olysio™), paritaprevir (ABT-450), glecaprevir (ABT-493), ritonavir (Norvir), ACH-2684, AZD-7295, BMS-791325, danoprevir, Filibuvir, GS-9256, GS-9451, MK-5172, Ruzasvir (MK-8408), Setrobuvir, Sovaprevir, Tegobuvir, VX-135, VX-222, ALS-220, and voxilaprevir.
(ii) NS5A inhibitor such as ACH-2928, ACH-3102, IDX-719, daclatasvir, ledispasvir, velpatasvir (Epclusa), elbasvir (MK-8742), grazoprevir (MK-5172), and Ombitasvir (ABT-267);
(iii) NS5B inhibitors such as AZD-7295, Clemizole, dasabuvir (Exviera), ITX-5061, PPI-461, PPI-688, sofosbuvir (Sovaldi®), MK-3682, and mericitabine;
(iv) NS5B inhibitors such as ABT-333, and MBX-700;
(v) Antibody such as GS-6624;
(vi) Combination drugs such as Harvoni (ledipasvir/sofosbuvir); Viekira Pak (ombitasvir/paritaprevir/ritonavir/dasabuvir); Viekirax (ombitasvir/paritaprevir/ritonavir); G/P (paritaprevir and glecaprevir); Technivie™ (ombitasvir/paritaprevir/ritonavir), Epclusa (sofosbuvir/velpatasvir), Zepatier (elbasvir and grazoprevir), Mavyret (glecaprevir and pibrentasvir), and Vosevi (Sofosbuvir, velpatasvir, and voxilaprevir).

If Compound A Form III is administered to treat advanced hepatitis C virus leading to liver cancer or cirrhosis, in certain non-limiting embodiments, Compound A Form III can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone decetylace inhibitors, capecitabine, cisplatin, carboplatin, doxorubicin, 5-fluorouracil, gemcitabine, irinotecan, oxaliplatin, topotecan, and other topoisomerases. In certain non-limiting embodiments Compound A Form III is administered in combination with Ruzasvir (MK-8408) to a patient with an HCV infection.

In certain non-limiting embodiments the additional therapeutic agent described above is administered as a pharmaceutically acceptable salt, for example, a salt described below. The term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Treatments for Additional RNA Viruses

Drugs that are currently approved for influenza are Amantadine, Rimantadine, baloxavir marboxil (Xofluza®), oseltamivir phosphate (Tamiflu®), zanamivir (Relenza®), and peramivir (Rapivab®). Any of these drugs can be used in combination or alternation with an active compound provided herein to treat a viral infection susceptible to such.

Currently, there are no approved drugs for West Nile virus. Physicians are recommended to provide intensive support therapy, which may involve hospitalization, intravenous fluids, use of a ventilator to assist breathing, medications to control seizures, brain swelling, nausea and vomiting, and the use of antibiotics to prevent bacterial infections for making the disease even worse. This highlights the importance of the present compounds for viral medical therapy.

In addition, there is no vaccine or specific treatment for the Zika virus. Instead the focus is on relieving symptoms which includes rest, rehydration and acetaminophen for fever and pain.

There is also no vaccine or specific treatment for Dengue fever. Supportive case for those infected include fluid replacement and analgesics, along with acetaminophen, aspirin, and nonsteroidal anti-inflammatory drugs to treat fever and other symptoms.

The Yellow Fever Vaccine (YF-Vax) is manufactured by Sanofi Pasteur, Inc. and is recommended for those aged 9 and older who are traveling to areas of high risk, including South American and Africa. In certain non-limiting embodiments, Compound A Form III is administered to a host in combination with the YF-Vax. No treatment exists for Yellow Fever, but an emphasis is placed on easing fever, muscle pain, and dehydration. Due to the risk of internal bleeding, aspirin and nonsteroidal anti-inflammatory drugs are not recommended.

EXAMPLES

Example 1. Preparation of Compound A Form III

Compound B (150 g) was added to acetone (180 mL) and the mixture was stirred at 20-30° C. to afford a solution. Then, sulfuric acid (12.6 g, 0.5 eq) was slowly added at 15-20° C. and solids gradually precipitated. The mixture was stirred at 15-20° C. for 30 minutes and then stirred at 40-45° C. for 4-5 hours. The mixture was cooled to 25-30° C. and stirred at this temperature for one hour before the mixture was filtered. The resulting cake was rinsed with acetone (150 mL).

The wet material was dissolved in methanol (150 ml) at 30-40° C. Acetone (450 ml) was added and then additional acetone was added slowly at 40-45° C. The mixture was stirred at 40-45° C. for 8-10 hours and then cooled to 25-30° C. The mixture was filtered, and the resulting cake was rinsed with acetone (150 mL). The XRPD pattern of the wet Compound A Form III is shown in FIG. 1 and the peaks are listed in Table 1. The peaks in the table correspond to the numbered peaks in FIG. 1.

The wet material was vacuum-dried at 30-35° C. for 4-5 hours and then vacuum-dried at 50-60° C. for around 15 hours to afford dry Compound A Form III (130 g) in 87% yield. The XRPD pattern of Compound A Form III is shown in FIG. 2 and the peaks are listed in Table 2. The peaks in the table correspond to the numbered peaks in FIG. 2.

TABLE 1

Wet Compound A Form III XRPD Peaks

| Peak No. | 2-Theta | d-spacing (Angstroms) | BG | Height | Height % | Area | Area % | FWHM |
|---|---|---|---|---|---|---|---|---|
| 1 | 5.159 | 17.1143 | 91 | 521 | 100.0 | 8131 | 100.0 | 0.265 |
| 2 | 6.999 | 12.6199 | 72 | 124 | 23.8 | 3071 | 37.8 | 0.421 |
| 3 | 7.260 | 12.1659 | 71 | 161 | 30.9 | 3991 | 49.1 | 0.421 |
| 4 | 8.860 | 9.9719 | 78 | 220 | 42.4 | 4935 | 60.7 | 0.381 |
| 5 | 9.257 | 9.5455 | 88 | 68 | 13.1 | 796 | 9.8 | 0.199 |
| 6 | 9.898 | 8.9284 | 101 | 61 | 11.7 | 967 | 11.9 | 0.269 |
| 7 | 10.337 | 8.5507 | 82 | 130 | 25.0 | 4312 | 53.0 | 0.564 |
| 8 | 10.860 | 8.1396 | 106 | 106 | 20.3 | 1038 | 12.8 | 0.166 |
| 9 | 12.263 | 7.2119 | 111 | 61 | 11.7 | 1982 | 24.4 | 0.552 |
| 10 | 12.959 | 6.8257 | 138 | 96 | 18.4 | 1506 | 18.5 | 0.267 |
| 11 | 13.580 | 6.5153 | 137 | 163 | 31.3 | 4453 | 54.8 | 0.464 |
| 12 | 13.938 | 6.3484 | 142 | 102 | 19.6 | 2069 | 25.4 | 0.345 |
| 13 | 14.661 | 6.0372 | 159 | 113 | 21.7 | 2527 | 31.1 | 0.380 |
| 14 | 16.258 | 5.4473 | 196 | 70 | 13.4 | 2245 | 27.6 | 0.545 |
| 15 | 16.842 | 5.2597 | 196 | 124 | 23.8 | 2864 | 35.2 | 0.393 |
| 16 | 17.215 | 5.1466 | 191 | 71 | 13.6 | 2286 | 35.5 | 0.691 |
| 17 | 18.138 | 4.8868 | 173 | 101 | 19.41 | 2295 | 28.2 | 0.386 |
| 18 | 19.882 | 4.4619 | 254 | 238 | 45.7 | 5376 | 66.1 | 0.384 |
| 19 | 20.718 | 4.2387 | 282 | 68 | 13.1 | 1304 | 16.0 | 0.326 |
| 20 | 20.999 | 4.2270 | 292 | 66 | 12.7 | 1307 | 16.1 | 0.337 |
| 21 | 21.760 | 4.0809 | 288 | 266 | 51.1 | 6026 | 74.1 | 0.385 |
| 22 | 22.764 | 3.9031 | 258 | 58 | 11.1 | 523 | 6.4 | 0.153 |
| 23 | 24.719 | 3.5988 | 216 | 140 | 26.9 | 3376 | 41.5 | 0.410 |
| 24 | 25.989 | 3.4256 | 191 | 69 | 13.2 | 888 | 10.9 | 0.219 |
| 25 | 31.559 | 2.8326 | 123 | 59 | 11.3 | 801 | 9.9 | 0.231 |

TABLE 2

Dry Compound A Form III XRPD Peaks

| Peak No. | 2-Theta | d-spacing (Angstroms) | BG | Height | Height % | Area | Area % | FWHM |
|---|---|---|---|---|---|---|---|---|
| 1 | 5.180 | 17.0458 | 73 | 517 | 100.0 | 7821 | 100.0 | 0.257 |
| 2 | 6.965 | 12.6814 | 72 | 100 | 19.3 | 2589 | 33.1 | 0.440 |
| 3 | 7.340 | 12.0343 | 72 | 158 | 30.6 | 3452 | 44.1 | 0.371 |
| 4 | 8.921 | 9.9040 | 69 | 229 | 44.3 | 5095 | 65.1 | 0.378 |
| 5 | 9.297 | 9.5049 | 75 | 71 | 13.7 | 1013 | 13.0 | 0.243 |
| 6 | 9.962 | 8.8720 | 92 | 76 | 14.7 | 1355 | 17.3 | 0.303 |
| 7 | 10.360 | 8.5315 | 75 | 131 | 25.3 | 4363 | 55.8 | 0.566 |
| 8 | 10.921 | 8.0944 | 95 | 99 | 19.1 | 1130 | 14.4 | 0.194 |
| 9 | 11.539 | 7.6622 | 88 | 44 | 8.5 | 1380 | 17.6 | 0.533 |
| 10 | 12.259 | 7.2138 | 113 | 61 | 11.8 | 1742 | 22.3 | 0.485 |
| 11 | 12.998 | 6.8057 | 144 | 96 | 18.6 | 1077 | 13.8 | 0.191 |
| 12 | 13.561 | 6.5239 | 127 | 173 | 33.5 | 4822 | 61.7 | 0.474 |
| 13 | 13.901 | 6.3654 | 138 | 90 | 17.4 | 2585 | 33.1 | 0.488 |
| 14 | 14.739 | 6.0053 | 144 | 142 | 27.5 | 2838 | 36.3 | 0.340 |
| 15 | 15.016 | 5.8950 | 150 | 98 | 19.0 | 2844 | 36.4 | 0.493 |
| 16 | 15.614 | 5.6707 | 164 | 80 | 15.5 | 1074 | 13.7 | 0.228 |
| 17 | 16.241 | 5.4531 | 178 | 94 | 18.2 | 2540 | 32.5 | 0.459 |
| 18 | 16.958 | 5.2243 | 173 | 153 | 29.6 | 3419 | 43.7 | 0.380 |
| 19 | 17.281 | 5.1273 | 166 | 92 | 17.8 | 1876 | 24.0 | 0.347 |
| 20 | 18.161 | 4.8806 | 162 | 116 | 22.4 | 2941 | 37.6 | 0.431 |
| 21 | 19.879 | 4.4625 | 249 | 219 | 42.4 | 5302 | 67.8 | 0.412 |
| 22 | 20.678 | 4.2919 | 277 | 69 | 13.3 | 1158 | 14.8 | 0.285 |
| 23 | 21.078 | 4.2114 | 293 | 87 | 16.8 | 1162 | 14.9 | 0.227 |
| 24 | 21.820 | 4.0699 | 282 | 264 | 51.1 | 5395 | 69.0 | 0.347 |
| 25 | 22.829 | 3.8922 | 238 | 86 | 16.6 | 798 | 10.2 | 0.158 |
| 26 | 23.452 | 3.7901 | 233 | 53 | 10.3 | 244 | 3.1 | 0.078 |
| 27 | 24.882 | 3.5755 | 219 | 107 | 20.7 | 2090 | 26.7 | 0.332 |
| 28 | 26.021 | 3.4215 | 184 | 54 | 10.4 | 897 | 11.5 | 0.282 |
| 29 | 31.640 | 2.8255 | 118 | 52 | 10.1 | 864 | 11.0 | 0.282 |

Alternatively, Compound A Form III was also prepared by charging Compound A (2 g) in a mixture of methanol (4 ml) and acetone (24 ml). The mixture was stirred at 30° C. for 20 hours. Following filtration, the wet material was dried at 60° C. without vacuum for 20 hours to afford Compound A Form III (1.7 g, yield 85%).

Example 2. Preparation of Additional Compound A Morphic Forms

Figure 3:
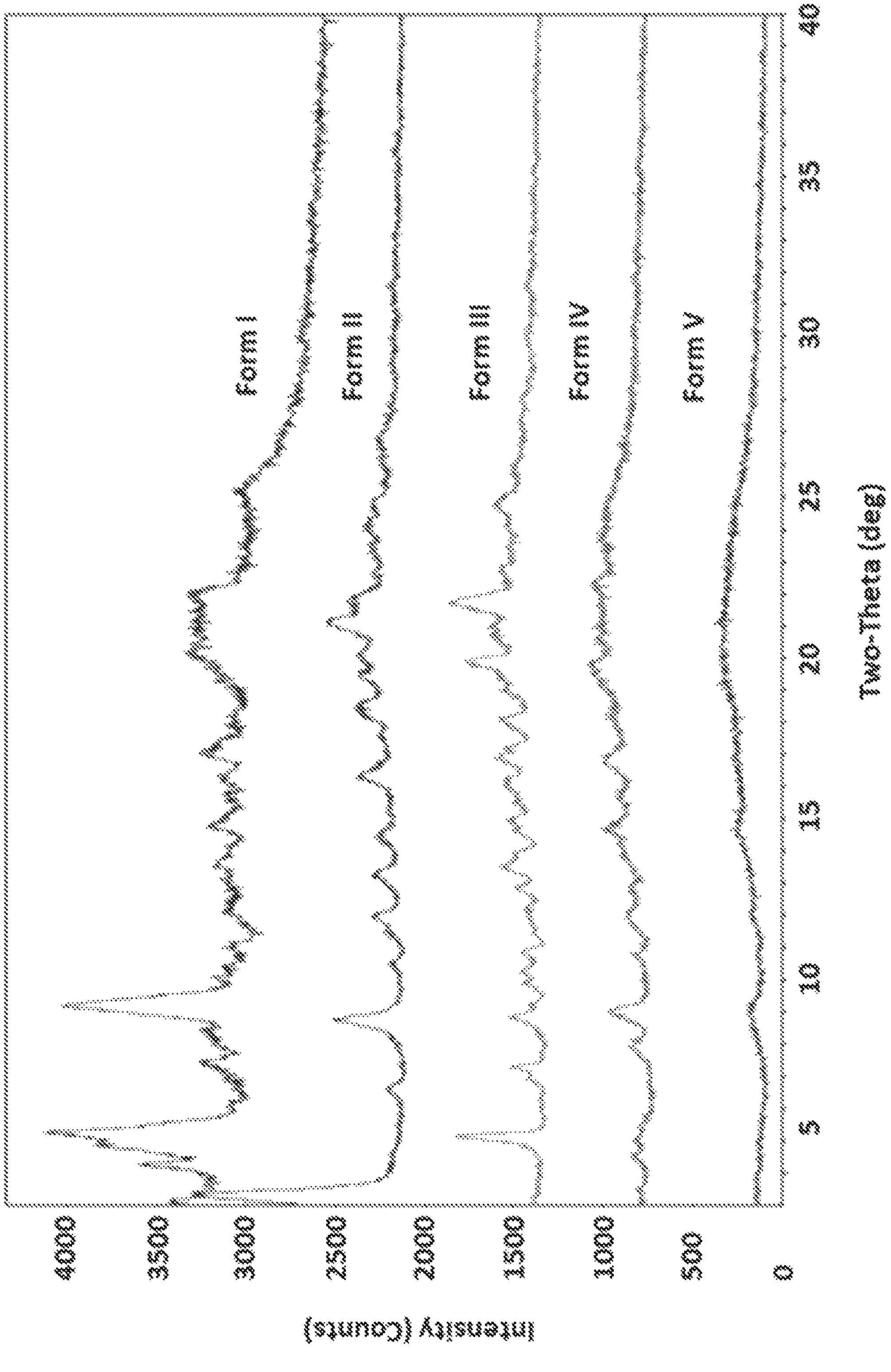
FIG. 3 is an overlay of the XRPD patterns of Compound A Form I, Form II, Form III, Form IV, and Form V as described in Example 2. Compound A Form III is crystalline, while Forms I-II and IV-V are more amorphous in character. The x-axis is 2Theta measured in degrees and the y-axis is intensity measured in counts.

In addition to Form III, four other morphic forms of Compound A, Forms I-II and IV-V, were prepared. The solvent and conditions for each of the Forms is provided in Table 3 and the analytic results for each Form are in Table 4. An XRPD overlap of the five Forms is shown in FIG. 3. The preparation for each Form is described below.

TABLE 3

Description and Conditions of Compound A Morphic Forms I-V

| | Description | Solvent & Condition | Drying | Quantity & Yield |
|---|---|---|---|---|
| Form I | Mixture of Form I and amorphous. The ratio cannot be well controlled. | Make Compound A from Compound B Methanol/acetone, crystallized at 30-40° C. | Without vacuum | 40 g, 75% |
| Form II | Mixture of Form II and amorphous. The reproducibility is poor. | Recrystallized from iopropanol/isopropyl acetate at 50-55° C. | Vacuum | 45 g, 90% |
| Form III | Mixture is crystalline and contains a small amount of amorphous. | Recrystallized from methanol/acetone at 45-50° C. | Vacuum | 90 g, 90% |
| Form IV | Mixture of Form IV and amorphous. | Slurry form I in methyl acetate at around 55° C. | Vacuum | 105 g, 87.5% |
| Form V | Most of the material is amorphous. | Slurry form I in ethyl acetate at around 78° C. Make Compound A from Compound B in ethyl acetate | Vacuum | 96 g, 96% |

TABLE 4

Analytical Results of Compound A Morphic Forms I-V

| | Particle size (um) | | | Density(g/ml) | | Purity | |
|---|---|---|---|---|---|---|---|
| | $D_{10}$ | $D_{50}$ | $D_{90}$ | Bulk | Tapped | (%) | KF (%) |
| Form I | / | / | / | 0.31 | 0.52 | 99.83 | 1.76 |
| Form II | 0.98 | 3.50 | 18.6 | 0.12 | 0.17 | 99.95 | / |
| Form III | 0.96 | 2.68 | 12.5 | 0.17 | 0.26 | 99.92 | |
| Form IV | 1.01 | 4.51 | 36.2 | 0.25 | 0.49 | 99.95 | / |
| Form V | 1.1 | 6.48 | 264 | 0.204 | 0.298 | 99.94 | 1.27 |
| | 0.80 | 2.44 | 15.2 | 0.122 | 0.275 | | |

Form I

Figure 4:
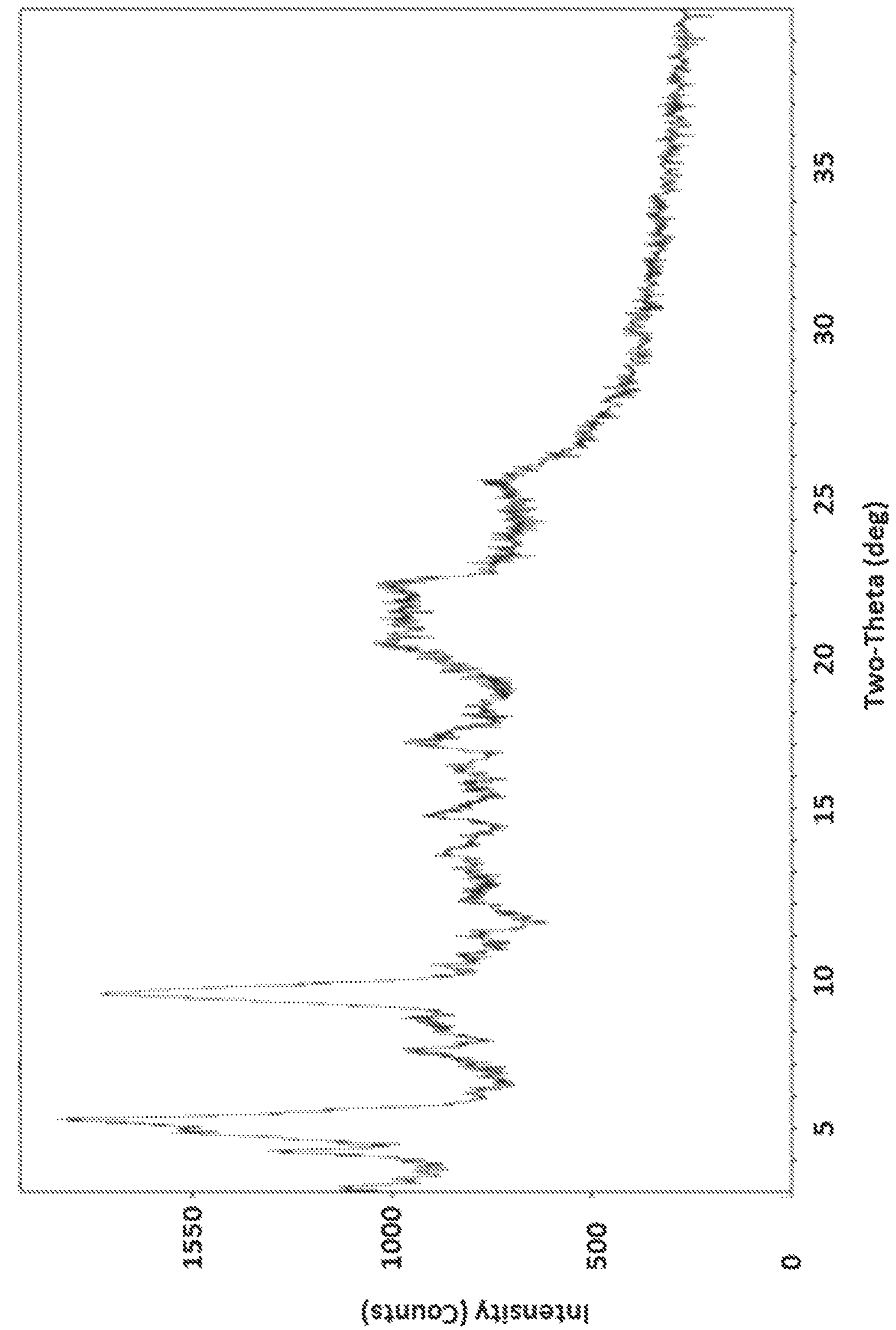
FIG. 4 is the XRPD pattern of dry Compound A Form I as described in Example 2. The x-axis is 2Theta measured in degrees and the y-axis is intensity measured in counts.

Compound B (50 g) was charged to methanol (100 mL) and acetone (150 mL). The mixture was heated to around 50° C. to afford a clear solution. Sulfuric acid (4 g) was slowly added and the mixture remained a solution. After acetone (600 mL) was slowly charged at 50-55° C., the mixture was cooled to 25-30° C. and stirred at this temperature for 16-20 hours. The white solids started to precipitate at 36° C. Then the solids were collected by suction, and the cake was rinsed by a mixed solvent of methanol and acetone (10+150 mL). The material was dried at 55° C. for 18 hours without vacuum to afford 40 g of Compound A Form I in a yield of 7500. The XR-PD pattern for Form I is shown in FIG. 4.

Alternatively, Form I was also prepared by adding Compound B (5 g) to acetone (60 mL). The mixture was stirred at 20-30° C. to afford a clear solution. Sulfuric acid (0.42 g, 0.5 eq) was slowly added at 15-20° C. The solids were gradually precipitated during the addition. The mixture was stirred at 15-20° C. for 30 minutes and then stirred at 30-45° C. for 2 hours. The mixture was cooled to 25° C. Following filtration, the cake was rinsed with acetone (10 mL). The wet material was dried at 40° C. without vacuum for 2 hours and then dried at 60° C. without vacuum for 20 hours to afford Compound A Form I (4.8 g, yield 96%).

Form II

Figure 5:
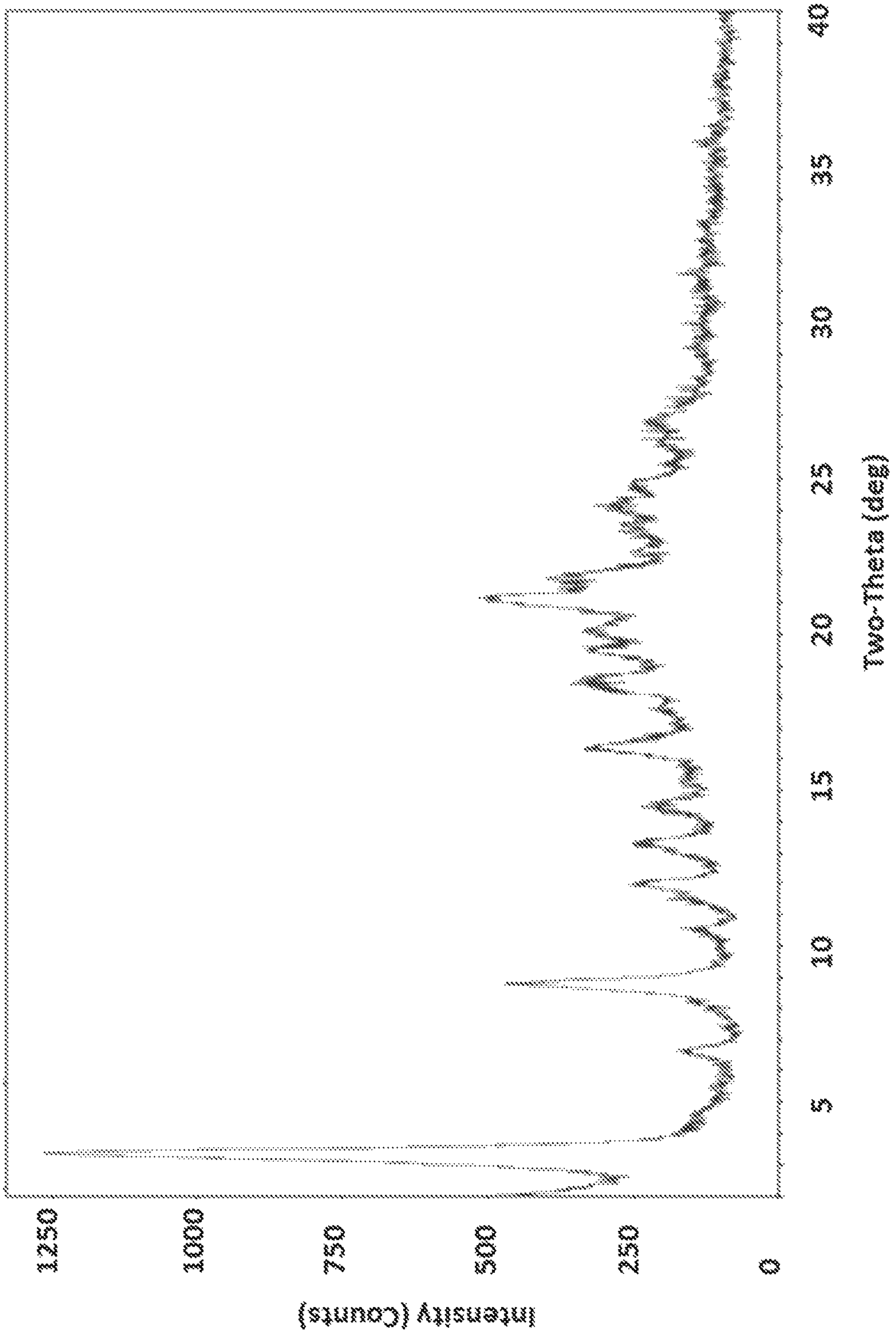
FIG. 5 is the XRPD pattern of dry Compound A Form II as described in Example 2. The x-axis is 2Theta measured in degrees and the y-axis is intensity measured in counts.

Compound A (50 g) was charged to isopropanol (500 mL) and the mixture was heated to 50-55° C. to afford a clear solution. Then isopropyl acetate (250 mL) was added slowly and the mixture remained a solution. Compound A (100 mg) seed was added. After stirring for 1 hour, some solid precipitated gradually, and then isopropyl acetate (250 mL) was added slowly. After the mixture was stirred at 45-50° C. for 20 hours, the heating was stopped and temperature was slowly decreased to about 25-30° C. Then solid was filtered, washed with isopropyl acetate (50 mL) and dried at 25-30° C. in vacuum for 4 hours. Then the material was milled and continued to be dried at 60° C. in vacuum for 16 hours to afford Compound A Form II (45 g, 90% yield). The XRPD pattern for Form II is shown in FIG. 5.

Form III

In an alternative to the procedure describe in Example 1, Compound A (100 g) was charged to methanol (100 mL) and the mixture was heated to 50° C. to afford a clear solution. Then acetone (300 mL) was slowly added at 45-50° C. The system remained completely dissolved after dropping. Then 100 mg seed of Compound A Form III was added. After stirring for 1 hour, the solid precipitated gradually. Acetone (300 mL) was slowly added with stirring at 45-50° C. in 1 hour. After the addition, the mixture was stirred at 40-45° C. for 18 hours. The heating was then stopped and temperature was slowly decreased to about 25-30° C. The solid was filtered, washed with acetone (100 mL) and dried at 60° C. in vacuum for 16 hours to afford 90 g Compound A Form III in 90% yield.

Form IV

Figure 6:
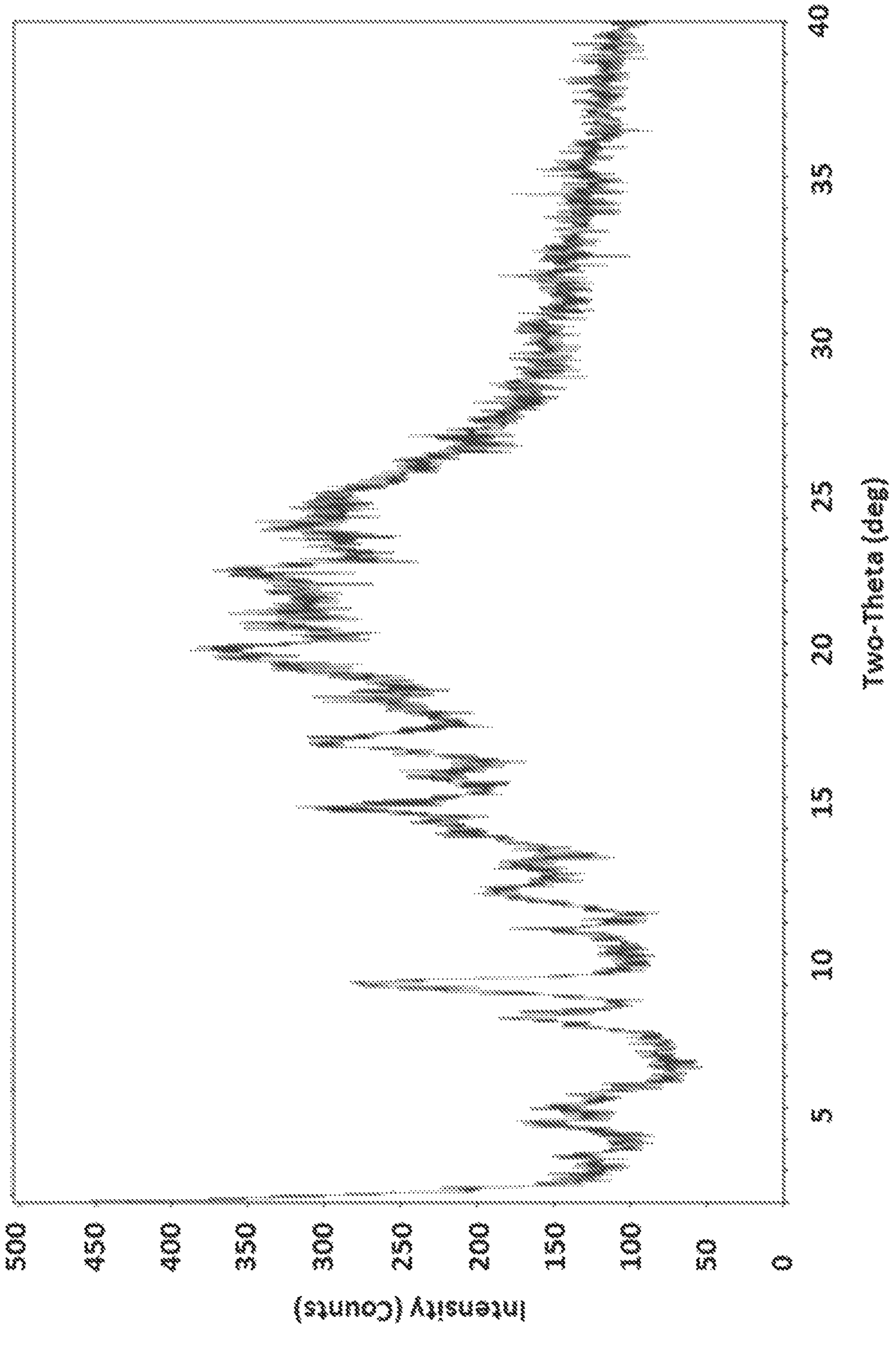
FIG. 6 is the XRPD pattern of dry Compound A Form IV as described in Example 2. The x-axis is 2Theta measured in degrees and the y-axis is intensity measured in counts.

Compound A (120 g) was charged to methyl acetate (1200 mL) and the mixture was then slurried at around 55° C. for 20 hours. Then the heating was stopped and temperature was slowly decreased to about 25-30° C. Then the solid was filtered, washed with methyl acetate (100 mL) and dried at 60° C. in vacuum for 18 hours to afford 105 g Compound A Form IV in 87.5% yield. The XRPD pattern for Form IV is shown in FIG. 6.

Form V

Figure 7:
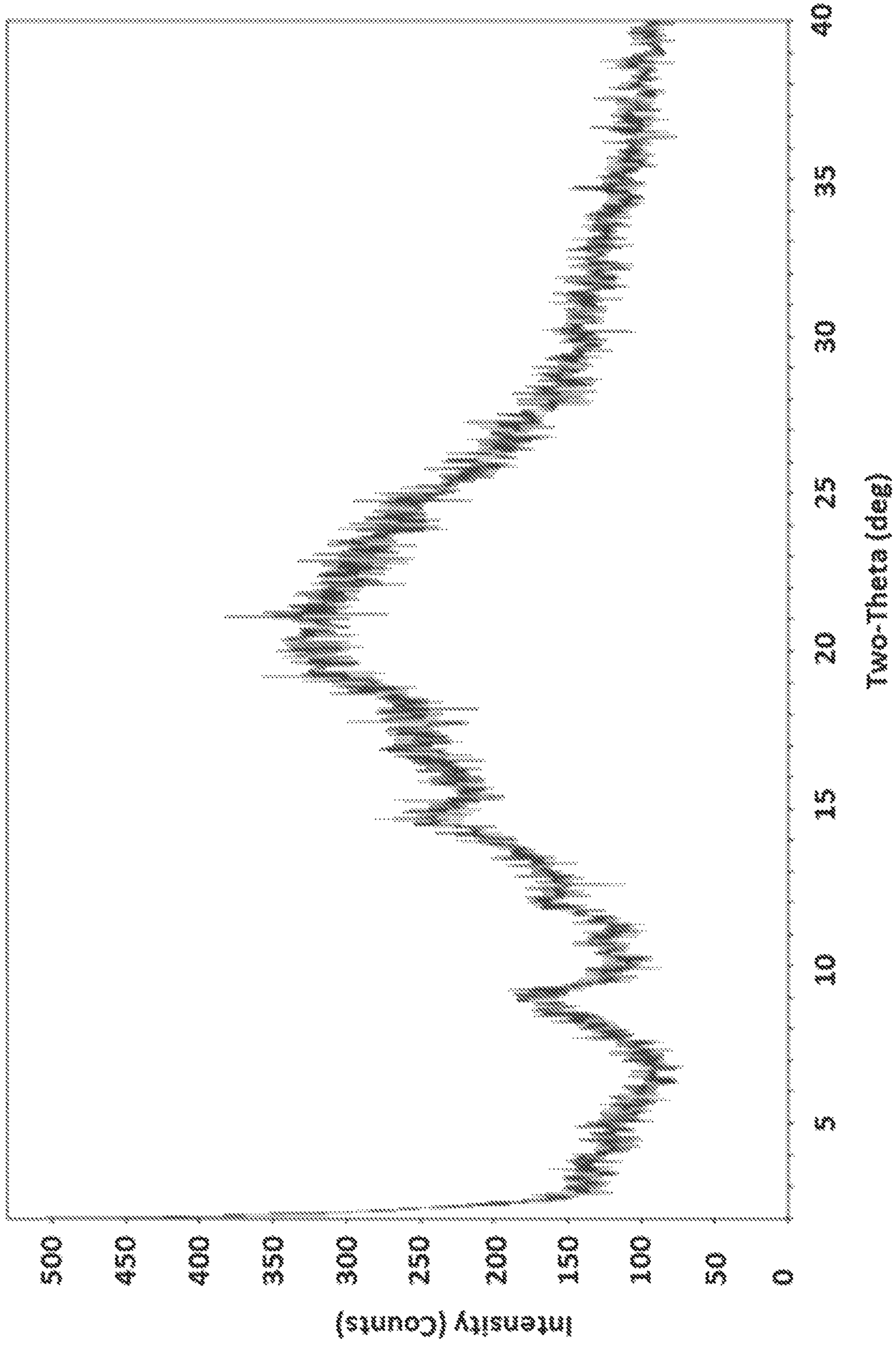
FIG. 7 is the XRPD pattern of dry Compound A Form V as described in Example 2. The x-axis is 2Theta measured in degrees and the y-axis is intensity measured in counts.

Compound A (100 g) was charged to ethyl acetate (1000 mL) and the mixture was then slurried at around 78° C. for 20 hours. Then the heating was stopped and temperature was slowly decreased to about 25-30° C. Then the solid was filtered, washed with ethyl acetate (100 mL) and dried at 60° C. in vacuum for 16 hours to afford 96 g of Compound A Form V in 96% yield. The XRPD pattern for Form V is shown in FIG. 7.

In an alternative procedure, Compound B (75 g) was added to ethyl acetate (750 mL), and the mixture was heated to 60-65° C. to afford a clear solution. Then sulfuric acid (6.45 g, 0.5 eq) was slowly added at 60-65° C. without dilution, and the solids gradually precipitated during the addition. The resulting mixture was heated to around 78° C. and then stirred at this temperature for 20 hours. Then the mixture was cooled to 25-30° C. and stirred at this temperature for 3 hours. The white solids were collected by suction, and the cake was rinsed by ethyl acetate (100 mL). After the drying at 60° C. without vacuum for 5 hours, the material was milled using blade mill. The material was again dried at 55° C. without vacuum for 16 hours.

Example 3. Preparation of Compound A Form III on Large Scale from Compound A

To a 5 L round bottom flask equipped with a mechanical stirrer was charged acetone (3200 g, 4000 mL, 10 V) at 20-30° C. Next, Compound A (200 g) was added, providing a suspension. Then the mixture was heated and stirred for 1 hour at 55-58° C. before adding a second charge of Compound A (200 g) over 5 minutes. The mixture was heated and stirred for 16 hours at 55-58° C., then cooled to 20-25° C. in a period of 4 hours and stirred for another 2 hours at 20-25° C. The solid was filtered (controlling the environmental humidity at ≤40%) then rinsed by acetone (400 mL, 1 vol) to afford Compound A as a wet cake (980 g)

Figure 8:
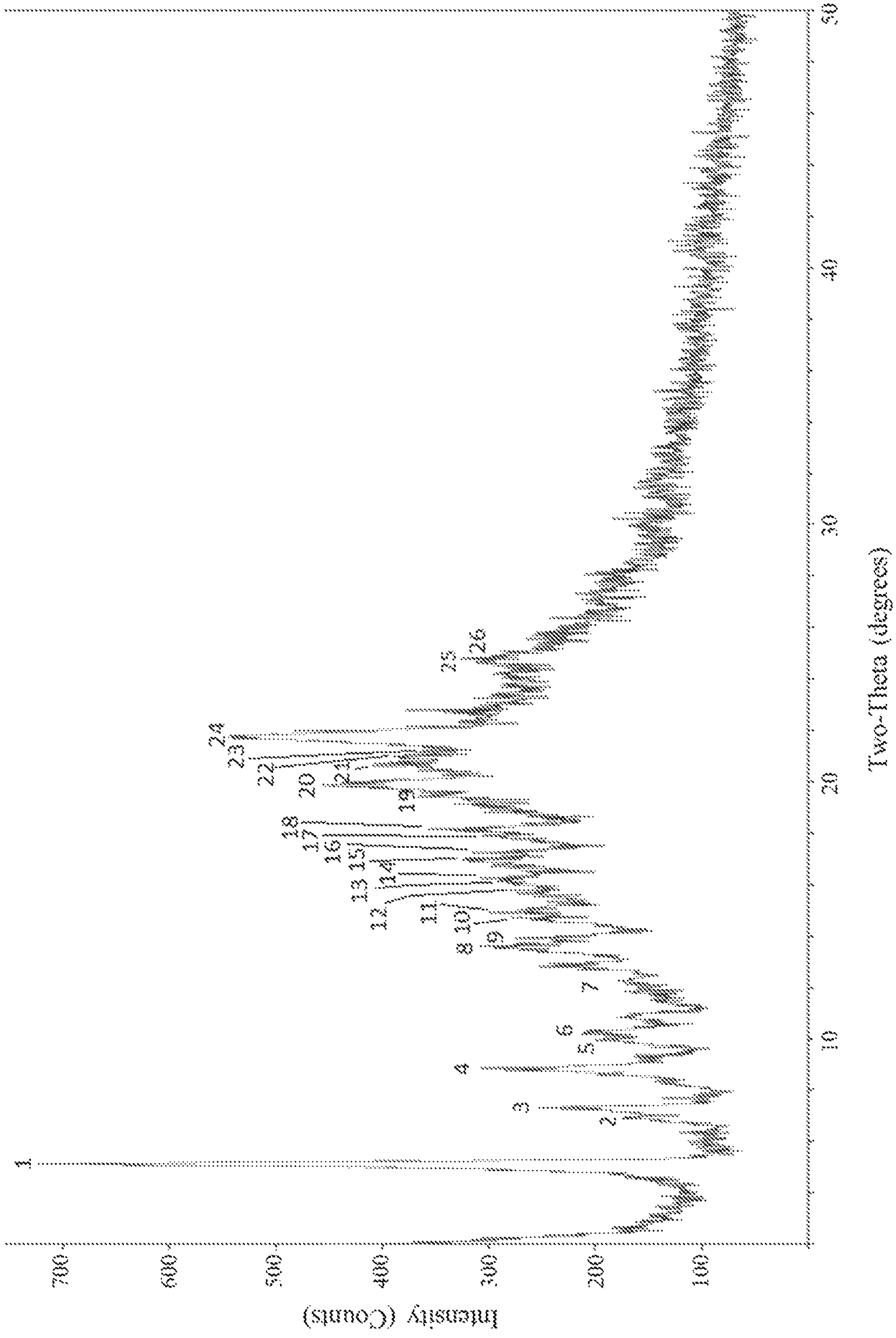
FIG. 8 is the XRPD pattern of dry Compound A Form III as described in Example 3. The x-axis is 2Theta measured in degrees and the y-axis is intensity measured in counts.

A 10 L four-neck glass flask was equipped with a thermometer and n-heptane (6000 ml) was charged into the flask at 10-20° C. Compound A (980 g, wet cake) was charged in one portion at 10-20° C. The mixture was stirred for 2 hours at 0-5° C. The solid was collected by filtration to give wet cake as white solid (1.1 kg). The wet cake was put in two trays (30*40 cm) and dried in a vacuum oven (−0.09 MPa) at 35° C. for 20 hours. Drying was continued at 55° C. under vacuum (−0.09 MPa) for 8 hours. Drying was continued at 55° C. in vacuum (−0.090 MPa) for 16 hours to afford Compound A Form III in 90% yield. The XRPD pattern for the product of Example 3 is shown in FIG. 8.

Example 4. Preparation of Compound A Form III on Large Scale from Compound B

To a 5 L three-necked glass flask equipped with mechanical stirrer, addition funnel, and thermometer was charged acetone (2000 g, 2500 mL, 10 V) at an internal temperature of 20-30° C. Compound B (250 g, 90% assay by titration) was charged in one portion with stirring. After stirring for about 5 mins at 20-30° C., a clear solution was formed. Then, charcoal (7.5 g) was charged to the solution and the resulting mixture was stirred for 30 minutes at 20-30° C. The charcoal was filtered and washed with acetone (200 g, 250 mL, 1 V).

The filtrate was added to a 5 L three-necked glass flask. Sulfuric acid (98% w/w, 19.3 g, 0.5 eq.) was added to the solution dropwise over 2 hours at 20-30° C. The suspension was aged at 20-25° C. for 30 minutes, then heated to 55-58° C. and aged for 16 hours. Then the suspension was cooled to 25° C. within 3 hrs (cooling rate 5-10° C./hour) and aged for 1 hr at 25° C. The solid was filtered (keeping the humidity below 40%). The wet cake was washed with acetone (400 g, 500 mL, 2V) at ambient temperature to afford Compound A wet cake (480 g).

Figure 9:
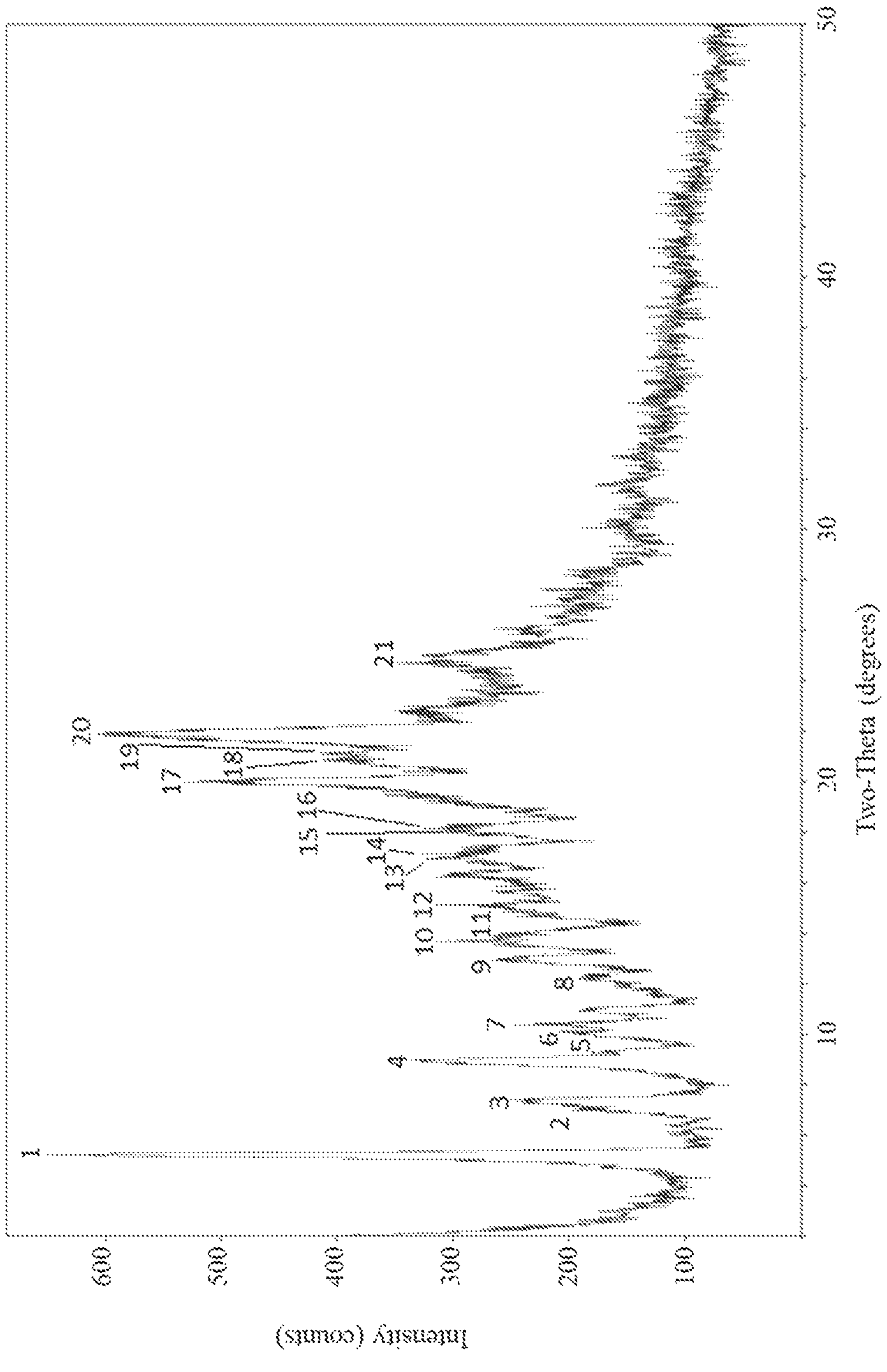
FIG. 9 is the XRPD pattern of dry Compound A Form III as described in Example 4. The x-axis is 2Theta measured in degrees and the y-axis is intensity measured in counts.

To a 10 L four-neck glass flask equipped with a thermometer was charged n-Heptane (3750 ml) at 10-20° C. Compound A wet cake (480 g) was added to the reactor in one portion at 10-20° C. The mixture was stirred for 2 hours at 0-5° C. The solid was collected by filtration to give Compound A (450 g, wet cake) as an off-white solid. The wet cake was loaded onto trays and dried at 35° C. in a vacuum oven (−0.09 MPa) for 20 hours. The oven temperature was raised to 50° C. and the compound dried under vacuum (−0.09 MPa) for 8 hours. Drying was continued at 50° C. in vacuum (−0.09 MPa) for 16 hours to afford Compound A Form III (yield: 85%). The XRPD pattern of the product of Example 4 is shown in FIG. 9.

Example 5. Dissolution Rates of Compound a Tablets Produced Using Amorphous API Vs Tablets Made from Form III API Dissolution was determined by United States Pharmacopeia <711> standardized solubility assay, using a basket apparatus (USP Apparatus I). The Compound A Form III and Compound A amorphous tablets described above were dissolved in 0.1 N HCl in the USP Apparatus I. Samples were taken at various time points and analyzed by UHPLC-UV to quantify the amount of Compound A that had dissolved.

The conditions are provided below.

| Component | Condition |
|---|---|
| Apparatus | USP Apparatus I, Basket |
| Medium | 0.1N HCl |
| Volume | 900 mL |
| Rotation Speed | 100 RPM |
| Temperature | 37° C. ± 0.5° C. |
| Sampling Time Point (min) | 5, 10, 15, 20, 30, 45, 60 and 75 |

Conditions for UHPLC Detection and Determination of Dissolution Rates

| Component | Condition |
|---|---|
| Column | 3.0 × 100 mm, 2.7 mm particle size |
| Column Packing | C18 |
| Column Temp | 30° C. |
| Sample Temp | 5° C. |
| UV detection | 254 nm |
| Flow rate | 0.6 mL/min |
| Injection volume | 1.0 mL |
| Mobile Phase A | 0.1% phosphoric acid in water |
| Mobile phase B | Acetonitrile |
| Diluent | Water:Acetonitrile = 90:10 (V/V), for standard solution prep |
| Retention Time | AT-527: ~2 minutes<br>Degradation peak: ~1.8 minutes |

Gradient for UHPLC Assay

| Time (Min) | % A | % B |
|---|---|---|
| 0.0 | 85 | 15 |
| 0.5 | 85 | 15 |
| 2.0 | 20 | 80 |
| 2.1 | 85 | 15 |
| 5.0 | 85 | 15 |

| Dissolution Rate Data from Solubility Assay | | |
|---|---|---|
| Time (minutes) | % Dissolved (Form III) | % Dissolved (Amorphous) |
| 10 | 89 | 27 |
| 20 | 99 | 64 |
| 30 | 100 | 68 |
| 45 | 99 | 94 |
| 60 | 99 | 99 |

The tablets used in the dissolution rate study were prepared according to the following method:

| Ingredient | Composition: Amorphous API Tablet (% w/w) | Composition: Form III API Tablet (% w/w) |
|---|---|---|
| Intragranular | | |
| Compound A (spray-dried amorphous) | 49.7 | N/A |
| Compound A (Form III) | N/A | 49.7 |
| Silicified microcrystalline cellulose (SMCC) | 21.3 | 21.3 |
| Mannitol | 13.5 | 13.5 |
| Croscarmellose sodium | 4.5 | 4.5 |
| Colloidal silicon dioxide | 1.0 | 1.0 |
| Magnesium stearate | 0.5 | 0.5 |
| Extragranular | | |
| Silicified microcrystalline cellulose (SMCC) | 5.0 | 5.0 |
| Croscarmellose sodium | 3.5 | 3.5 |
| Magnesium stearate | 1.0 | 1.0 |
| Total Composition (% w/w) | 100.0 | 100.0 |
| Tablet Weight | 600 mg | 600 mg |

Granule Preparation:

To a v-blender was added half of the SMCC, the colloidal silicon dioxide, and half of the croscarmellose sodium. The mixture was then blended. To this mixture was added the mannitol, and the resulting mixture blended and screened. The magnesium stearate was screened, and then added to the blend and blended. The blend was then collected and granulated.

Tablet Preparation:

The granules were added to a v-blender, followed by screened croscarmellose sodium and SMCC. The mixture was blended and then screened magnesium stearate was added. The resulting mixture was blended and then compressed into tablets.

Example 6. Stability of 5 kg Lot of Form III at 25° C.±2° C., 60% RH±5% RH

| | 0 Months | 1 Month | 2 Months | 3 Months |
|---|---|---|---|---|
| Appearance | White powder | White powder | White powder | White powder |
| Purity (HPLC-UV, a/a) | 99.9% | 99.9% | 99.9% | 99.9% |
| Impurities (HPLC-UV, a/a) | <0.05% | <0.05% | <0.05% | <0.05% |
| Water (KF) | 0.86% | 0.98% | 0.87% | 0.91% |
| XRPD | Form III | Form III | Form III | Form III |
| Particle Size Distribution | Dv(10) = 0.74 μm<br>Dv(50) = 3.19 μm<br>Dv(90) = 21.0 μm | Dv(10) = 0.70 μm<br>Dv(50) = 2.96 μm<br>Dv(90) = 20.4 μm | Dv(10) = 0.70 μm<br>Dv(50) = 2.79 μm<br>Dv(90) = 16.8 μm | Dv(10) = 0.83 μm<br>Dv(50) = 3.62 μm<br>Dv(90) = 23.5 μm |
| Bulk Density | 0.134 g/mL | 0.139 g/mL | 0.137 g/mL | 0.141 g/mL |
| Tapped Density | 0.202 g/mL | 0.232 g/mL | 0.333 g/mL | 0.305 g/mL |

When measured by HPLC-UV, Compound A Form III shows no measurable degradation over the course of three months when stored at about 25° C. and about 60% RH. This advantageous chemical stability is an improvement over the amorphous form of the compound, including the spray-dried amorphous form, which requires refrigerated storage. Compound A Form III also does not appreciably absorb water from the atmosphere or change density upon storage. These properties are advantageous for use in clinical trials or clinical use of the compound.

Example 7. Stability of 5 kg Lot of Form III at 40° C.±2° C., 75% RH±5% RH

| | 0 Months | 1 Month | 2 Months | 3 Months |
|---|---|---|---|---|
| Appearance | White powder | White powder | White powder | White powder |
| Purity (HPLC-UV, a/a) | 99.9% | 99.9% | 99.9% | 99.9% |
| Impurities (HPLC-UV, a/a) | <0.05% | <0.05% | <0.05% | <0.05% |
| Water (KF) | 0.86% | 1.04% | 0.91% | 0.76% |
| XRPD | Form III | Form III | Form III | Form III |
| Particle Size Distribution | Dv(10) = 0.74 μm Dv(50) = 3.19 μm Dv(90) = 21.0 μm | Dv(10) = 0.68 μm Dv(50) = 2.82 μm Dv(90) = 21.0 μm | Dv(10) = 0.68 μm Dv(50) = 2.64 μm Dv(90) = 15.8 μm | Dv(10) = 0.77 μm Dv(50) = 3.24 μm Dv(90) = 21.3 μm |
| Bulk Density | 0.134 g/mL | 0.121 g/mL | 0.127 g/mL | 0.139 g/mL |
| Tapped Density | 0.202 g/mL | 0.207 g/mL | 0.318 g/mL | 0.278 g/mL |

Further studies on the stability of Compound A Form III were conducted at elevated temperature and humidity. These conditions are less desirable for the storage of active pharmaceutical ingredients and may lead to accelerated degradation. However, even under these conditions, the Compound A Form III showed no measurable degradation over three months.

Example 8. Stability of 0.1 kg Lot of Form III

| | 25° C. ± 2° C., 60% RH ± 5% RH | | | | |
|---|---|---|---|---|---|
| | 0 Weeks | 1 Week | 2 Weeks | 4 Weeks | 8 Weeks |
| Appearance | White solid | White solid | White solid | White solid | White solid |
| Purity (HPLC-UV, a/a) | 99.96% | 99.96% | 99.97% | 99.94% | 99.93% |
| XRPD | Form III | Form III | Form III | Form III | Form III |

Additional stability studies were performed for smaller lots of Compound A Form III. These studies were performed in stability chambers set to 25° C. and 60% RH, 40° C. and 75% RH for up to 8 weeks. In other embodiments the studies can be performed for up to 4 weeks, for up to 2 weeks and for one week. The stability studies were also performed under ambient conditions, 15-25° C. with no control over the humidity. This study was performed for 12 months and there was no measurable decrease in the purity of the Compound A Form III.

| 40° C. ± 2° C., 75% RH ± 5% RH | | | | | |
|---|---|---|---|---|---|
| | 0 Weeks | 1 Week | 2 Weeks | 4 Weeks | 8 Weeks |
| Appearance | White solid | White solid | White solid | White solid | White solid |
| Purity (HPLC-UV, a/a) | 99.96% | 99.96% | 99.97% | 99.94% | 99.93% |
| XRPD | Form III | Form III | Form III | Form III | Form III |

| Ambient (15° C.-25° C., ambient RH, not in stability chamber) | | |
|---|---|---|
| | 0 Days | 365 Days |
| Appearance | White solid | White solid |
| Purity (HPLC-UV, a/a) | 99.96% | 99.96% |
| XRPD | Form III | Form III |

Example 9. Compound A Form III Pharmaceutical Composition 1

| | | Non-Purity Adjusted | | Purity Adjusted | |
|---|---|---|---|---|---|
| Ingredient | Chemical Name | mg/dose | % w/w | mg/dose | % w/w |
| Intragranular | | | | | |
| Compound A Form III | | 596.4 | 49.7% | 603.7 | 50.3% |
| Pearlitol 100 SD | Mannitol | 162.0 | 13.5% | 154.7 | 12.9% |
| Prosolv SMCC 90 LM | Silicified microcrystalline cellulose | 255.6 | 21.3% | 255.6 | 21.3% |
| Aerosil 200 | Colloidal silicon dioxide | 12.0 | 1.0% | 12.0 | 1.0% |
| Ac-Di-Sol SD-711 | Croscarmellose sodium | 54.0 | 4.5% | 54.0 | 4.5% |
| LIGAMED MF-2-V | Magnesium stearate | 6.0 | 0.5% | 6.0 | 0.5% |
| Extragranular | | | | | |
| Prosolv SMCC 90 LM | Silicified microcrystalline cellulose | 60.0 | 5.0% | 60.0 | 5.0% |
| Ac-Di-Sol SD-711 | Croscarmellose sodium | 42.0 | 3.5% | 42.0 | 3.5% |
| LIGAMED MF-2-V | Magnesium stearate | 12.0 | 1.0% | 12.0 | 1.0% |

To a v-blender was added half of the Prosolv SMCC 90 LM and blended for one minute. To this was added Compound A Form III, Aerosil 200, Ac-Di-Sol SD-711, and the second half of the Prosolv SMCC 90 LM. The mixture was then blended 3 minutes. The Pearlitol 100 SD was added and the resulting mixture blended for 3 minutes. The mixture was then screened through a US 12 mesh screen. The Ligamed MF-2V was then screened through a US 20 mesh screen and added to the blend. The resulting mixture was blended for 2 minutes. The resulting mixture was double bagged with desiccant packs inserted between bags and sealed in a drum for storage.

A roller compactor was set up with smooth rollers, a micro hopper, 1.0 mm screen, 2 mm gap width, a compaction force of 5 kN/cm and a roller speed of 1 revolution/minute. The Compound A blend was then added to the hopper, refilling as necessary during processing. The material from the roller compactor was collected in the dry granulation bag.

The extragranular Ac-Di-Sol SD-711 and Prosolv SMCC 90 LM was screened through a US 12 mesh screen and blended with the granulated material for 3 minutes. Next, LIGAMED MF-2-V was screened through a US 20 mesh screen and added to the blend. The resulting mixture was blended for 2 minutes.

Example 10. Compound A Form III Pharmaceutical Composition 2

| | | Non-Purity Adjusted | | Purity Adjusted | |
|---|---|---|---|---|---|
| Ingredient | Chemical Name | mg/dose | % w/w | mg/dose | % w/w |
| Intragranular | | | | | |
| Compound A Form III | | 596.4 | 49.7% | 603.7 | 50.3% |
| Emcompress (anhydrous) | Anhydrous dibasic calcium hydrogen phosphate | 104.4 | 8.7% | 102.6 | 8.5% |
| Vivapur 105 | Microcrystalline cellulose | 313.2 | 26.1% | 307.7 | 25.6 |
| Aerosil 200 | Colloidal silicon dioxide | 12.0 | 1.0% | 12.0 | 1.0% |
| Ac-Di-Sol SD-711 | Croscarmellose sodium | 54.0 | 4.5% | 54.0 | 4.5% |
| LIGAMED MF-2-V | Magnesium stearate | 6.0 | 0.5% | 6.0 | 0.5% |

-continued

| Ingredient | Chemical Name | Non-Purity Adjusted mg/dose | % w/w | Purity Adjusted mg/dose | % w/w |
|---|---|---|---|---|---|
| Extragranular | | | | | |
| Prosolv SMCC 90 LM | Silicified microcrystalline cellulose | 60.0 | 5.0% | 60.0 | 5.0% |
| Ac-Di-Sol SD-711 | Croscarmellose sodium | 42.0 | 3.5% | 42.0 | 3.5% |
| LIGAMED MF-2-V | Magnesium stearate | 12.0 | 1.0% | 12.0 | 1.0% |

To a v-blender was added half of the Vivapur 105 and blended for one minute. To this was added Compound A Form III, the second half of the Vivapur 105, Aerosil 200, and Ac-Di-Sol SD-711 and blended for 3 minutes. Emcompress (anhydrous) was then added to the blend and further blended for 3 minutes. The blend was then screened through a US 12 mesh screen. LIGAMED MF-2-V was then screened through a US 20 mesh screen and added to the blend. The resulting mixture was blended for 2 minutes. The resulting mixture was double bagged with desiccant packs inserted between bags and sealed in a drum for storage.

A roller compactor was set up with smooth rollers, a micro hopper, 1.0 mm screen, 2 mm gap width, a compaction force of 5 kN/cm and a roller speed of 1 revolution/minute. The Compound A blend was then added to the hopper, refilling as necessary during processing. The material from the roller compactor was collected in the dry granulation bag.

The extragranular Ac-Di-Sol SD-711 and Prosolv SMCC 90 LM was screened through a US 12 mesh screen and blended with the granulated material for 3 minutes. Next, LIGAMED MF-2-V was screened through a US 20 mesh screen and added to the blend. The resulting mixture was blended for 2 minutes and then collected in a bag.

Example 11. Compound A Form III Pharmaceutical Composition 3

In Examples 11-14, where 275 mg and 550 mg tablets are referred to, this is the weight of the nucleotide without the hemisulfate salt.

| Component | Theoretical 275 mg mg/tablet | Theoretical 550 mg mg/tablet | Theoretical % w/w | Adjusted for Purity 275 mg mg/tablet | Adjusted for Purity 550 mg mg/tablet | Adjusted for Purity % w/w |
|---|---|---|---|---|---|---|
| Intragranular | | | | | | |
| Compound A Form III | 298.3 | 596.5 | 49.7% | 302.9 | 605.7 | 50.5% |
| Pearlitol 100 SD | 81.0 | 162.0 | 13.5% | 81.0 | 162.0 | 13.5% |
| Prosolv SMCC 90 LM | 127.7 | 255.5 | 21.3% | 123.1 | 246.3 | 20.5% |
| Aerosil 200 | 6.0 | 12.0 | 1.0% | 6.0 | 12.0 | 1.0% |
| Ac-Di-Sol SD-711 | 27.0 | 54.0 | 4.5% | 27.0 | 54.0 | 4.5% |
| LIGAMED MF-2-V | 3.0 | 6.0 | 0.5% | 3.0 | 6.0 | 0.5% |
| Extragranular | | | | | | |
| Prosolv SMCC 90 LM | 30.0 | 60.0 | 5.0% | 30.0 | 60.0 | 5.0% |
| Ac-Di-Sol SD-711 | 21.0 | 42.0 | 3.5% | 21.0 | 42.0 | 3.5% |
| LIGAMED MF-2-V | 6.0 | 12.0 | 1.0% | 6.0 | 12.0 | 1.0% |
| Total | 600.0 | 1200.0 | 100% | 600.0 | 1200.0 | 100% |

Preparation of Compound A Form III pharmaceutical composition 3 can be carried out following the procedures described in Examples 9 and 10.

Example 12. Compound A Form III Pharmaceutical Composition 4

| Component | Theoretical 275 mg mg/tablet | Theoretical 550 mg mg/tablet | Theoretical % w/w | Adjusted for Purity 275 mg mg/tablet | Adjusted for Purity 550 mg mg/tablet | Adjusted for Purity % w/w |
|---|---|---|---|---|---|---|
| Intragranular | | | | | | |
| Compound A Form III | 298.3 | 596.5 | 49.7% | 302.9 | 605.7 | 50.5% |
| Emcompress (anhydrous) | 52.2 | 104.4 | 8.7% | 51.0 | 102.1 | 8.5% |
| Vivapur 105 | 156.6 | 313.1 | 26.1% | 153.1 | 306.2 | 25.5% |
| Aerosil 200 | 6.0 | 12.0 | 1.0% | 6.0 | 12.0 | 1.0% |
| Ac-Di-Sol SD-711 | 27.0 | 54.0 | 4.5% | 27.0 | 54.0 | 4.5% |
| LIGAMED MF-2-V | 3.0 | 6.0 | 0.5% | 3.0 | 6.0 | 0.5% |

-continued

| Component | Theoretical 275 mg mg/tablet | Theoretical 550 mg mg/tablet | % w/w | Adjusted for Purity 275 mg mg/tablet | Adjusted for Purity 550 mg mg/tablet | % w/w |
|---|---|---|---|---|---|---|
| | | | Extragranular | | | |
| Prosolv SMCC 90 LM | 30.0 | 60.0 | 5.0% | 30.0 | 60.0 | 5.0% |
| Ac-Di-Sol SD-711 | 21.0 | 42.0 | 3.5% | 21.0 | 42.0 | 3.5% |
| LIGAMED MF-2-V | 6.0 | 12.0 | 1.0% | 6.0 | 12.0 | 1.0% |
| Total | 600.0 | 1200.0 | 100% | 600.0 | 1200.0 | 100% |

Preparation of Compound A Form III pharmaceutical composition 4 can be carried out following the procedures described in Examples 9 and 10.

Example 13. Compound A Form III Pharmaceutical Composition

| Component | Theoretical 275 mg mg/tablet | Theoretical 550 mg mg/tablet | % w/w | Adjusted for Purity 275 mg mg/tablet | Adjusted for Purity 550 mg mg/tablet | % w/w |
|---|---|---|---|---|---|---|
| | | | Intragranular | | | |
| Compound A Form III | 298.3 | 596.5 | 49.7% | 302.9 | 605.7 | 50.5% |
| Pearlitol 100 SD | 72.0 | 144.0 | 12.0% | 72.0 | 144.0 | 12.0% |
| Vivapur 103 | 127.7 | 255.5 | 21.3% | 123.1 | 246.3 | 20.5% |
| Aerosil 200 | 6.0 | 12.0 | 1.0% | 6.0 | 12.0 | 1.0% |
| Ac-Di-Sol SD-711 | 36.0 | 72.0 | 6.0% | 36.0 | 72.0 | 6.0% |
| LIGAMED MF-2-V | 3.0 | 6.0 | 0.5% | 3.0 | 6.0 | 0.5% |
| | | | Extragranular | | | |
| Prosolv SMCC 90 LM | 30.0 | 60.0 | 5.0% | 30.0 | 60.0 | 5.0% |
| Ac-Di-Sol SD-711 | 21.0 | 42.0 | 3.5% | 21.0 | 42.0 | 3.5% |
| LIGAMED MF-2-V | 6.0 | 12.0 | 1.0% | 6.0 | 12.0 | 1.0% |
| Total | 600.0 | 1200.0 | 100% | 600.0 | 1200.0 | 100% |

Preparation of Compound A Form III pharmaceutical composition 5 can be carried out following the procedures described in Examples 9 and 10.

Example 14. Compound A Form III Pharmaceutical Composition 6

| Component | Theoretical 275 mg mg/tablet | Theoretical 550 mg mg/tablet | % w/w | Adjusted for Purity 275 mg mg/tablet | Adjusted for Purity 550 mg mg/tablet | % w/w |
|---|---|---|---|---|---|---|
| | | | Intragranular | | | |
| Compound A Form III | 298.3 | 596.5 | 39.8% | 302.9 | 605.7 | 40.4% |
| Pearlitol 100 SD | 72.0 | 144.0 | 9.6% | 72.0 | 144.0 | 9.6% |
| Vivapur 103 | 277.7 | 555.5 | 37.0% | 273.1 | 546.3 | 36.4% |
| Aerosil 200 | 6.0 | 12.0 | 0.8% | 6.0 | 12.0 | 0.8% |
| Ac-Di-Sol SD-711 | 36.0 | 72.0 | 4.8% | 36.0 | 72.0 | 4.8% |
| LIGAMED MF-2-V | 3.0 | 6.0 | 0.4% | 3.0 | 6.0 | 0.4% |
| | | | Extragranular | | | |
| Prosolv SMCC 90 LM | 30.0 | 60.0 | 4.0% | 30.0 | 60.0 | 4.0% |
| Ac-Di-Sol SD-711 | 21.0 | 42.0 | 2.8% | 21.0 | 42.0 | 2.8% |
| LIGAMED MF-2-V | 6.0 | 12.0 | 0.8% | 6.0 | 12.0 | 0.8% |
| Total | 750.0 | 1500.0 | 100% | 750.0 | 1500.0 | 100% |

Preparation of Compound A Form III pharmaceutical composition 6 can be carried out following the procedures described in Examples 9 and 10.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A Compound A Form III isolated crystalline morphic form, wherein Compound A is of structure:

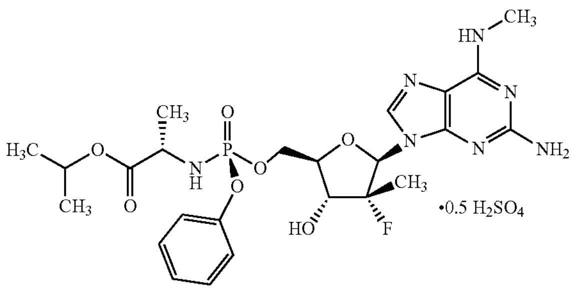 [SMILES: CNc1nc(N)nc2c1ncn2[C@@H]1O[C@H](CO[P@@](=O)(N[C@@H](C)C(=O)OC(C)C)Oc2ccccc2)[C@@H](O)[C@@]1(C)F]

and the morphic form is characterized by an XRPD pattern comprising at least three 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°.

2. The Compound A Form III of claim 1, characterized by an XRPD pattern comprising at least four 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°.

3. The Compound A Form III of claim 1, characterized by an XRPD pattern comprising at least five 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°.

4. The Compound A Form III of claim 1, characterized by an XRPD pattern comprising at least six 2theta values selected from 5.2±0.2°, 7.3±0.2°, 8.9±0.2°, 10.4±0.2° 13.6±0.2°, 14.7±0.2°, 17.0±0.2°, 18.2±0.2°, 19.9±0.2°, and 21.8±0.2°.

5. The Compound A Form III of claim 1, characterized by an XRPD pattern comprising the following 2theta values: 5.2±0.2°, 7.3±0.2°, 8.9±0.2°, 13.6±0.2°, 17.0±0.2°, 19.9±0.2°, and 21.8±0.2°.

6. A pharmaceutical composition comprising Compound A Form III of claim 1 and a pharmaceutically acceptable carrier.

7. The pharmaceutical composition of claim 6, in a solid dosage form.

8. The pharmaceutical composition of claim 7, wherein the solid dosage form is a tablet.

9. The pharmaceutical composition of claim 7, wherein the solid dosage form is a capsule.

10. The pharmaceutical composition of claim 7 that comprises at least about 400 mg of Compound A Form III.

11. The pharmaceutical composition of claim 7 that comprises at least about 200 mg of Compound A Form III.

12. The pharmaceutical composition of claim 7 that comprises at least about 250 mg of Compound A Form III.

13. The pharmaceutical composition of claim 7 that comprises at least about 300 mg of Compound A Form III.

14. The pharmaceutical composition of claim 7 that comprises at least about 350 mg of Compound A Form III.

15. The pharmaceutical composition of claim 7 that comprises about 300 mg of Compound A Form III.

16. The pharmaceutical composition of claim 7 that comprises between about 600 mg and about 1,200 mg of Compound A Form III.

17. The pharmaceutical composition of claim 7 that comprises between about 400 mg and about 1,000 mg of Compound A Form III.

18. The pharmaceutical composition of claim 7 that comprises between about 500 mg and about 800 mg of Compound A Form III.

19. The pharmaceutical composition of claim 7 that comprises from about 300 mg to about 1,200 mg of Compound A Form III.

20. The pharmaceutical composition of claim 7 that comprises about 600 mg of Compound A Form III.

21. The pharmaceutical composition of claim 7 that comprises at least 300 mg of Compound A Form III.

22. The pharmaceutical composition of claim 7 that comprises 300 mg of Compound A Form III.

23. The pharmaceutical composition of claim 7 that comprises from 300 mg to 1,200 mg of Compound A Form III.

* * * * *